(12) United States Patent
Xu

(10) Patent No.: US 11,771,420 B2
(45) Date of Patent: Oct. 3, 2023

(54) MULTIPURPOSE ENDOSCOPIC SURGICAL INSTRUMENT

(71) Applicant: Shanghai Boqia Medical Device Co., Ltd., Shanghai (CN)

(72) Inventor: Weihua Xu, Shanghai (CN)

(73) Assignee: Shanghai Boqia Medical Device Co., Ltd., Shanghai (CN)

(*) Notice: Subject to any disclaimer, the term of this patent is extended or adjusted under 35 U.S.C. 154(b) by 748 days.

(21) Appl. No.: 16/851,112

(22) Filed: Apr. 17, 2020

(65) Prior Publication Data

US 2020/0337695 A1 Oct. 29, 2020

(51) Int. Cl.
| | |
|---|---|
| *A61B 17/064* | (2006.01) |
| *A61B 17/068* | (2006.01) |
| *A61B 17/00* | (2006.01) |
| *A61B 17/072* | (2006.01) |

(52) U.S. Cl.
CPC .... *A61B 17/0686* (2013.01); *A61B 17/00234* (2013.01); *A61B 2017/0034* (2013.01); *A61B 2017/00464* (2013.01); *A61B 2017/00477* (2013.01); *A61B 2017/07257* (2013.01); *A61B 2017/07278* (2013.01); *A61B 2017/07285* (2013.01)

(58) Field of Classification Search
CPC . A61B 17/086; A61B 17/0686; A61B 17/115; A61B 17/1155
See application file for complete search history.

(56) References Cited

U.S. PATENT DOCUMENTS

| | | | | |
|---|---|---|---|---|
| 2014/0305990 | A1* | 10/2014 | Shelton, IV | A61B 17/072 227/176.1 |
| 2014/0309666 | A1* | 10/2014 | Shelton, IV | A61B 17/0686 606/139 |
| 2016/0310134 | A1* | 10/2016 | Contini | A61B 17/07207 |
| 2017/0086823 | A1* | 3/2017 | Leimbach | A61B 17/068 |
| 2017/0281187 | A1* | 10/2017 | Shelton, IV | A61B 17/3211 |
| 2017/0296213 | A1* | 10/2017 | Swensgard | A61B 17/105 |
| 2018/0360443 | A1* | 12/2018 | Shelton, IV | A61B 17/068 |
| 2019/0261991 | A1* | 8/2019 | Beckman | A61B 17/068 |

* cited by examiner

*Primary Examiner* — Eyamindae C Jallow

(57) ABSTRACT

The present disclosure provides a multipurpose endoscopic surgical instrument. The instrument adopts a technical feature in which an interchangeable tool and a tool holder are connected to each other by inserting the mounting key into the opening mounting groove, and adopts a technical feature that the driving member includes an inserting block at the front part. It realizes the technical solution that by moving the inserting block to insert into the interchangeable tool to prevent the mounting key from moving out of the opening of the mounting groove, the interchangeable tool can be mounted on the tool holder. It realizes the technical solution that by moving the inserting block to exit the interchangeable tool, the interchangeable tool can be moved out of the tool holder.

8 Claims, 57 Drawing Sheets

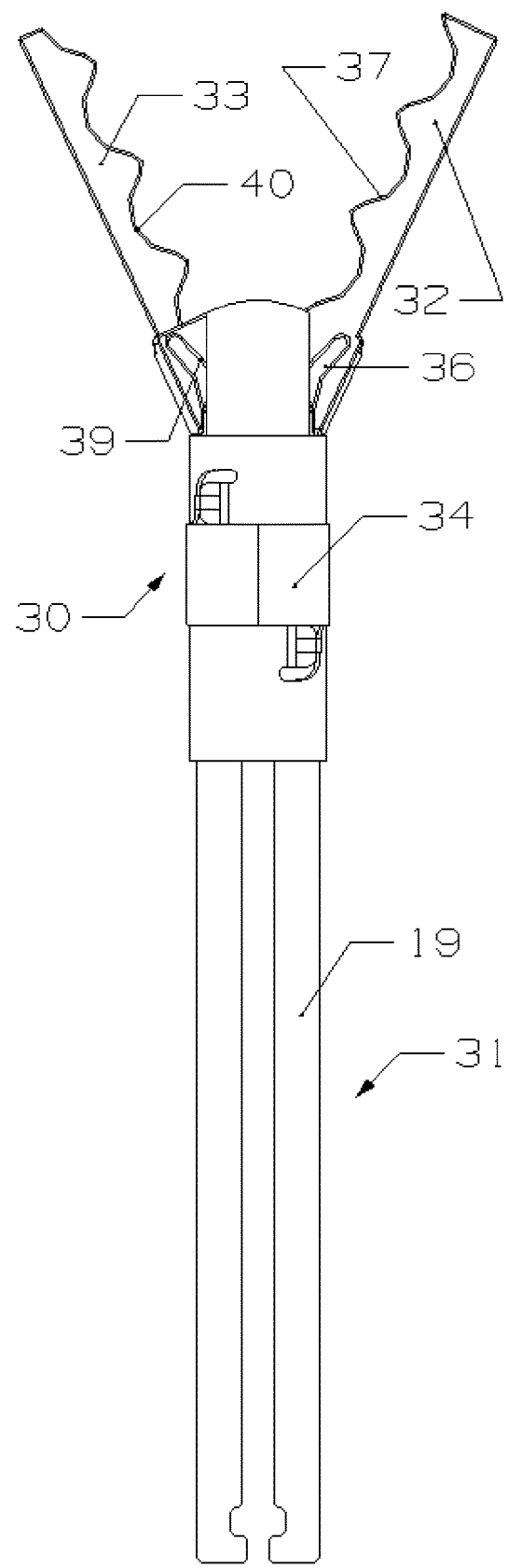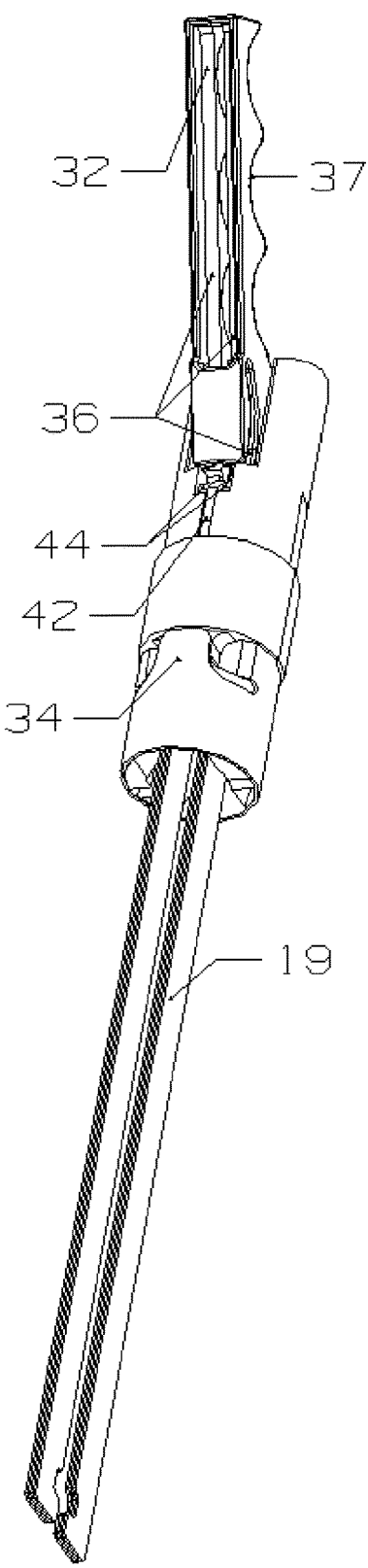
FIG. 15
FIG. 16

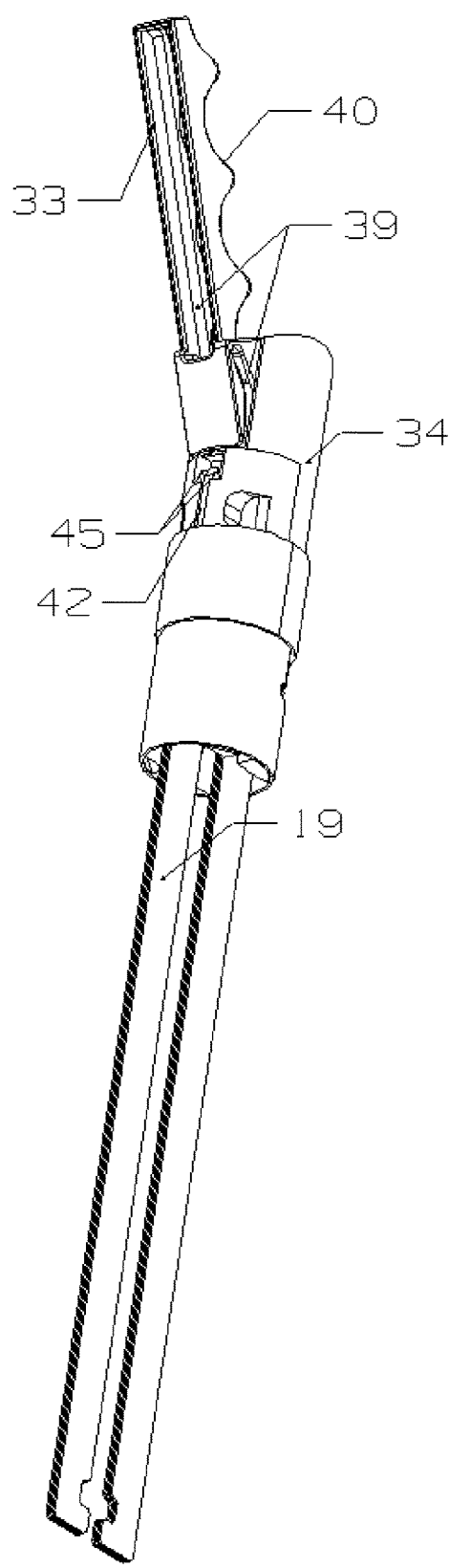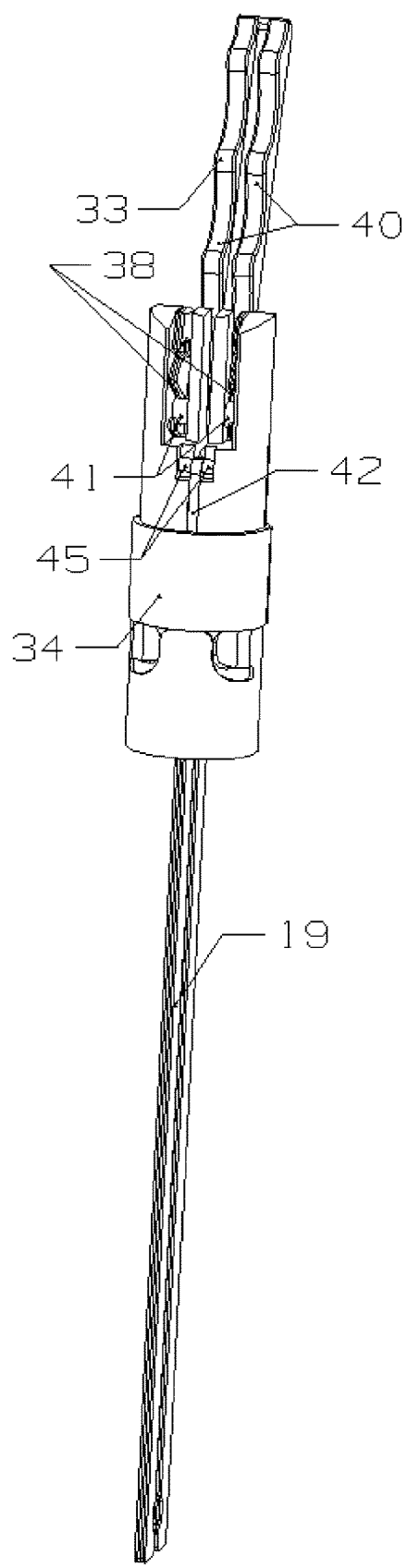
FIG. 19                               FIG. 20

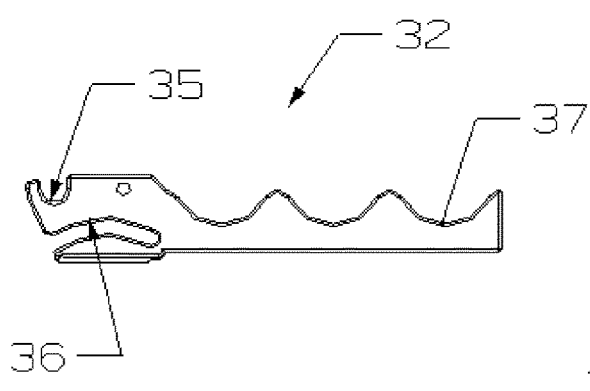
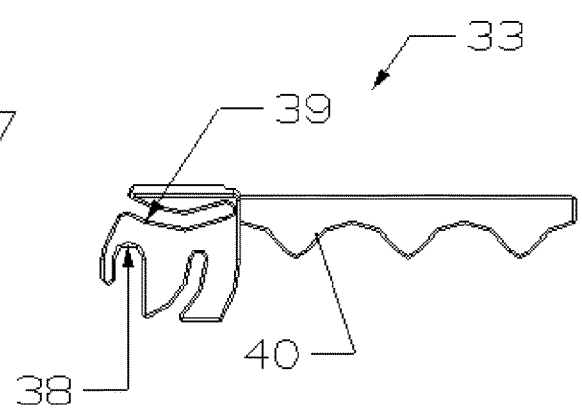
FIG. 24  FIG. 25
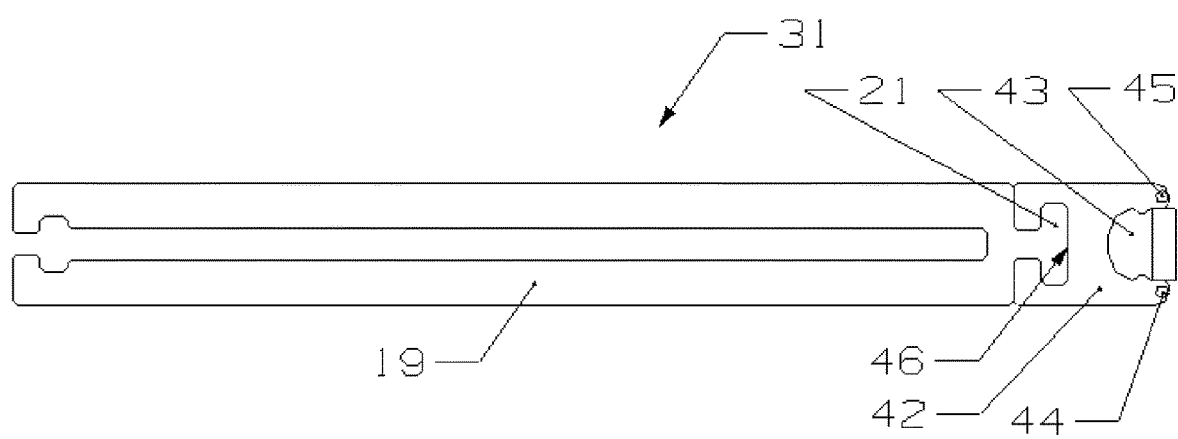
FIG. 26
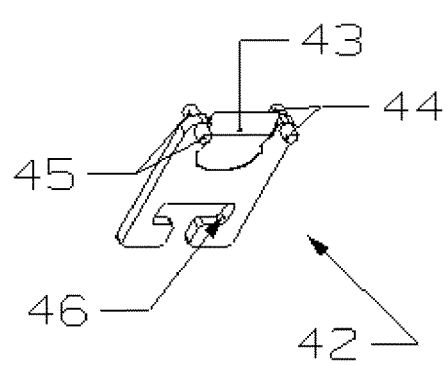
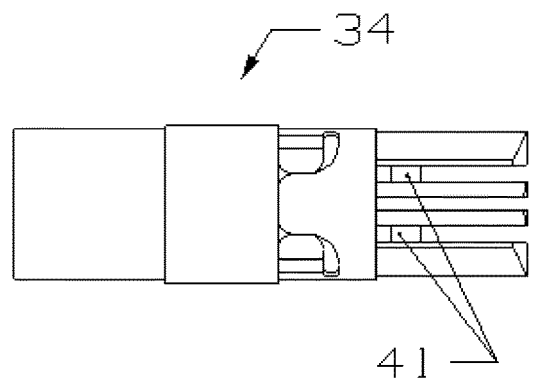
FIG. 27  FIG. 28

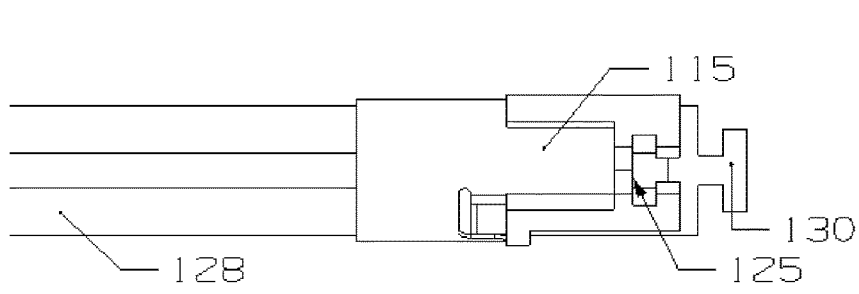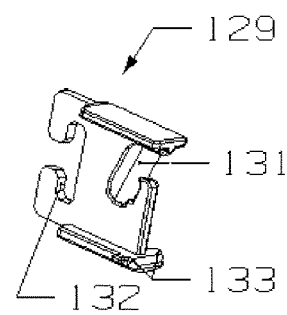
FIG. 75  FIG. 76
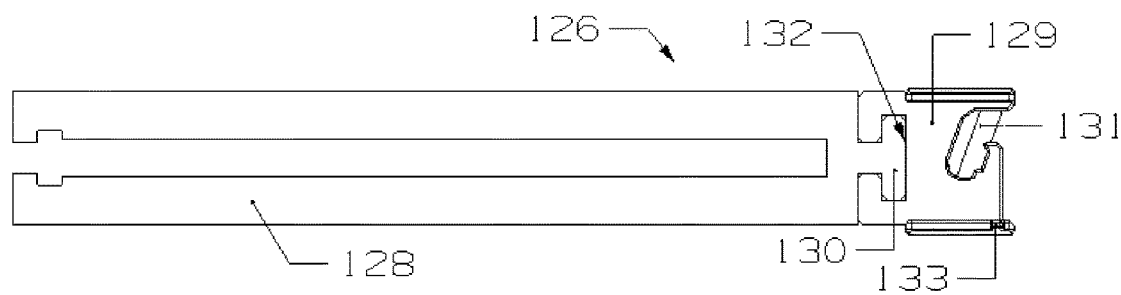
FIG. 77
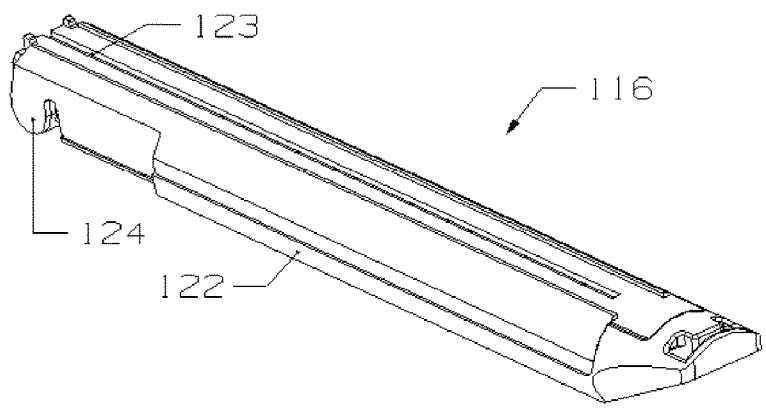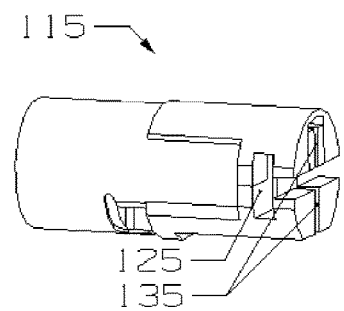
FIG. 78  FIG. 79
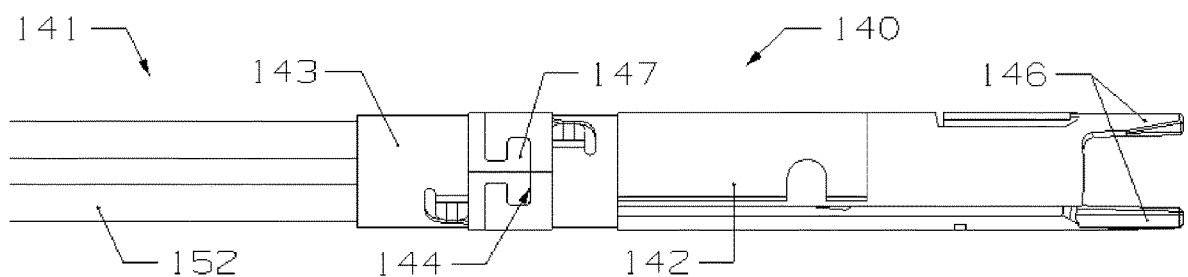
FIG. 80

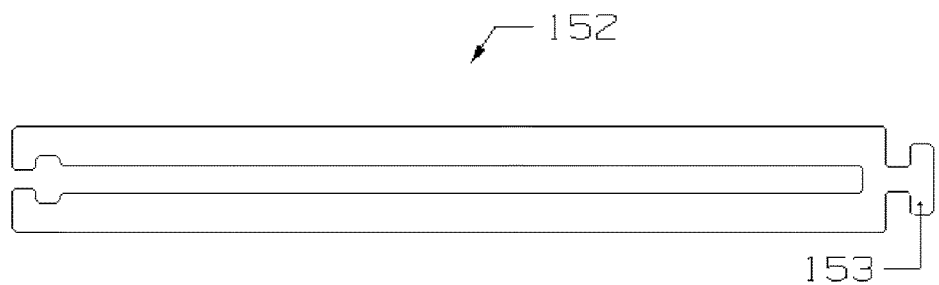
FIG. 92
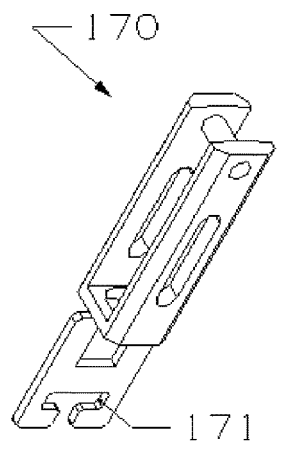 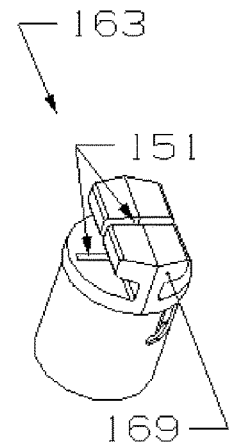
FIG. 93  FIG. 94
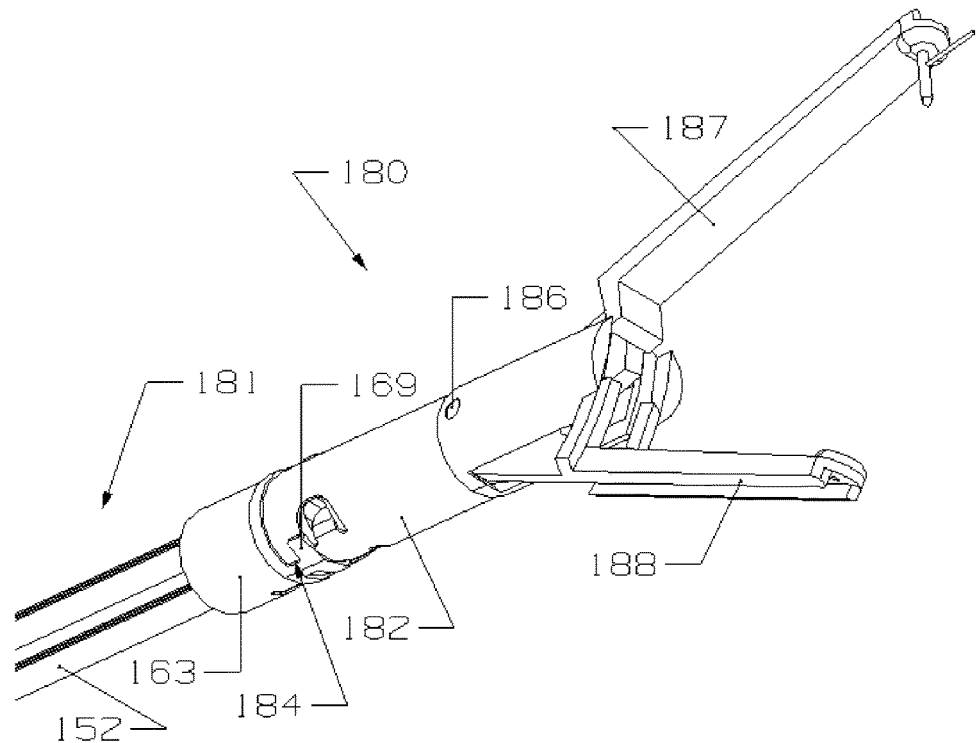
FIG. 95

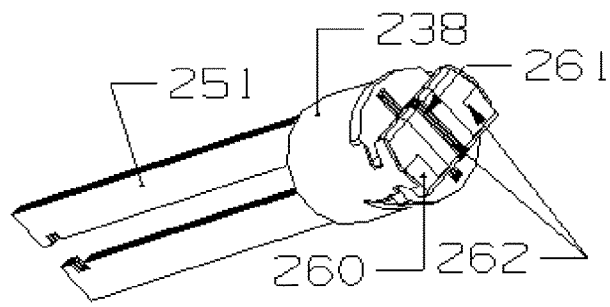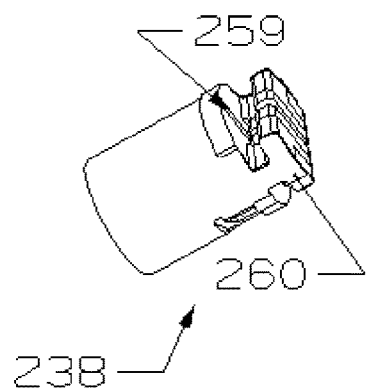
FIG. 111  FIG. 112
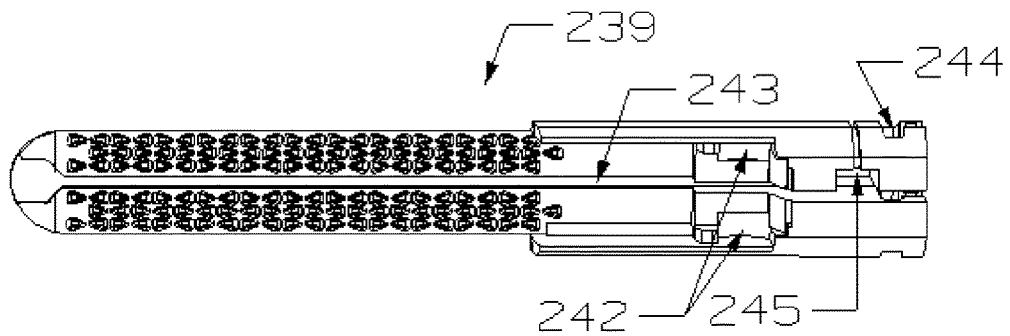
FIG. 113
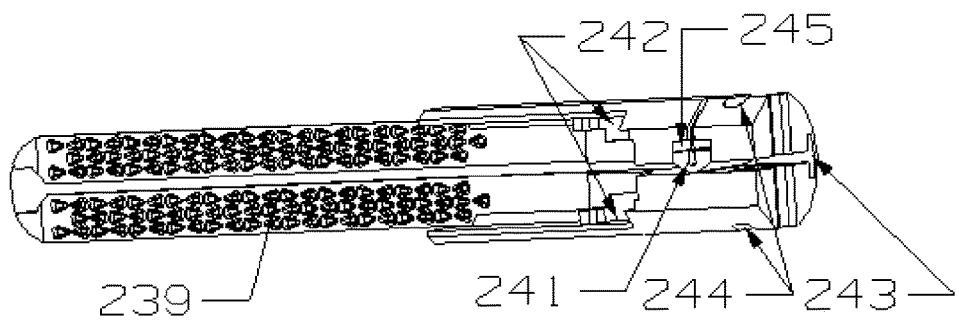
FIG. 114
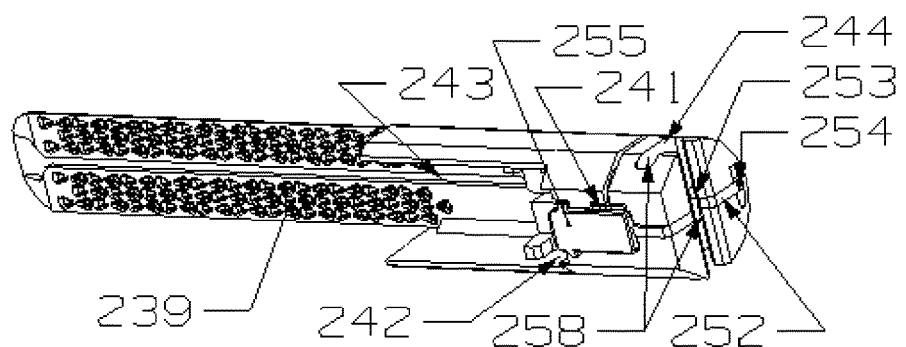
FIG. 115

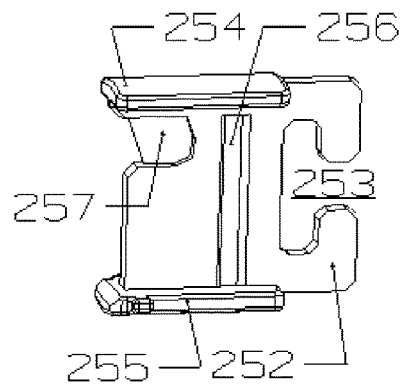
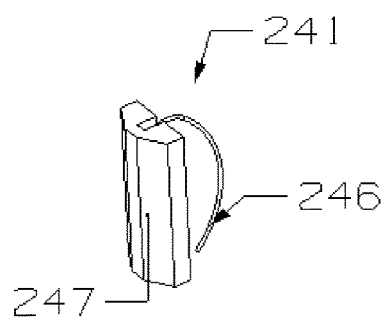
FIG. 116           FIG. 117
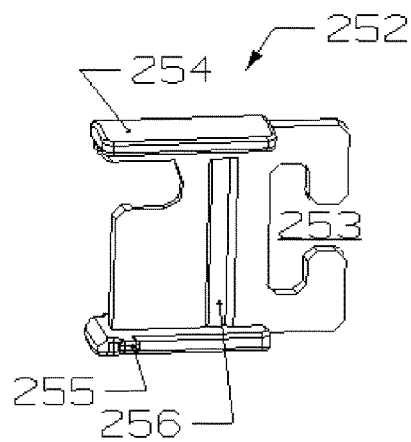
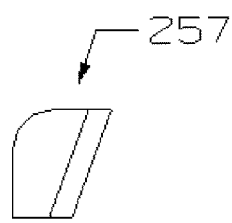
FIG. 118           FIG. 119
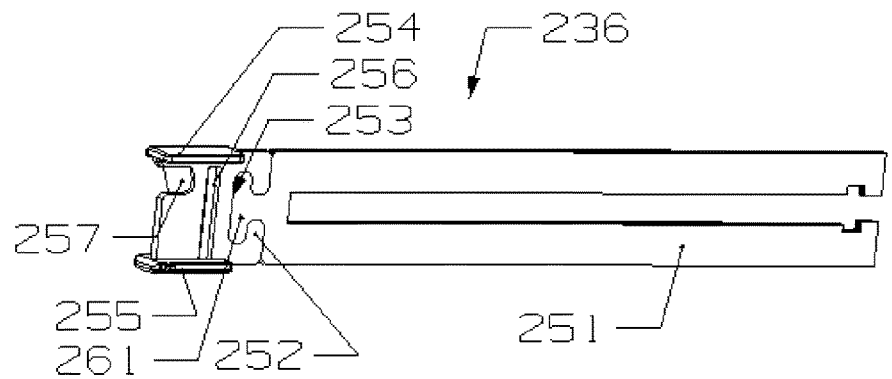
FIG. 120
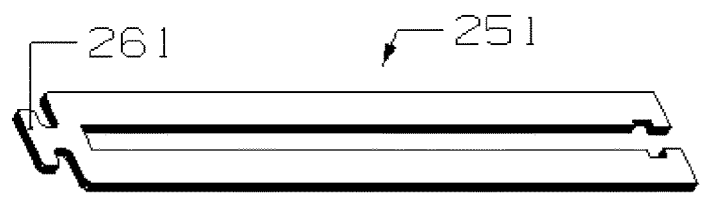
FIG. 121

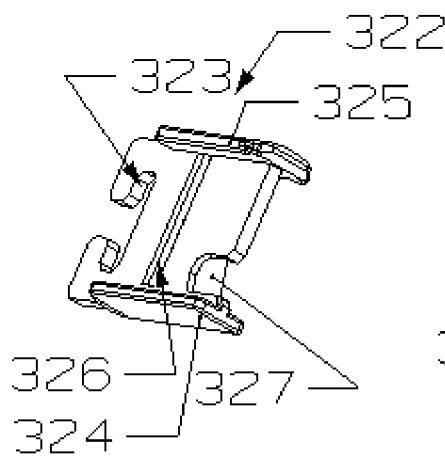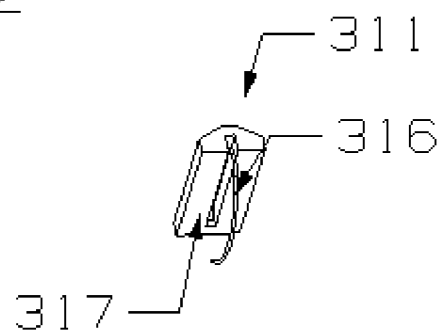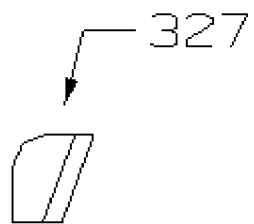
FIG. 145　　　　FIG. 146　　　　FIG. 147
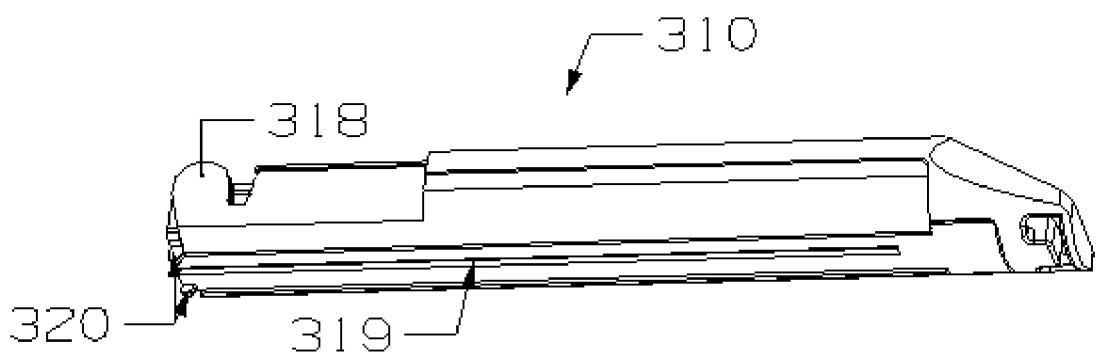
FIG. 148
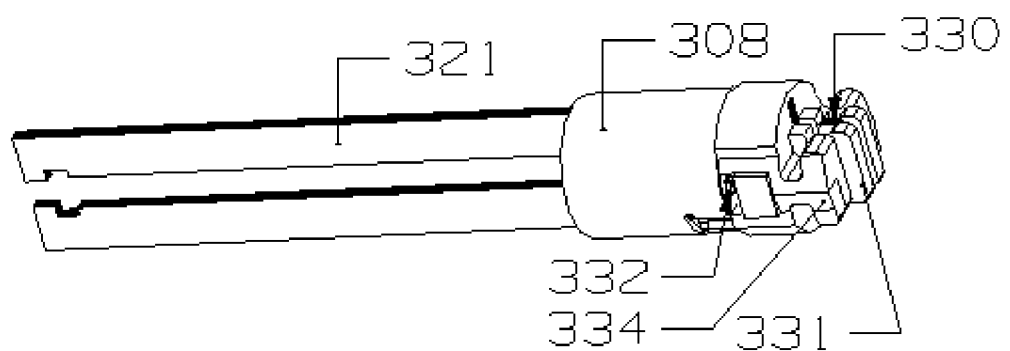
FIG. 149

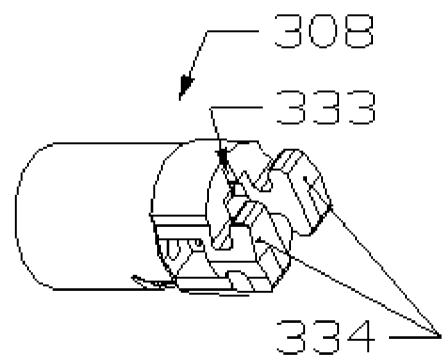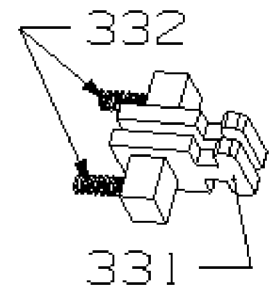
FIG. 153　　　　　　　FIG. 154
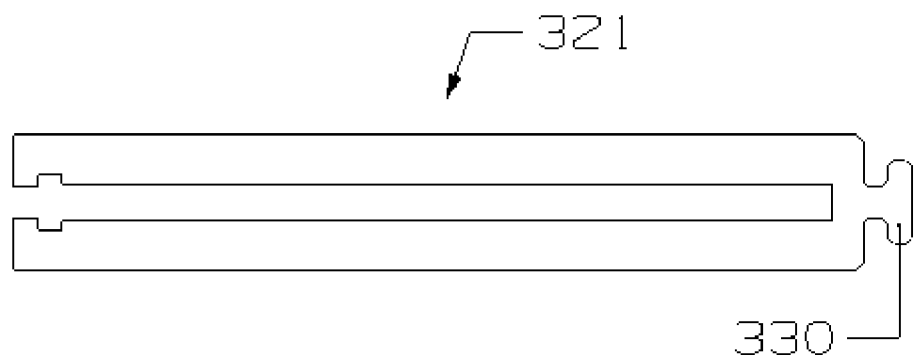
FIG. 155
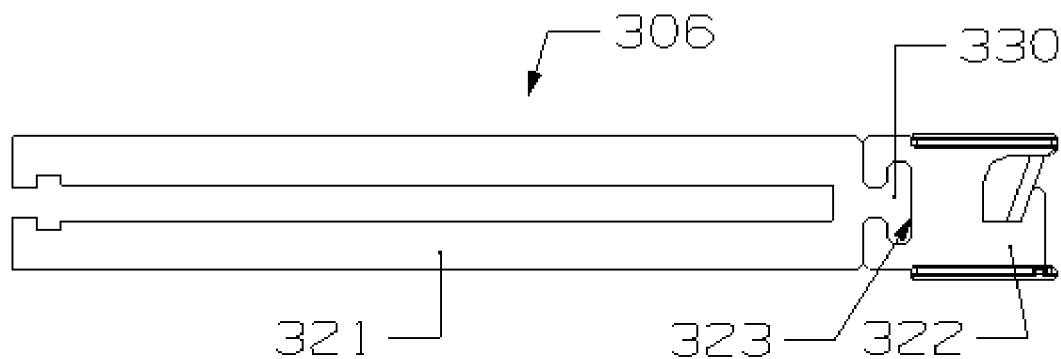
FIG. 156

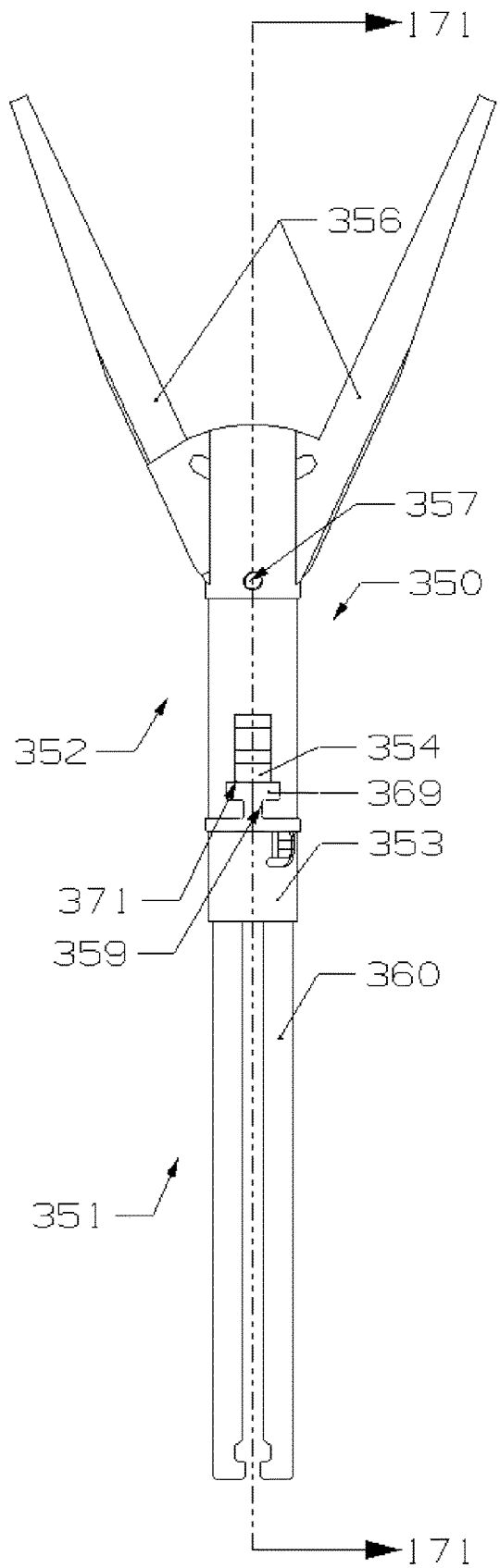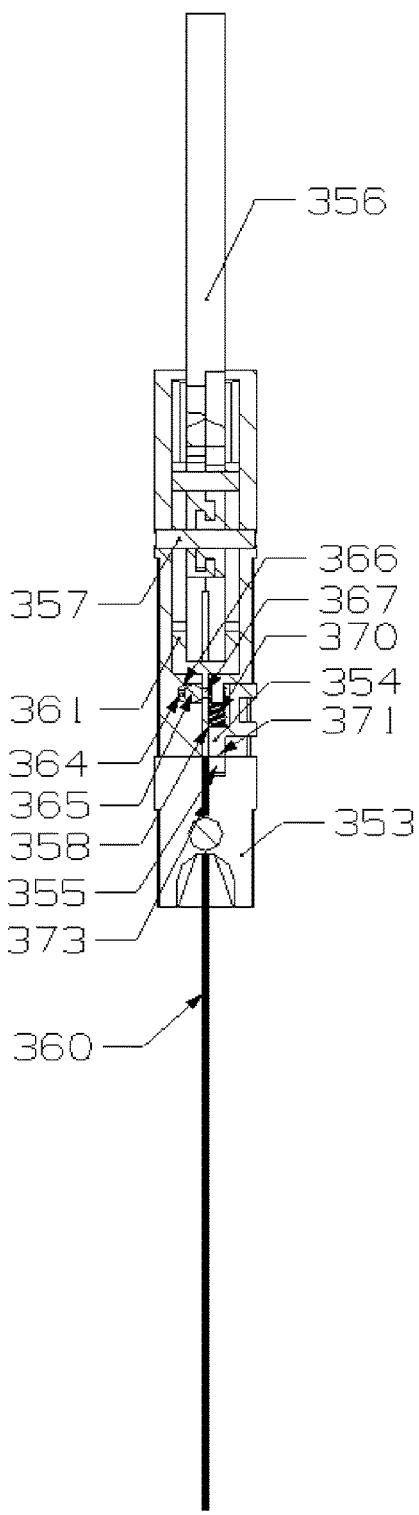
FIG. 170
FIG. 171

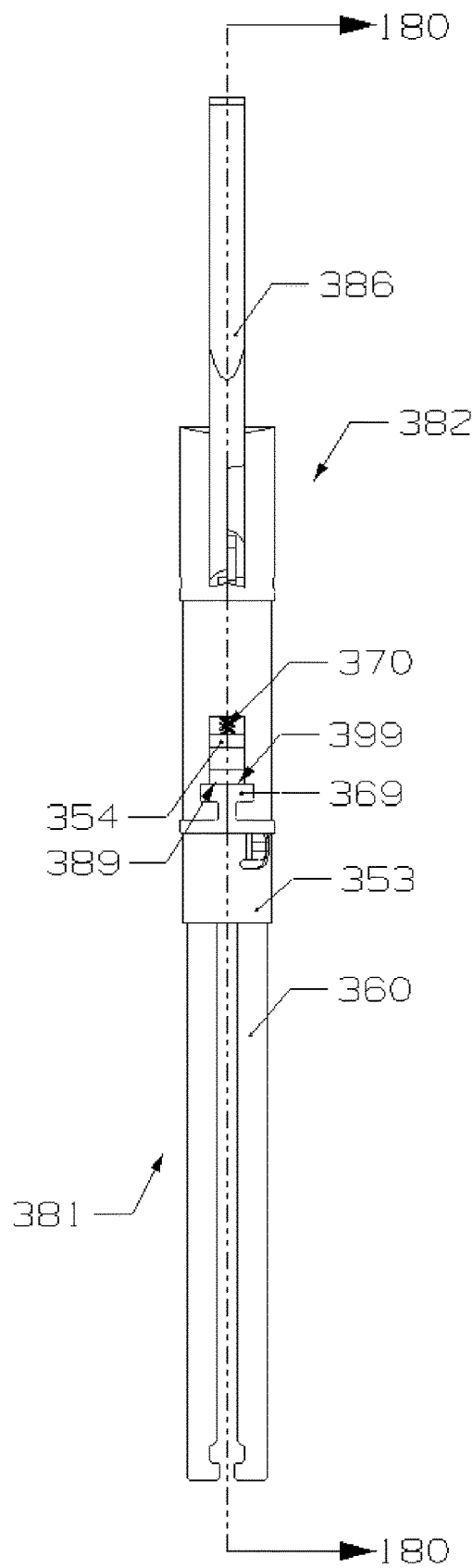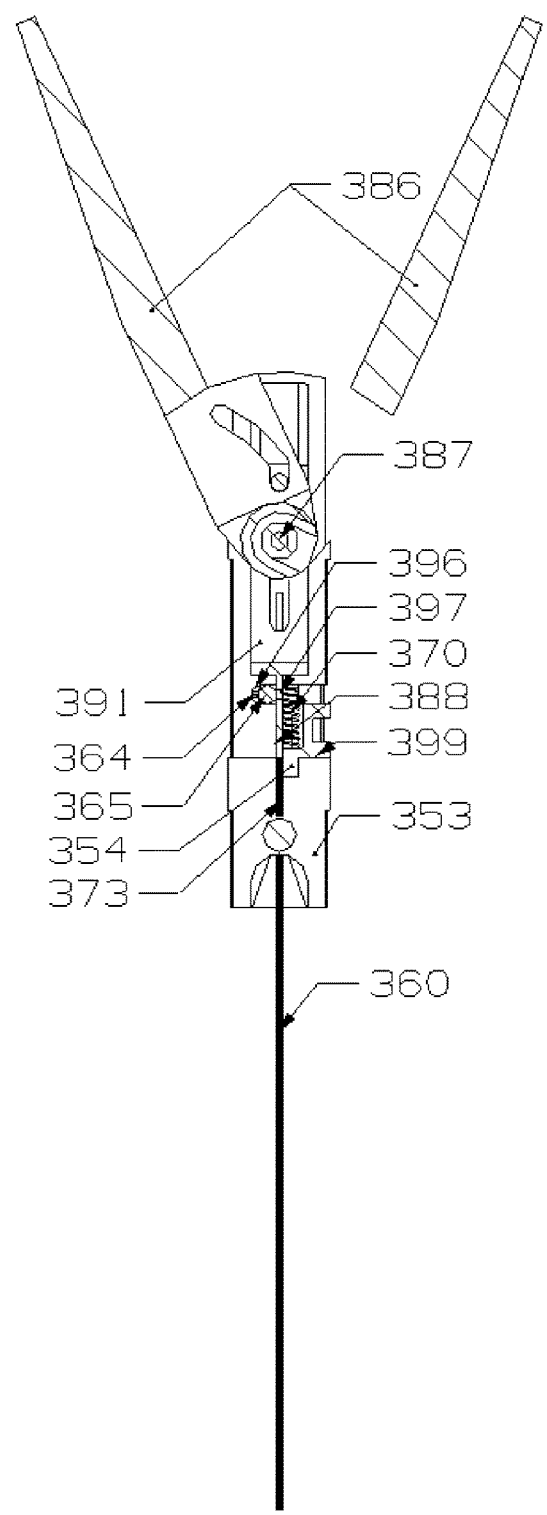
FIG. 179
FIG. 180 ically to the endoscopic surgical instrument used in laparoscopic surgery, and in particular to the endoscopic surgical instrument used in thoracoscopic surgery.

MULTIPURPOSE ENDOSCOPIC SURGICAL INSTRUMENT

CROSS REFERENCE TO RELATED APPLICATION

This application claims the benefits of priorities to Chinese Patent Application No. CN 2019103578054, entitled "Multipurpose Endoscopic Surgical Instrument", filed with CNIPA on Apr. 29, 2019, and Chinese Patent Application No. CN 2019112929882, entitled "Multipurpose Endoscopic Surgical Instrument", filed with CNIPA on Dec. 16, 2019, the contents of which are incorporated herein by reference in their entireties.

BACKGROUND

Field of Disclosure

The present disclosure relates to the endoscopic surgical instrument used in endoscopic surgery, in particular to the endoscopic surgical instrument used in laparoscopic surgery, and in particular to the endoscopic surgical instrument used in thoracoscopic surgery.

Description of Related Arts

In laparoscopic surgery and thoracoscopic surgery, various manual, electric and robotic endoscopic surgical instruments are commonly used for clamping, shearing, injecting, cutting, suturing and anastomotic surgery in the abdomen, thorax and urogenital system, so as to reduce surgical trauma, shorten the surgical time and improve surgical quality.

The endoscopic cutting stapler, endoscopic surgical suturing device, endoscopic surgical forceps, endoscopic surgical cutting forceps, endoscopic surgical fan-shaped forceps, endoscopic surgical clip applier, endoscopic surgical scissor, endoscopic surgical syringe, endoscopic surgical cutting knife, endoscopic surgical electric knife, endoscopic surgical ultrasonic knife and other endoscopic surgical instruments as described in U.S. Patents US20140014707A1, US20170150961A1, US20180049763A1, US20180078248A1, US20180116675A1, US20180126504A1 and US20180333185A1 consist of a tool assembly, an operation assembly and an elongated body. The elongated body may or may not include an articulation component. The elongated body connects the operation assembly and the tool assembly. The tool assembly may be a tool assembly without energy or a tool assembly with energy. The tool assembly includes a tool and a tool holder. The tool may be anvils and staple cartridges, or knives, forceps, cutting forceps, fan-shaped forceps, clip appliers, suture rods, scissors, clips, syringes, or any other tools that can be used in endoscopic surgery to meet the requirements for multiple purposes of endoscopic surgery. The operation assembly controls the actions of the tool in the tool assembly. The operation assembly may be a manual operation assembly as described in U.S. patents US20140014707A1 and US20180078248A1, or may be an electric operation assembly or a robotic operation assembly as described in U.S. patents US20170150961A1 and US20180126504A1.

The various endoscopic surgical instruments as described in U.S. patents US20170150961A1 and US20180049763A1 do not allow the replacement of tool assembly or tools after use. Therefore, if an endoscopic surgery has different purposes, it is necessary to replace the endoscopic surgical instruments with a different purpose. After each use of the endoscopic cutting stapler of the U.S. patent US20140014707A1, since the anvil is non-replaceable, only a staple cartridge with the same anastomotic length can be replaced. If a staple cartridge with a different anastomotic length needs to be replaced, then an endoscopic cutting stapler with a different anastomotic length needs to be replaced. After each use of the endoscopic cutting stapler of U.S. patent US20100200639A1, part of the elongated body and the entire tool assembly needs to be replaced with that of the same purpose. After each use of the endoscopic surgical instrument of U.S. Patent US20180078248A1, according to the requirements of the endoscopic surgery, part of the elongated body and the entire tool assembly may be replaced with that of the same purpose, or part of the elongated body and the entire tool assembly may be replaced with that of a different purpose. When replacing part of the elongated body and the entire tool assembly of the above two endoscopic surgical instruments, the elongated body, the replaced part elongated body and entire tool assembly must ensure that the clamping driving mechanism, the safety mechanism and the articulation rotary mechanism are precisely connected to each other. If one of the mechanisms is connected incorrectly, malfunctions may occur during the use of the endoscopic surgical instrument, resulting in failure in the use of the instrument. In addition, the structure of the replaceable tool assembly is complicated. Each endoscopic surgery needs to be equipped with a large number of endoscopic surgical instruments of various purposes, which are large in size and difficult to be made into reusable and replaceable elongated body, and difficult to be combined into endoscopic surgical instrument kits suitable for various surgical requirements. Therefore, the above two endoscopic surgical instruments are inconvenient and unsafe to use, the cost of replaceable tool assembly is high and the time to replace the tool assembly is long. The robotic endoscopic cutting stapler of U.S. patent US20180126504A1 uses two methods for replacing tool assembly of the same purpose after each use. One method is to only replace the staple cartridge with the same anastomotic length after each use: when replacing the staple cartridge, a special auxiliary hook is needed to pull the staple cartridge from the cartridge rack, then extracting the staple cartridge out of the cartridge rack, the endoscopic cutting stapler is moved to an appliance cabin, the selected staple cartridge is inserted into the cartridge rack, then the staple cartridge is pressed into the cartridge rack. Another method is to use part of the elongated body and the whole tool assembly as the replaceable tool assembly after each use: when replacing the replaceable tool assembly, a special auxiliary clip is needed to clamp the replaceable tool assembly; a surgical robot releases the safety mechanism between the elongated body and the replaced replaceable tool assembly, the replaceable tool assembly is rotated by a certain angle and extracted out of the elongated body, the endoscopic cutting stapler is moved to the appliance cabin, the selected replaceable tool assembly is inserted into the elongated body, then the replaceable tool assembly is rotated by a certain angle and fixed on the elongated body. The above two methods of replacing tool assembly require the endoscopic cutting stapler used by the robot to move toward different directions for multiple times. Once the connection is incorrect, malfunctions may occur during the use of the endoscopic cutting stapler, resulting in the failure in the use of the instrument. Therefore, only tool assembly with the same purpose can be replaced using the above two methods. The replacement is inconvenient and unsafe, the replaceable tool assembly is expensive, and it would take a long time to replace the tool assembly.

SUMMARY

A first object of the present disclosure is to provide a multipurpose endoscopic surgical instrument that adopts a technical feature in which the interchangeable tool and the tool holder are connected to each other by inserting the mounting key into the open-end mounting groove, and adopts a technical feature that the driving member includes an inserting block at the front; it realizes the technical solution that by moving the inserting block to insert into the interchangeable tool to prevent the mounting key from moving out of the opening of the mounting groove, the interchangeable tool can be mounted on the tool holder; it realizes the technical solution that by moving the inserting block to exit the interchangeable tool, the interchangeable tool can be moved out of the tool holder.

A second object of the present disclosure is to provide a multipurpose endoscopic surgical instrument, which adopts a technical feature in which the tool assembly includes a mounting key, an open-end mounting groove, a constraining key, a constraining groove and an opening elastic part, and adopts a technical feature that the interchangeable tool and the tool holder are connected to each other by inserting the mounting key into the open-end mounting groove; it realizes the technical solution of overcoming the force of the opening elastic part and pressing it on the middle back part of the interchangeable tool toward the direction of the rotating support of the interchangeable tool, and mounting the interchangeable tool on the tool holder; and it realizes the technical solution of overcoming the force of the opening elastic part and pressing it on the front part of the interchangeable tool toward the direction of the rotating support of the interchangeable tool, and removing the interchangeable tool from the tool holder.

A third object of the present disclosure is to provide a multipurpose endoscopic surgical instrument, which adopts the technical feature that an inlay key is inserted into the inlay groove between the driving bar and the driving head to form a driving head inlay connection; it realizes the technical solution that firstly the interchangeable tool is removed from the tool holder, then the operation assembly controls the driving head on the driving bar to move forward until the driving head extends out of the tool holder, the inlay key is removed from the inlay groove, the driving head is removed from the driving bar, and another driving head is mounted.

A fourth object of the present disclosure is to provide a multipurpose endoscopic surgical instrument, which adopts the technical feature that the mounting key is inserted into the open-end mounting groove between the tool holder and the interchangeable tool to form a tool inlay connection; it adopts the technical feature that the inlay key is inserted into the inlay groove between the driving bar and the driving head to form a driving head inlay connection; it adopts the technical feature in which the axis direction of the first type of pivot of the first type of interchangeable tool after the first type of interchangeable tool is mounted on the tool holder forms an angle with the axis direction of the second type of pivot of the second type of interchangeable tool after the second type of interchangeable tool is mounted on the tool holder; it realizes the technical solution in which the inserting block on the driving member moves forwards to insert into the tool slot of the interchangeable tool, such that the inserting block on the driving member prevents the mounting key from moving out of the mounting groove of the tool inlay connection, and the interchangeable tool is mounted on the tool holder; it realizes the technical solution in which the inserting block on the driving member moves forwards to insert into the tool slot of the interchangeable tool, such that the inserting block on the driving member prevents the mounting key from moving out of the mounting groove of the tool inlay connection, and the interchangeable tool is mounted on the tool holder, at the same time, the tool slot of the interchangeable tool prevents the inlay key from moving out of the inlay groove of the driving head inlay connection, then the driving head is mounted on the driving bar; it realizes the technical solution in which the endoscopic surgical instruments with the same plane for joint rotation may replace various tools with open/close directions mutually forming various angles with the direction of the inlay connection.

A fifth object of the present disclosure is to provide a multipurpose endoscopic surgical instrument, which adopts the technical feature in which the mounting key is inserted into the open-end mounting groove to form a tool inlay connection between the interchangeable tool and the tool holder, and adopts the technical feature in which the locking block and the locking groove are respectively located at the front side and the back side of the mounting joint between the tool inlay connection; it realizes the technical solution in which the locking block is inserted into the locking groove, and the locking block is inserted across the front side and the back side of the mounting joint between the tool inlay connection, such that the locking block prevents the mounting key from moving out of the mounting groove of the tool inlay connection, then the interchangeable tool can be mounted on the tool holder, and the driving head can be mounted on the driving bar at the same time; it realizes the technical solution in which the locking block exits the mounting joint between the tool inlay connection, and the mounting groove and the inlay groove are simultaneously removed from the mounting key and the inlay key in the replaceable inlay connection, then the interchangeable tool can be moved out of the tool holder, and the driving head can be moved out of the driving bar at the same time.

The objects of the present disclosure are achieved by the following technical solutions:

The endoscopic surgical instrument of the present disclosure includes a tool assembly, an elongated body and an operation assembly. The elongated body connects the operation assembly and the tool assembly. The tool assembly may be a tool assembly without energy or a tool assembly with energy. The tool assembly includes tools and a tool holder. Among the tools, one may be a tool fixed on the tool holder, the other may be one or several interchangeable tools, or all tools may be interchangeable tools. The interchangeable tool may be an anvil, a staple cartridge, a knife, forceps, cutting forceps, clip applier, suture rod, scissor, clip, syringe, or any other interchangeable tool that can be used in endoscopic surgery. The elongated body may include or not include an articulation joint. The operation assembly controls the actions of the tool assembly. The operation assembly may be a manual operation assembly, an electric operation assembly or a robotic operation assembly.

The tool assembly of the multipurpose endoscopic surgical instrument of the first technical solution according to the present disclosure comprises an interchangeable tool, a tool holder, a mounting key and an open-end mounting groove. The mounting key and the open-end mounting groove may have various shapes. The interchangeable tool is mounted on the tool holder. The interchangeable tool and the tool holder are connected to each other by inserting the mounting key into the opening of the mounting groove. The operation assembly comprises a driving member. The driving member comprises an inserting block at the front. The front part of the driving member may include a knife or other functional parts. The driving member controls the action of the tool assembly. The interchangeable tool includes a tool slot in a forward-backward direction. The tool slot may be a plane groove, a T-shaped groove or a curved groove, or a combination groove of a plane groove, a T-shaped groove and a curved groove.

During the process of mounting the interchangeable tool on the tool holder, step 1, the mounting key is inserted into the mounting groove through the opening of the mounting groove, and the interchangeable tool is inserted on the tool holder; step 2, the operation assembly controls the inserting block on the driving member to move along the tool slot, until the inserting block on the driving member prevents the mounting key from moving out of the opening of the mounting groove, and the interchangeable tool is mounted on the tool holder. During the process of removing the interchangeable tool from the tool holder, step 1, the operation assembly controls the inserting block on the driving member to move in the tool slot, until the inserting block on the driving member exits the position where the mounting key is prevented from moving out of the opening of the mounting groove; step 2, the mounting key is removed from the opening of the mounting groove, then the interchangeable tool can be removed from the tool holder; and the interchangeable tool may be selected. For the tool assemblies of various endoscopic surgical instruments, in order to achieve the same technical effect, the inserting block on the driving member controlled by the above-mentioned operation assembly may move forward along the tool slot, or move backward along the tool slot.

The interchangeable tool may be classified into a first type of interchangeable tool and a second type of interchangeable tool. The first type of interchangeable tool comprises a first tool and a first type of pivot, and the first tool rotates around the first type of pivot. The second type of interchangeable tool comprises a second tool and a second type of pivot, and the second tool rotates around the second type of pivot. The mounting key is inserted into the open-end mounting groove between the first type of interchangeable tool and the tool holder to form a tool inlay connection. The mounting key is inserted into the open-end mounting groove between the second type of interchangeable tool and the tool holder to form a tool inlay connection. The first type of interchangeable tool and the second type of interchangeable tool are not simultaneously mounted on the tool holder. An axis direction of the first type of pivot of the first type of interchangeable tool after the first type of interchangeable tool is mounted on the tool holder forms an angle with an axis direction of the second type of pivot of the second type of interchangeable tool after the second type of interchangeable tool is mounted on the tool holder.

In the first technical solution, the mounting key may be inserted into the open-end mounting groove between the interchangeable tool and the tool holder to form a tool inlay connection. During the process of removing the interchangeable tool from the tool holder, step 1, the operation assembly controls the inserting block on the driving member to move along the tool slot, until the inserting block on the driving member exits the position where the tool inlay connection is constrained; the mounting groove is removed out of the mounting key from the tool inlay connection; step 2, the interchangeable tool is removed from the tool holder; and the interchangeable tool may be selected. During the process of mounting the interchangeable tool on the tool holder, step 1, the operation assembly controls the inserting block on the driving member to move, until the inserting block on the driving member exits the position where the tool inlay connection is constrained; step 2, the mounting groove is inserted on the mounting key to form the tool inlay connection; step 3, the operation assembly controls the inserting block on the driving member to move along the tool slot, until the inserting block on the driving member prevents the mounting key from moving out of the opening of the mounting groove, and the interchangeable tool is mounted on the tool holder.

The tool holder may comprise the mounting key at a front part and a holder slot in a forward-backward direction. The interchangeable tool may comprise the open-end mounting groove at a back part. The driving member may comprise a driving bar and a driving head. The driving head comprises an opening inlay groove at a back part. The driving bar comprises an inlay key at a front part. The inlay key is inserted into the inlay groove between the driving bar and the driving head to form a driving head inlay connection. The position of the tool inlay connection is aligned to the position of the driving head inlay connection to form a replaceable inlay connection. The driving head is mounted in the tool slot of the interchangeable tool. The driving bar is mounted in the holder slot of the tool holder. When the mounting groove of the interchangeable tool and the inlay groove of the driving head are located at a position aligned with each other, a replaceable inlay groove is formed. When the mounting key of the tool holder and the inlay key of the driving bar are located at a position aligned with each other, a replaceable inlay key is formed. When the replaceable inlay key is inserted into the replaceable inlay groove, a replaceable inlay connection is formed. During the process of removing the interchangeable tool from the tool holder and removing the driving head from the driving bar at the same time, step 1, the driving member moves along the tool slot and the holder slot, the position of the tool inlay connection is aligned to the position of the driving head inlay connection to form the position of the replaceable inlay connection, the replaceable inlay groove is removed from the replaceable inlay key in the replaceable inlay connection; step 2, the interchangeable tool is moved out of the tool holder and the driving head is moved out of the driving bar at the same time; and the interchangeable tool or the driving head may be selected. During the process of mounting the interchangeable tool on the tool holder and mounting the driving head on the driving bar at the same time, step 1, the mounting key of the tool holder and the inlay key of the driving bar are located at a position aligned with each other to form the replaceable inlay key; step 2, the replaceable inlay groove is inserted on the replaceable inlay key to form the replaceable inlay connection, at this time, the mounting key of the tool holder is inserted into the mounting groove of the interchangeable tool between the tool holder and the interchangeable tool to form the tool inlay connection, and the inlay key of the driving bar is inserted into the inlay groove of the driving head between the driving bar and the driving head to form the driving head inlay connection; step 3, the driving member moves along the holder slot and the tool slot, such that the driving member prevents the mounting key of the tool holder from moving out of the mounting groove of the interchangeable tool, and the interchangeable tool is mounted on the tool holder, at the same time, the tool slot prevents the inlay key of the driving bar from moving out of the inlay groove of the driving head, and the driving head is mounted on the driving bar.

The tool holder may comprise the open-end mounting groove at a front part and a holder slot in a forward-backward direction. The interchangeable tool may comprise the mounting key at a back part. The driving member may comprise a driving bar and a driving head. The driving head comprises an inlay key at a back part. The driving bar comprises an opening inlay groove at a front part. The inlay key is inserted into the inlay groove between the driving bar and the driving head to form a driving head inlay connection. The position of the tool inlay connection is aligned to the position of the driving head inlay connection to form a replaceable inlay connection. The driving head is mounted in the tool slot of the interchangeable tool. The driving bar is mounted in the holder slot of the tool holder. When the mounting key of the interchangeable tool and the inlay block of the driving head are located at a position aligned with each other, a replaceable inlay block is formed. When the mounting groove of the tool holder and the inlay groove of the driving bar are located at a position aligned with each other, a replaceable inlay groove is formed. When the replaceable inlay block is inserted into the replaceable inlay groove, a replaceable inlay connection is formed. During the process of removing the interchangeable tool from the tool holder and removing the driving head from the driving bar at the same time, step 1, the driving member moves along the tool slot and the holder slot, the position of the tool inlay connection is aligned to the position of the driving head inlay connection to form the position of the replaceable inlay connection, the replaceable inlay groove is removed from the replaceable inlay key in the replaceable inlay connection; step 2, the interchangeable tool is moved out of the tool holder and the driving head is moved out of the driving bar at the same time; and the interchangeable tool and the driving head may be selected. During the process of mounting the interchangeable tool on the tool holder and mounting the driving head on the driving bar at the same time, step 1, the mounting groove of the tool holder and the inlay groove of the driving bar are located at the position aligned with each other to form the replaceable inlay groove; step 2, the replaceable inlay groove is inserted on the replaceable inlay block to form the replaceable inlay connection, at this time, the mounting groove of the tool holder is inserted on the mounting key of the interchangeable tool between the tool holder and the interchangeable tool to form the tool inlay connection, and the inlay groove of the driving bar is inserted into the inlay key of the driving head between the driving bar and the driving head to form the driving head inlay connection; step 3, the driving member moves along the holder slot and the tool slot, such that the driving member prevents the mounting groove of the tool holder from moving out of the mounting key of the interchangeable tool, and the interchangeable tool is mounted on the tool holder, at the same time, the tool slot prevents the inlay groove of the driving bar from moving out of the inlay key of the driving head, and the driving head is mounted on the driving bar.

A locating elastic part may be mounted in the interchangeable tool. When the driving head is mounted in the interchangeable tool, the locating elastic part acts on the driving head to constrain the interchangeable tool and the driving head at the position of the replaceable inlay connection.

In the first technical solution, the driving member may comprise a driving bar and a driving head. The driving head is classified into an in-use driving head and a spare driving head. An inlay key is inserted into an opening inlay groove between the driving bar and the in-use driving head to form the driving head inlay connection. The in-use driving head is mounted on the driving bar, while the spare driving head has not been mounted on the driving bar. During the process of replacing the in-use driving head, step 1, the interchangeable tool is removed from the tool holder; step 2, the operation assembly controls the in-use driving head on the driving bar to move forward until the in-use driving head extends out of the tool holder; step 3, the inlay key is removed from the inlay groove, then the in-use driving head is removed from the driving bar; step 4, the inlay key is inserted into the inlay groove between the driving bar and the spare driving head to form the driving head inlay connection, and the spare driving head is mounted on the driving bar; step 5, the operation assembly controls the spare driving head on the driving bar to move backward until the spare driving head returns to the tool holder; step 6, the interchangeable tool is mounted on the tool holder.

In the first technical solution, the tool holder may comprise an opening constraining groove, the inserting block may be located at the opening of the constraining groove, and the interchangeable tool may comprise a constraining key at the back part. During the process of mounting the interchangeable tool on the tool holder, step 1, the operation assembly controls the inserting block on the driving member to move backward at the opening of the constraining groove of the tool holder, so as to open the opening of the constraining groove; step 2, the mounting key and the constraining key are inserted into the mounting groove and the constraining groove through the opening of the mounting groove and the opening of the constraining groove; step 3, the operation assembly controls the inserting block on the driving member to move forward at the opening of the constraining groove, so as to close the opening of the constraining groove of the tool holder, such that the inserting block prevents the mounting key and the constraining key from moving out of the opening of the mounting groove and the opening of the constraining groove, and the interchangeable tool is mounted on the tool holder. During the process of removing the interchangeable tool from the tool holder, the operation assembly controls the inserting block on the driving member to move backward at the opening of the constraining groove of the tool holder, so as to open the opening of the constraining groove; the mounting key and the constraining key are removed from the opening of the mounting groove and the opening of the constraining groove, then the interchangeable tool is removed from the tool holder; and the interchangeable tool may be selected.

The tool assembly of the endoscopic surgical instrument of the second technical solution according to the present disclosure comprises an interchangeable tool, a tool holder, a mounting key, an open-end mounting groove, a locking block and a locking groove. The mounting key is inserted into the mounting groove between the tool holder and the interchangeable tool to form a tool inlay connection, and the interchangeable tool is mounted on the tool holder. The locking block and the locking groove are respectively located at a front side and a back side of a mounting joint in the tool inlay connection. During the process of mounting the interchangeable tool on the tool holder, step 1, the locking block is moved to the mounting joint where the tool inlay connection is formed; step 2, the mounting groove is inserted on the mounting key to form the tool inlay connection, and the interchangeable tool is mounted on the tool holder; step 3, the locking block is inserted into the locking groove, and the locking block is inserted across the front side and the back side of the mounting joint in the tool inlay connection, such that the locking block prevents the mounting key from moving out of the mounting groove of the tool inlay connection, then the interchangeable tool is mounted on the tool holder. During the process of removing the interchangeable tool from the tool holder, step 1, the locking block exits the locking groove, until the locking block exits the mounting joint in the tool inlay connection; step 2, the mounting groove is moved out of the mounting key from the tool inlay connection, then the interchangeable tool is removed from the tool holder; and the interchangeable tool may be selected.

The tool assembly may comprise a locking spring which causes the locking block to move toward a direction of the locking groove. When the locking block is inserted into the locking groove under the force of the locking spring, the locking block is inserted across the front side and the back side of the mounting joint in the tool inlay connection, such that the locking block prevents the mounting key from moving out of the mounting groove, then the interchangeable tool is mounted on the tool holder. When the locking block exits the locking groove by overcoming the force of the locking spring, the locking block exits the mounting joint in the tool inlay connection, such that the mounting key are removed from the mounting groove, then the interchangeable tool is removed from the tool holder; and the interchangeable tool may be selected.

The interchangeable tool may be classified into a first type of interchangeable tool and a second type of interchangeable tool. The first type of interchangeable tool comprises a first tool and a first type of pivot, and the first tool rotates around the first type of pivot. The second type of interchangeable tool comprises a second tool and a second type of pivot, and the second tool rotates around the second type of pivot. The mounting key is inserted into the open-end mounting groove between the first type of interchangeable tool and the tool holder to form a tool inlay connection. The mounting key is inserted into the open-end mounting groove between the second type of interchangeable tool and the tool holder to form a tool inlay connection. The first type of interchangeable tool and the second type of interchangeable tool are not simultaneously mounted on the tool holder. An axis direction of the first type of pivot of the first type of interchangeable tool after the first type of interchangeable tool is mounted on the tool holder forms an angle with an axis direction of the second type of pivot of the second type of interchangeable tool after the second type of interchangeable tool is mounted on the tool holder.

The interchangeable tool may comprise a tool slot in a forward-backward direction. The tool holder may comprise a holder slot in a forward-backward direction. The operation assembly may comprise a driving member. The driving member moves forward and backward in the tool assembly, and the driving member participates in controlling actions of the tool assembly. The driving member comprises a driving bar, a driving head, an inlay key and an opening inlay groove. The inlay key is inserted into the inlay groove between the driving bar and the drive head to form a driving head inlay connection, and the driving head is mounted on the driving bar. A position of the tool inlay connection is aligned to a position of the driving head inlay connection to form a replaceable inlay connection. A locating elastic part is mounted in the interchangeable tool. When the driving head is mounted in the interchangeable tool, a part of the locating elastic part acts on the interchangeable tool, and another part acts on the driving head. During the process of removing the interchangeable tool from the tool holder and removing the driving head from the driving bar at the same time, step 1, the driving member moves along the tool slot and the holder slot, and the position of the tool inlay connection is aligned to the position of the driving head inlay connection to form the position of the replaceable inlay connection, and the locating elastic part constrains the interchangeable tool and the driving head at the position of the replaceable inlay connection; step 2, the locking block exits the locking groove, such that the locking block exits the mounting joint in the tool inlay connection; step 3, the mounting groove and the inlay groove are removed from the mounting key and the inlay key in the replaceable inlay connection simultaneously, then the interchangeable tool is moved out of the tool holder, and the driving head is moved out of the driving bar at the same time; and the interchangeable tool may be selected. During the process of mounting the interchangeable tool on the tool holder and mounting the driving head on the driving bar at the same time, step 1, the driving bar and the tool holder are located at position where the replaceable inlay connection is formed; step 2, the locking block moves to the mounting joint where the tool inlay connection is formed; step 3, the aligned mounting groove and the inlay groove are inserted on the aligned mounting key and inlay key simultaneously to form the replaceable inlay connection; step 4, the locking block is inserted into the locking groove across the front side and the back side of the mounting joint in the tool inlay connection, such that the locking block prevents the mounting key from moving out of the mounting groove of the tool inlay connection, then the interchangeable tool is mounted on the tool holder, and the driving head is mounted on the driving bar at the same time. The driving member is moved in the tool slot and the holder slot, such that the driving member prevents the mounting key from moving out of the mounting groove, at the same time, the interchangeable tool is further constrained on the tool holder, and the tool slot prevents the inlay key from moving out of the inlay groove to further constrain the driving head on the driving bar.

The tool assembly of the multipurpose endoscopic surgical instrument of the third technical solution according to the present disclosure comprises a mounting key, an open-end mounting groove, an opening elastic part, an interchangeable tool and a tool holder. The interchangeable tool is mounted on the tool holder. The tool holder comprises a constraining groove. The interchangeable tool comprises a constraining key at a back part. The mounting key is inserted into the open-end mounting groove between the tool holder and the interchangeable tool to form a rotating support of the interchangeable tool. A force of the opening elastic part causes the interchangeable tool to rotate within a limited angle around the rotating support of the interchangeable tool toward an opening direction. During the process of mounting the interchangeable tool on the tool holder, step 1, the force of the opening elastic part is overcome to insert the mounting key into the mounting groove through the opening of the mounting groove; step 2, under an action of the opening elastic part, the mounting key in the mounting groove, so as to drive the constraining key of the interchangeable tool to rotate into the constraining groove of the tool holder, and the interchangeable tool is mounted on the tool holder. During the process of removing the interchangeable tool from the tool holder, step 1, the force of the opening elastic part is overcome, such that the mounting key rotates in the mounting groove, so as to drive the constraining key of the interchangeable tool to rotate out of the constraining groove of the tool holder; step 2, the mounting key is removed from the mounting groove through the opening of the mounting groove, then the interchangeable tool is removed from the tool holder; and the interchangeable tool may be selected.

The force of the opening elastic part on the interchangeable tool may be located at middle-back part of the interchangeable tool. During the process of mounting the interchangeable tool on the tool holder, step 1, the force of the opening elastic part is overcome to press it on the middle-back part of the interchangeable tool towards a direction of the rotating support of the interchangeable tool, and the mounting key is inserted into the mounting groove through the opening of the mounting groove, then the interchangeable tool is loosened; step 2, under the action of the opening elastic part, the mounting key rotates in the mounting groove, so as to drive the constraining key of the interchangeable tool to rotate into the constraining groove of the tool holder, then the interchangeable tool is mounted on the tool holder. During the process of removing the interchangeable tool from the tool holder, step 1, the force of the opening elastic part is overcome to press it on a front part of the interchangeable tool towards the direction of the rotating support of the interchangeable tool, such that the mounting key rotates in the mounting groove, so as to drive the constraining key of the interchangeable tool to rotate out of the constraining groove of the tool holder; step 2, the force of the opening elastic part which is located at the middle-back part of the interchangeable tool pushes the interchangeable tool towards an opposite direction of the rotating support of the interchangeable tool, so as to push the mounting key out towards the opening of the mounting groove, then the interchangeable tool is removed from the tool holder; and the interchangeable tool may be selected.

The operation assembly may comprise a driving member. The driving member comprises a driving bar and a driving head. The driving head is classified into an in-use driving head and a spare driving head. An inlay key is inserted into an inlay groove between the driving bar and the in-use drive head to form a driving head inlay connection. The in-use driving head is mounted on the driving bar, while the spare driving head has not been mounted on the driving bar. During the process of replacing the in-use driving head, step 1, the interchangeable tool is removed from the tool holder; step 2, the operation assembly controls the in-use driving head on the driving bar to move forward until the in-use driving head extends out of the tool holder; step 3, the inlay key is removed from the inlay groove, and the in-use driving head is removed from the driving bar; step 4, the inlay key is inserted into the inlay groove between the driving bar and the spare driving head to form a driving head inlay connection, and the spare driving head is mounted on the driving bar; step 5, the operation assembly controls the spare driving head on the driving bar to move backward until the spare driving head returns to the tool holder; step 6, the interchangeable tool is mounted on the tool holder.

BRIEF DESCRIPTION OF THE DRAWINGS

FIG. 15 is a front view of the tool assembly and driving member according to the second embodiment of the present disclosure;

FIG. 16 is a perspective view showing a state in which the first interchangeable tool may be inserted or removed from the tool holder of FIG. 15;

FIG. 19 is a perspective view showing a state in which the second interchangeable tool of FIG. 15 may be inserted on or removed from the tool holder;

FIG. 20 is a perspective view showing the back of the position of FIG. 19;

FIG. 24 is a front view showing the first interchangeable tool of FIG. 15;

FIG. 25 is a front view showing the second interchangeable tool of FIG. 15;

FIG. 26 is a front view of the driving member of FIG. 15;

FIG. 27 is a perspective view of the driving head of FIG. 26;

FIG. 28 is a top view showing the tool holder of FIG. 15;

FIG. 69 is a bottom view showing that the tool holder and the driving member of FIG. 68 are in a state in which the replaceable part may be inserted on or removed from;

FIG. 75 is a front view showing that the driving head of FIG. 74 is removed from a driving bar;

FIG. 76 is a perspective view of the driving head;

FIG. 77 is a front view of the driving member of FIG. 68;

FIG. 78 is a perspective view showing the replaceable holder of FIG. 68;

FIG. 79 is a perspective view showing the tool holder of FIG. 68;

FIG. 80 is a front view of the tool assembly and driving member according to the sixth embodiment of the present disclosure;

FIG. 92 is a front view of the driving bar of FIG. 91;

FIG. 93 is a perspective view of the driving head of FIG. 91;

FIG. 94 is a perspective view showing the tool holder of FIG. 88;

FIG. 95 is a perspective view of the second type of interchangeable tool, the tool holder and the driving member according to the seventh embodiment;

FIG. 111 is a perspective view showing that the driving bar is mounted in the tool holder;

FIG. 112 is a perspective view showing the tool holder in FIG. 111;

FIG. 113 is a perspective view showing the straight replaceable anvil in FIG. 110;

FIG. 114 is a perspective view showing that the locating elastic part is mounted in the straight replaceable anvil of FIG. 113;

FIG. 115 is a perspective view showing that the straight driving head is inserted into the straight replaceable anvil of FIG. 114;

FIG. 116 is an enlarged perspective view of the straight driving head and knife in FIG. 115;

FIG. 117 is an enlarged perspective view showing the locating elastic part in FIG. 114;

FIG. 118 is an enlarged perspective view of the straight driving head in FIG. 116;

FIG. 119 is an enlarged front view of the knife in FIG. 116;

FIG. 120 is a perspective view of the driving member in FIG. 110;

FIG. 121 is a perspective view of the driving bar in FIG. 120;

FIG. 122 is a perspective view showing that the straight replaceable anvil and the driving head are inserted into the driving bar and the tool holder;

FIG. 123 is a perspective view showing that the straight staple cartridge is inserted into the straight replaceable anvil of FIG. 122;

FIG. 124 is a perspective view showing the closed state between the straight staple cartridge and the straight replaceable anvil of FIG. 110;

FIG. 125 is a perspective view showing the straight staple cartridge in FIG. 118;

FIG. 126 is a perspective view showing the back of the straight staple cartridge of FIG. 125;

FIG. 127 is a perspective view showing the driving member and the locating elastic part in FIG. 122;

FIG. 128 is a perspective view showing the driving member and the locating elastic part in FIG. 110;

FIG. 129 is a perspective view showing the driving member and the locating elastic part in FIG. 124;

FIG. 130 is a perspective view of the mounted tool assembly and driving member according to the tenth embodiment of the present disclosure;

Figure 130:
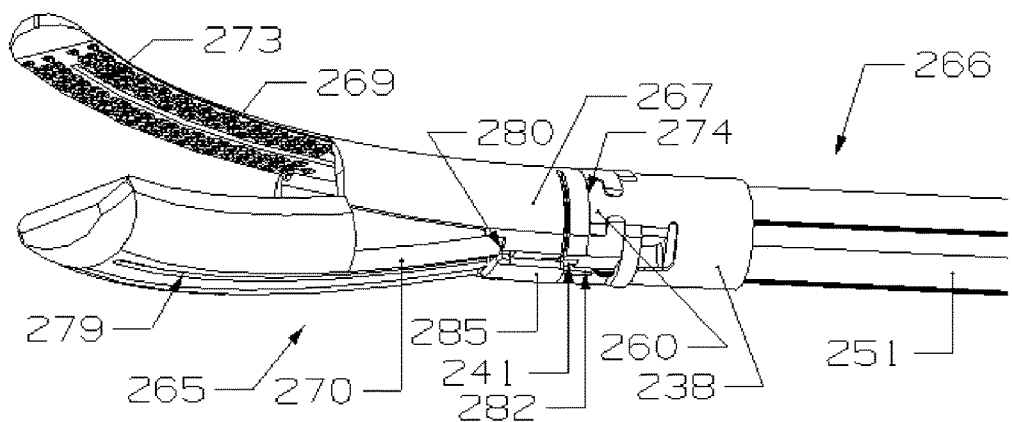
Figure 131:
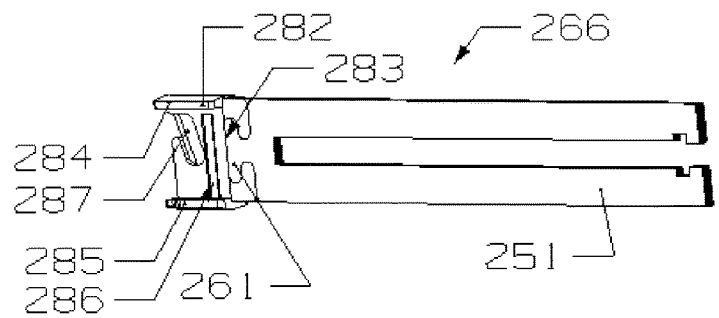
Figure 132:
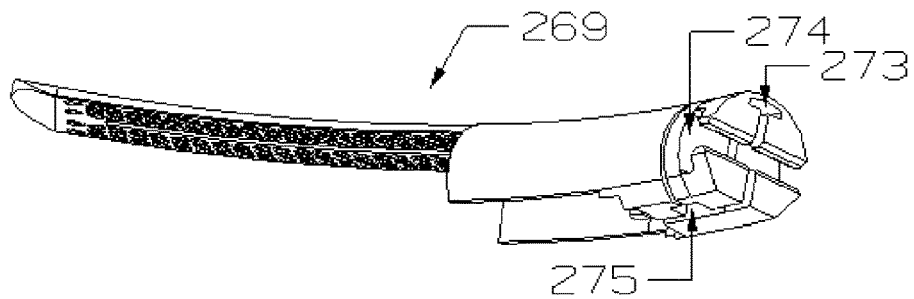
Figure 133:
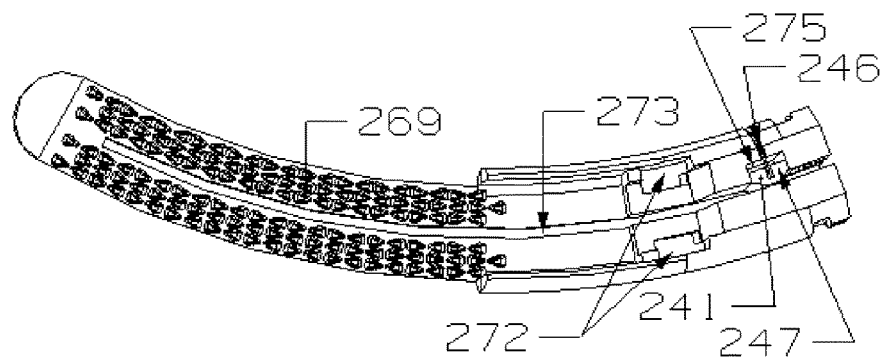
Figure 134:
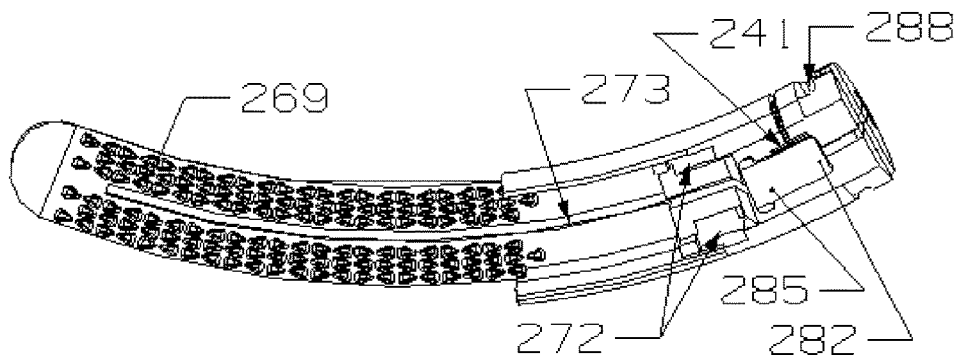
Figure 135:
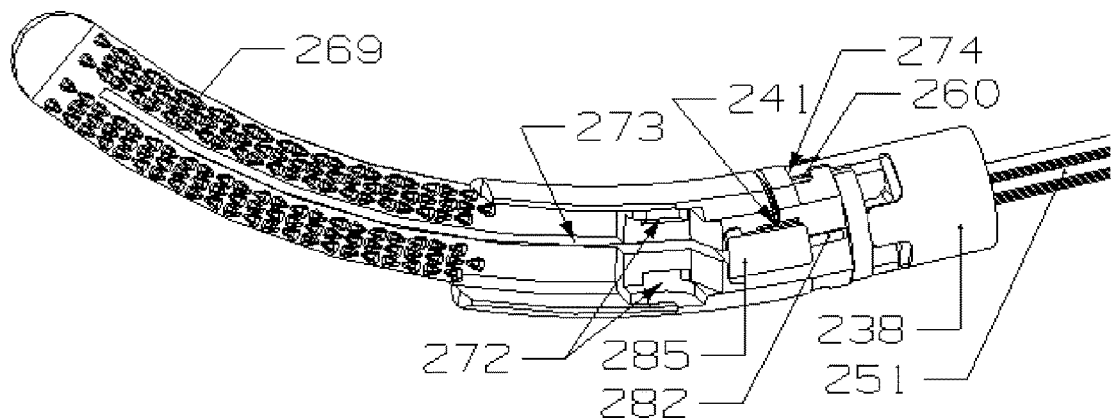
Figure 136:
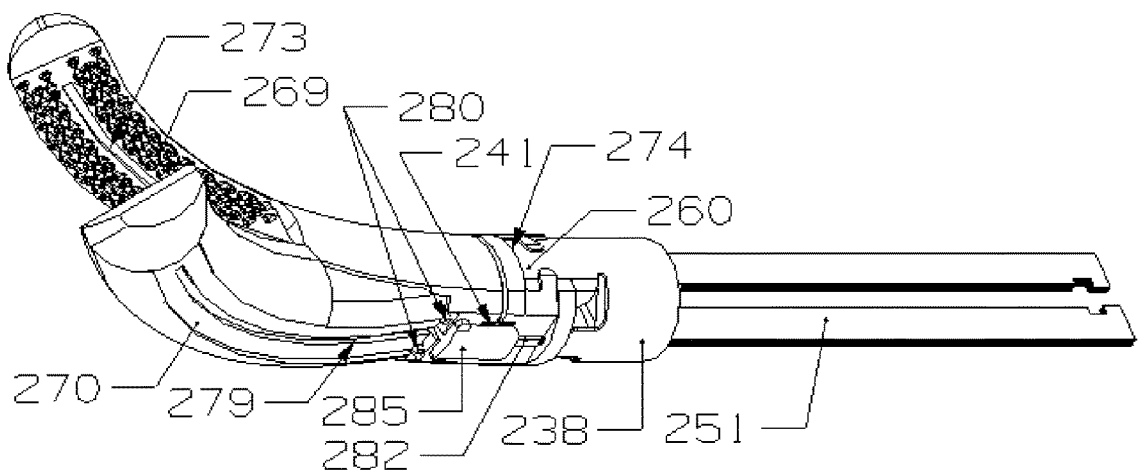
Figure 137:
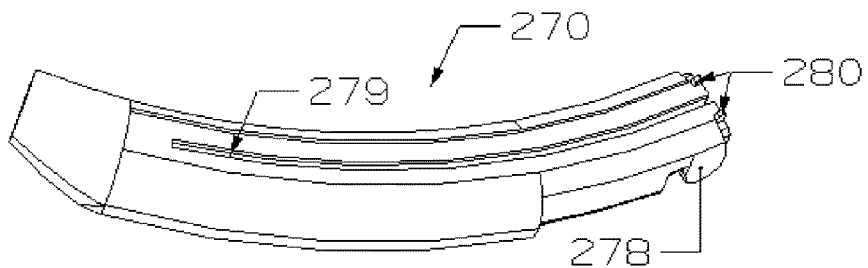
Figure 138:
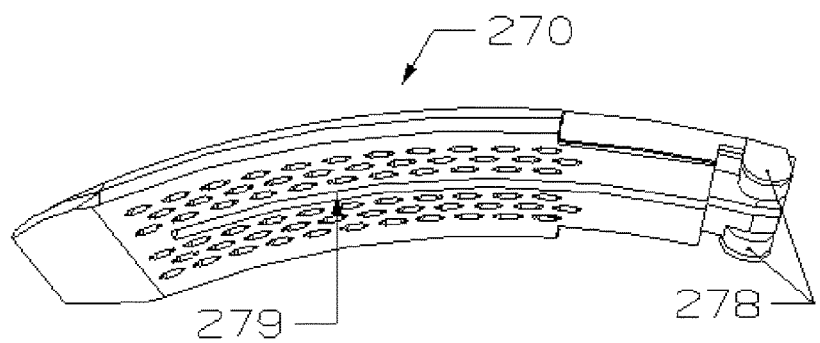
Figure 139:
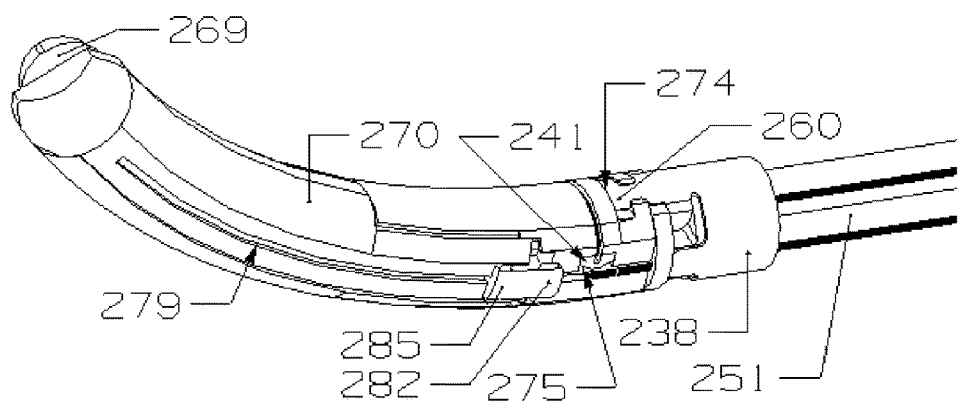
Figure 140:
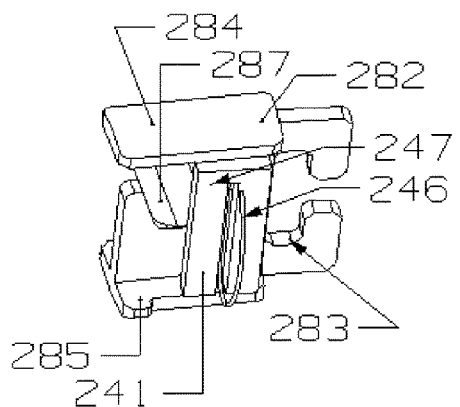
Figure 141:
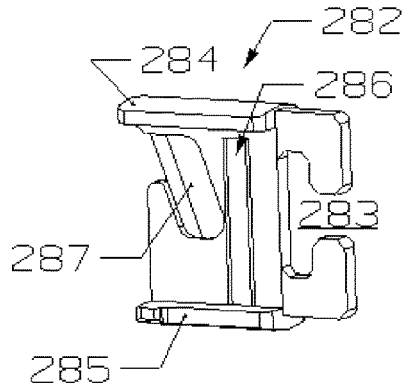
Figure 142:
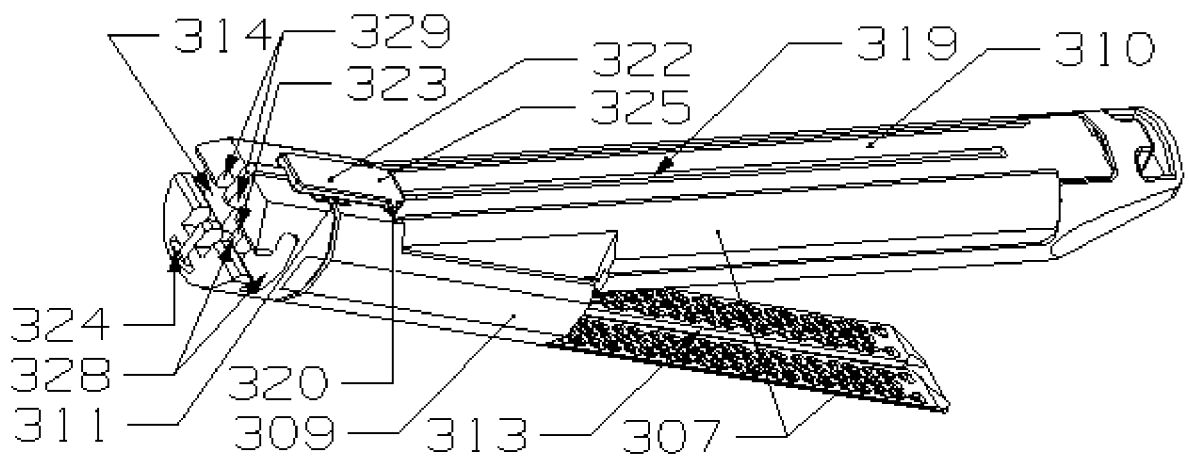
Figure 143:
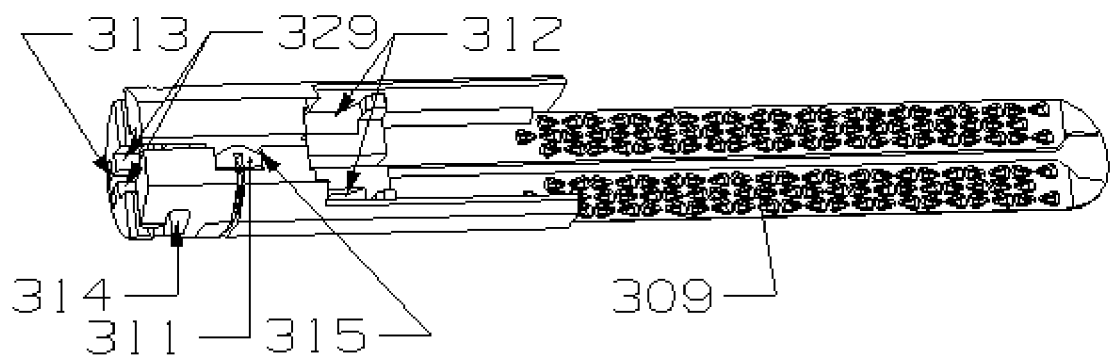
Figure 144:
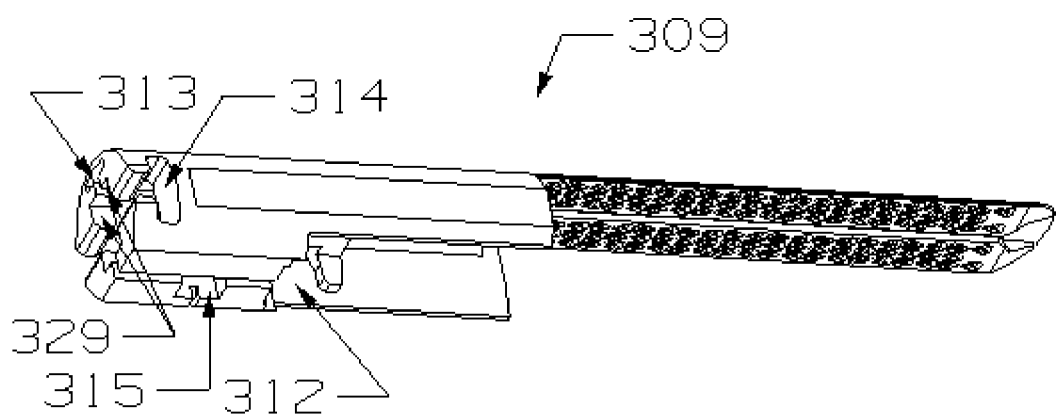
Figure 150:
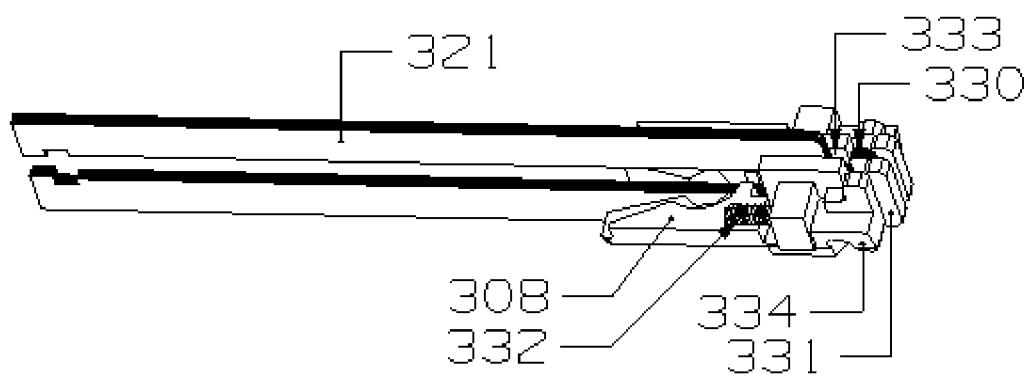
Figure 151:
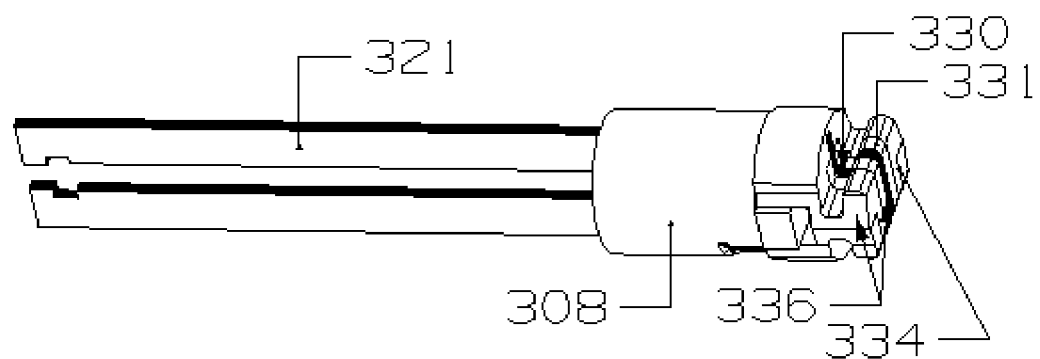
Figure 152:
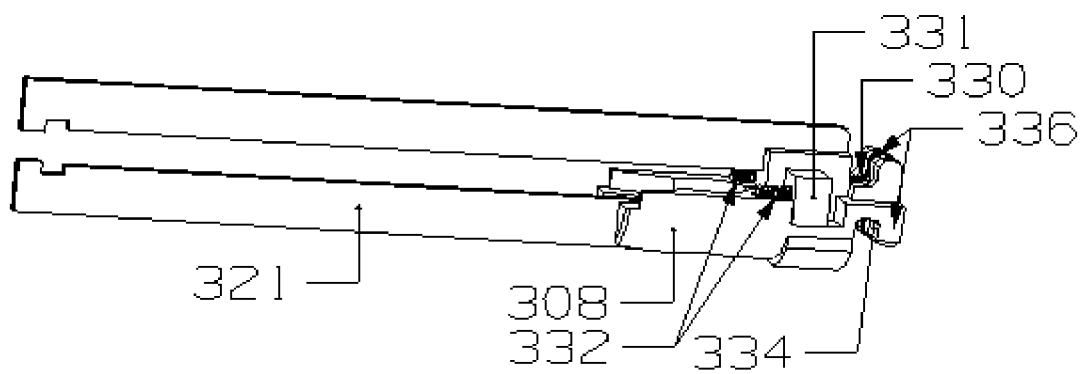
Figures 157, 158:
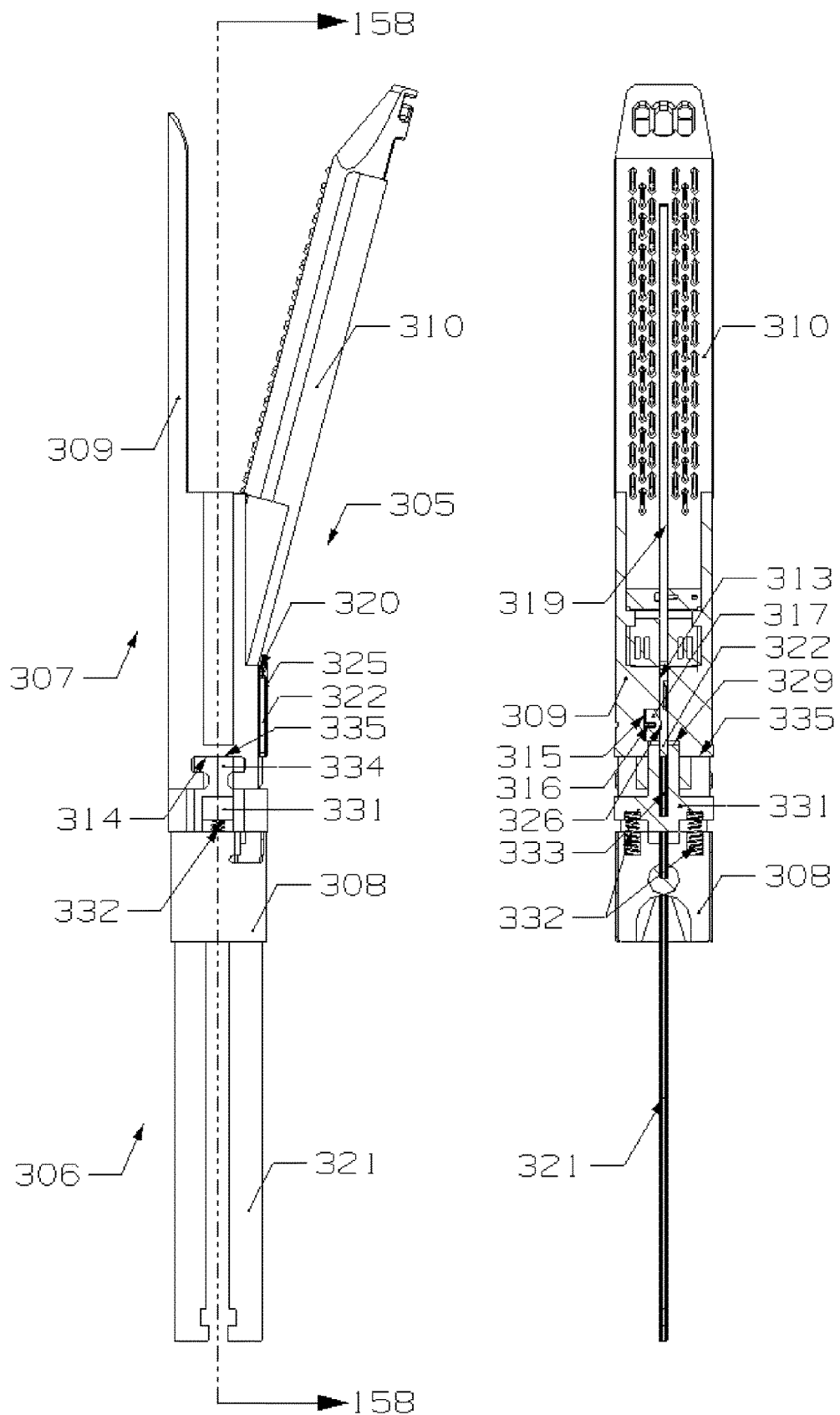
Figure 159:
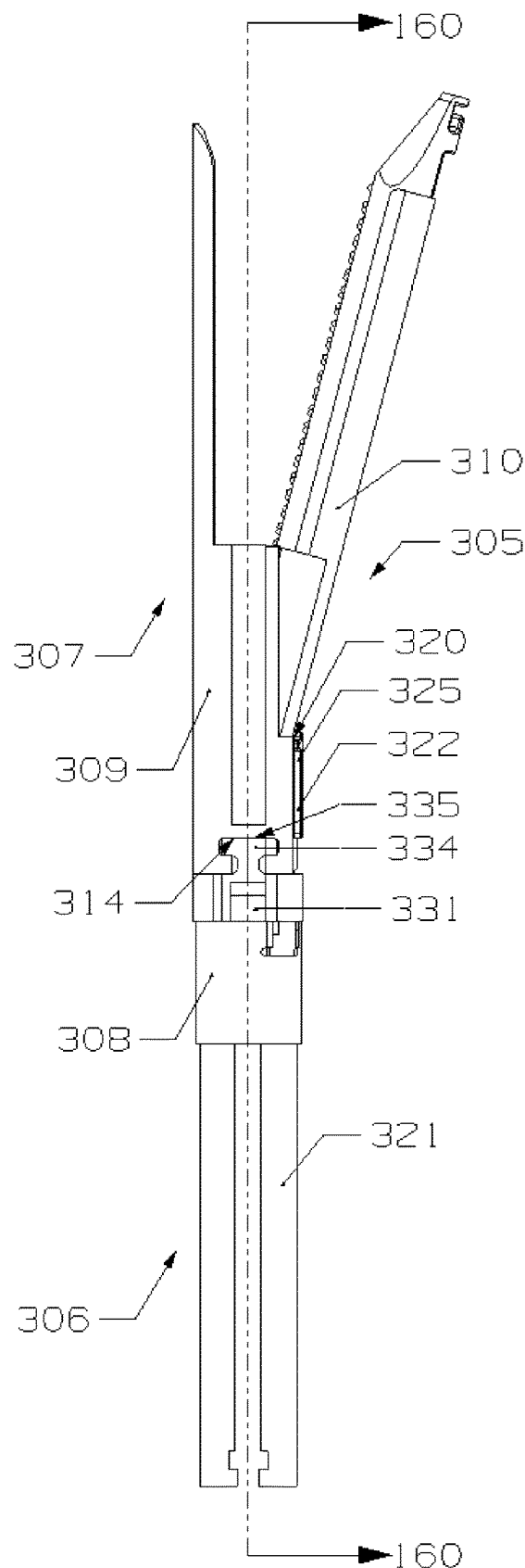
Figure 160:
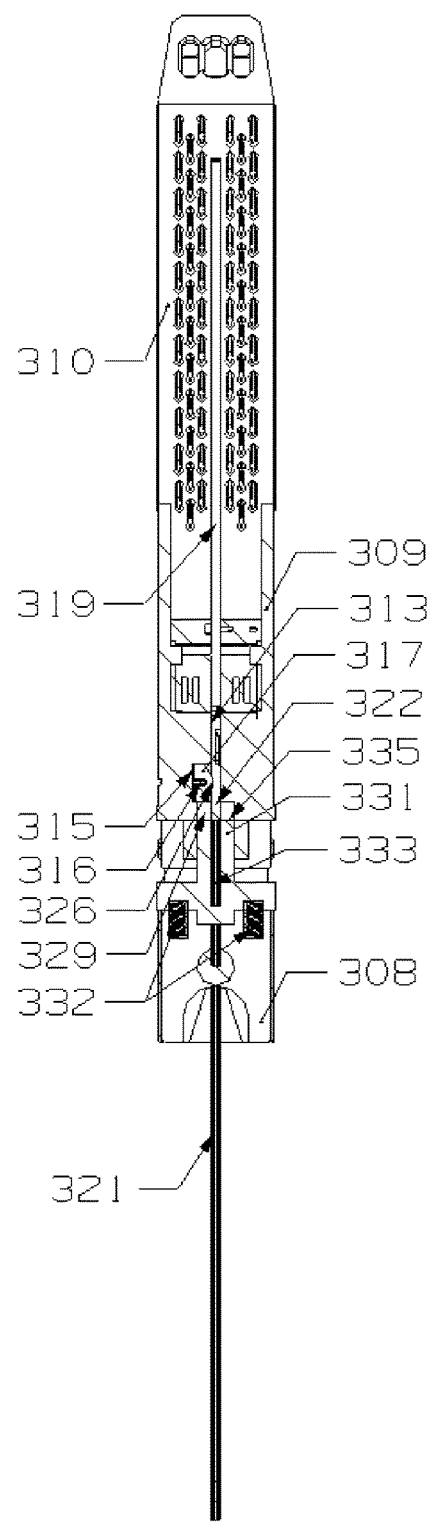
Figure 161:
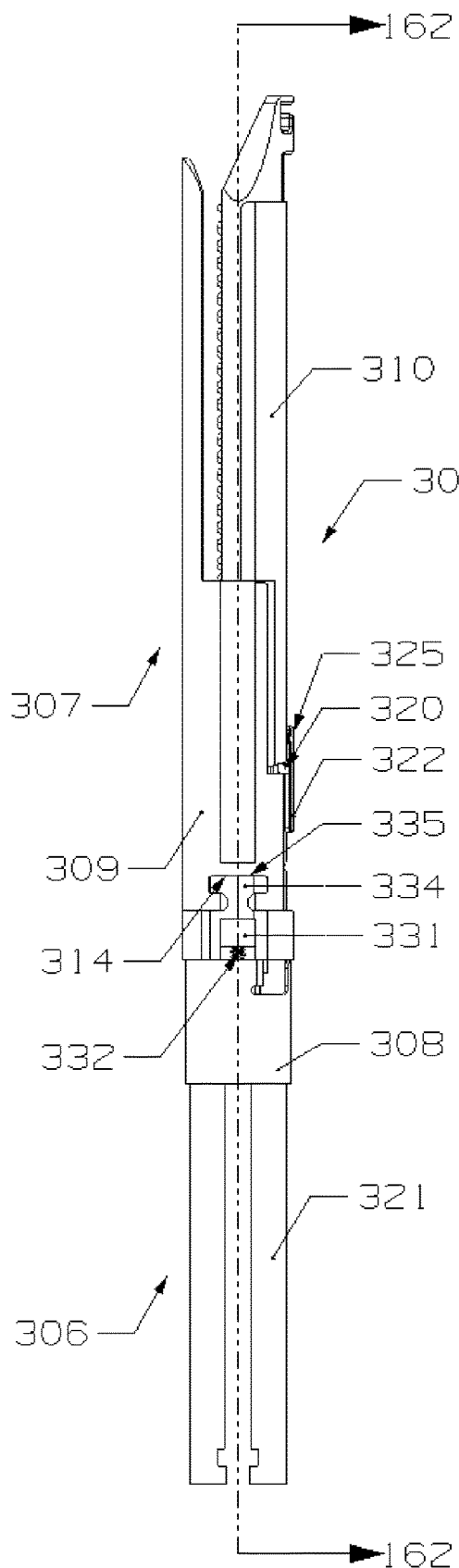
Figure 162:
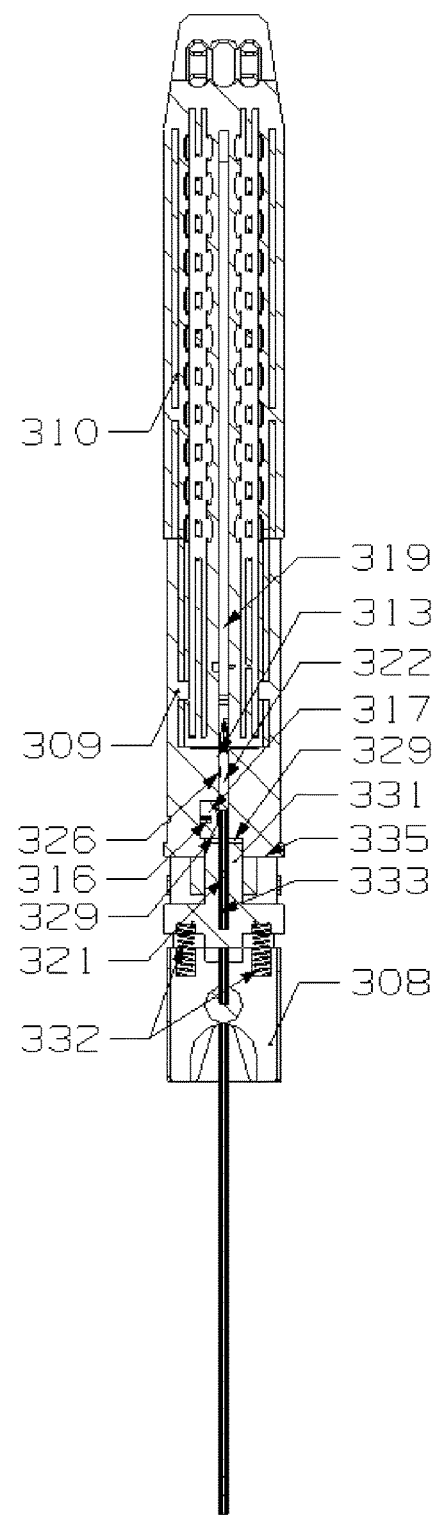
Figure 163:
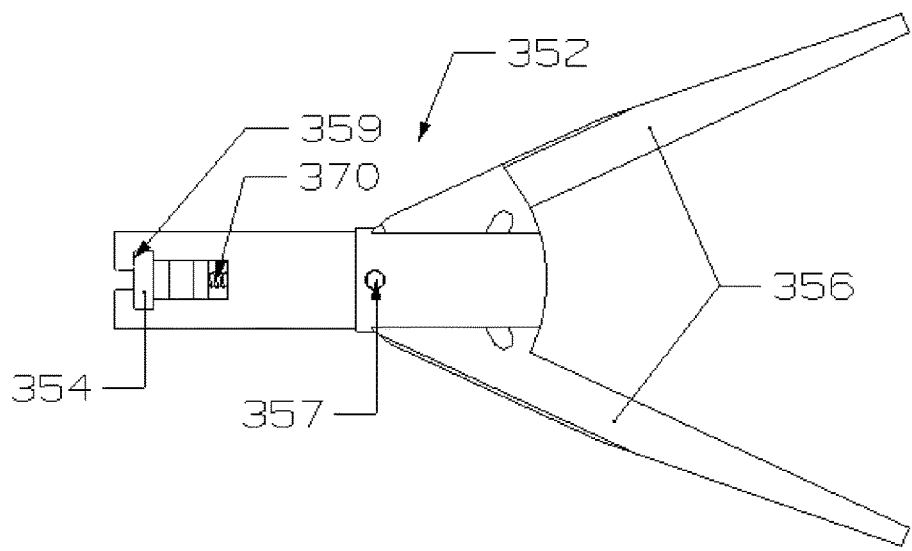
Figure 164:
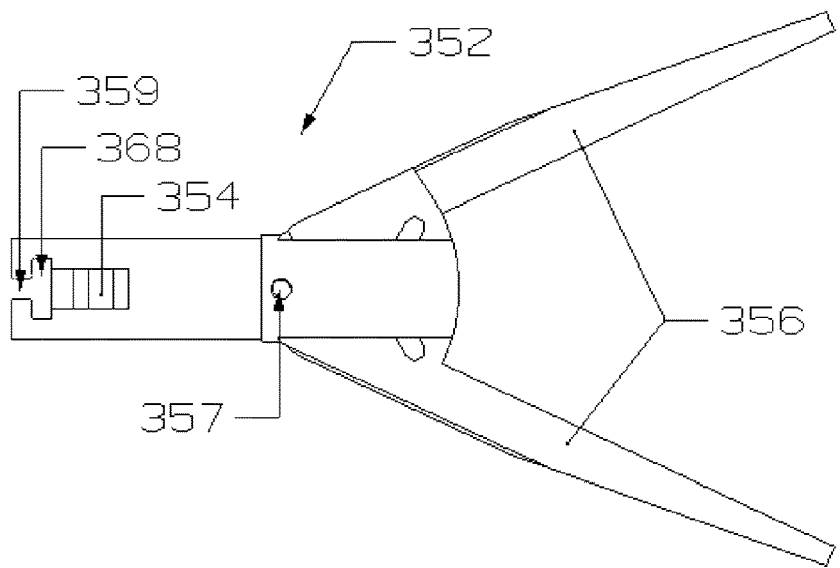
Figure 165:
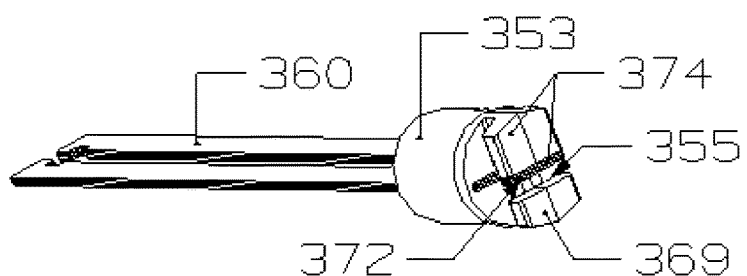
Figure 166:
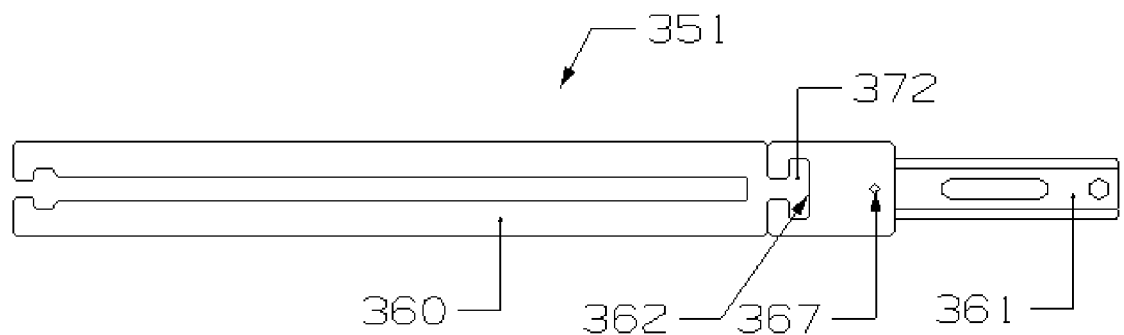
Figure 167:
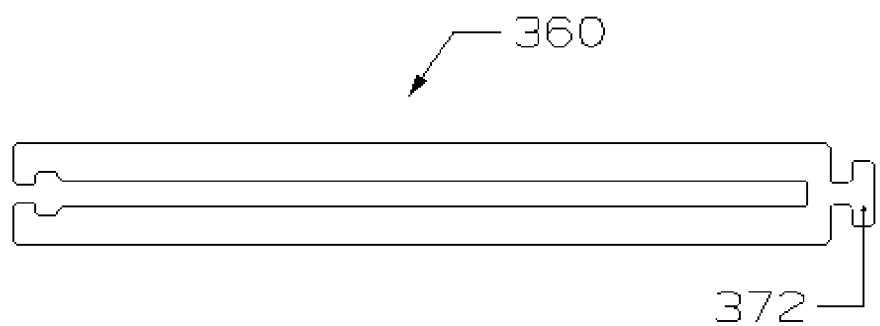
Figure 168:
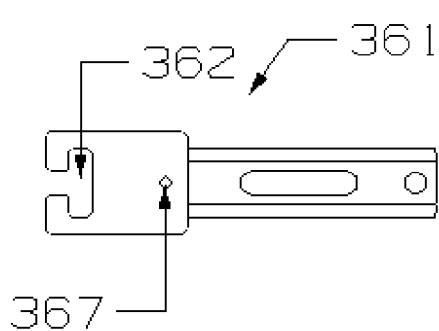
Figure 169:
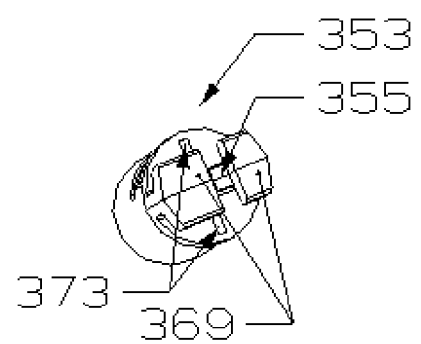

FIG. 131 is a perspective view of the driving member in FIG. 130;

FIG. 132 is a perspective view showing the curved replaceable anvil in FIG. 130;

FIG. 133 is a perspective view showing that the locating elastic part is mounted in the curved replaceable anvil of FIG. 132;

FIG. 134 is a perspective view showing that the curved driving head is inserted into the curved replaceable anvil of FIG. 133;

FIG. 135 is a perspective view showing that the curved replaceable anvil and the driving head are inserted into the driving bar and the tool holder;

FIG. 136 is a perspective view showing that the curved staple cartridge is inserted into the curved replaceable anvil of FIG. 135;

FIG. 137 is a perspective view showing the curved staple cartridge in FIG. 136;

FIG. 138 is a perspective view showing the back of the curved staple cartridge of FIG. 137;

FIG. 139 is a perspective view showing the closed state between the curved staple cartridge and the curved replaceable anvil of FIG. 130;

FIG. 140 is an enlarged perspective view showing the curved driving head, the knife and the locating elastic part;

FIG. 141 is an enlarged perspective view of the curved driving head and knife in FIG. 140;

FIG. 142 is a perspective view showing that the driving bar is mounted in the interchangeable tool according to the eleventh embodiment of the present disclosure;

FIG. 143 is a perspective view showing that the locating elastic part is mounted in the straight replaceable anvil;

FIG. 144 is a perspective view showing the straight replaceable anvil in FIG. 143;

FIG. 145 is a perspective view of the straight driving head in FIG. 142;

FIG. 146 is a perspective view showing the locating elastic part in FIG. 142;

FIG. 147 is a front view of the knife in FIG. 145;

FIG. 148 is a perspective view showing the straight staple cartridge in FIG. 142;

FIG. 149 is a perspective view showing that the driving bar, the locking block and locking spring are mounted in the tool holder;

FIG. 150 is a perspective view showing that some parts of the tool holder of FIG. 149 are removed;

FIG. 151 is a perspective view showing that the locking block in FIG. 149 exits the locking groove;

FIG. 152 is a perspective view showing that some parts of the tool holder of FIG. 151 are removed;

FIG. 153 is a perspective view showing the tool holder;

FIG. 154 is a perspective view showing the locking block and the locking spring;

FIG. 155 is a front view of the driving bar in FIG. 149;

FIG. 156 is a front view of the driving member;

FIG. 157 is a front view showing that the interchangeable tool and the driving head are mounted on the tool holder and the driving bar;

FIG. 158 is a section view of the 158-158 profile of FIG. 157;

FIG. 159 is a front view showing that the interchangeable tool and the driving head are mounted on the tool holder and the driving bar;

FIG. 160 is a section view of the 160-160 profile of FIG. 159;

FIG. 161 is a front view showing the closed state between the straight staple cartridge and the straight replaceable anvil in FIG. 157;

FIG. 162 is a section view of the 162-162 profile of FIG. 161;

FIG. 163 is a front view showing that the driving head is mounted in the interchangeable tool according to the twelfth embodiment of the present disclosure;

FIG. 164 is a front view showing that the locking block of FIG. 163 exits the locking groove;

FIG. 165 is a perspective view showing that the driving bar is mounted in the tool holder;

FIG. 166 is a front view of the driving member;

FIG. 167 is a front view of the driving bar in FIG. 166;

FIG. 168 is a front view of the driving head in FIG. 166;

FIG. 169 is a perspective view of the tool holder in FIG. 165;

FIG. 170 is a front view showing that a tool inlay connection is formed between the tool holder and the interchangeable tool, and a driving head inlay connection is formed between the driving bar and the driving head.

Figure 172:
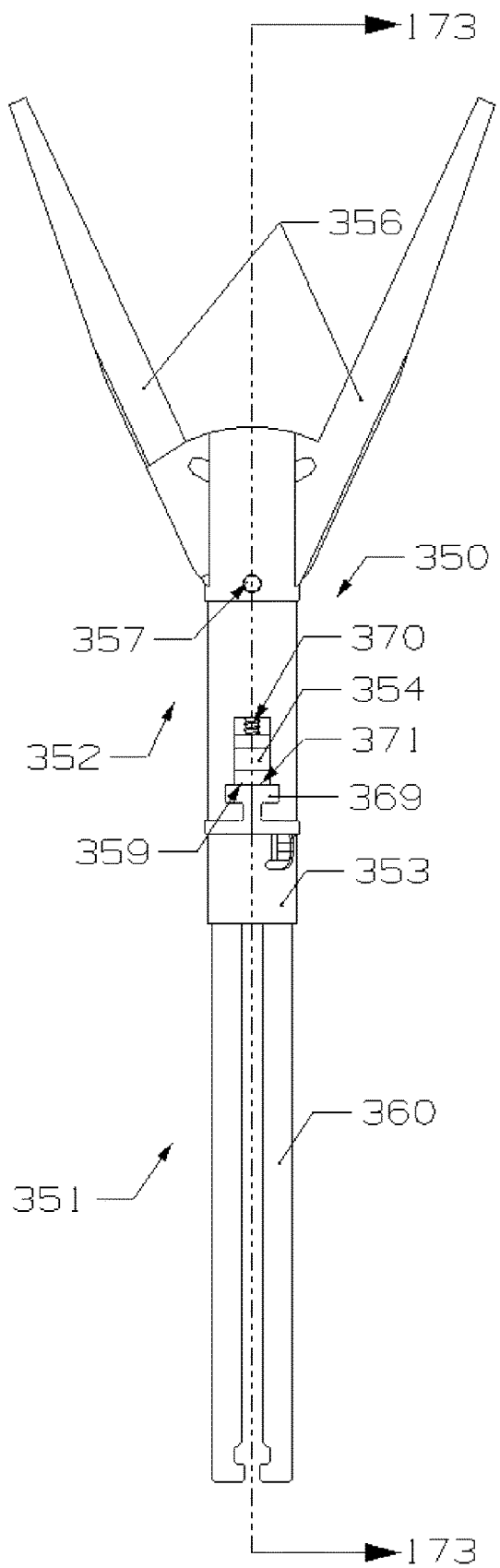
Figure 173:
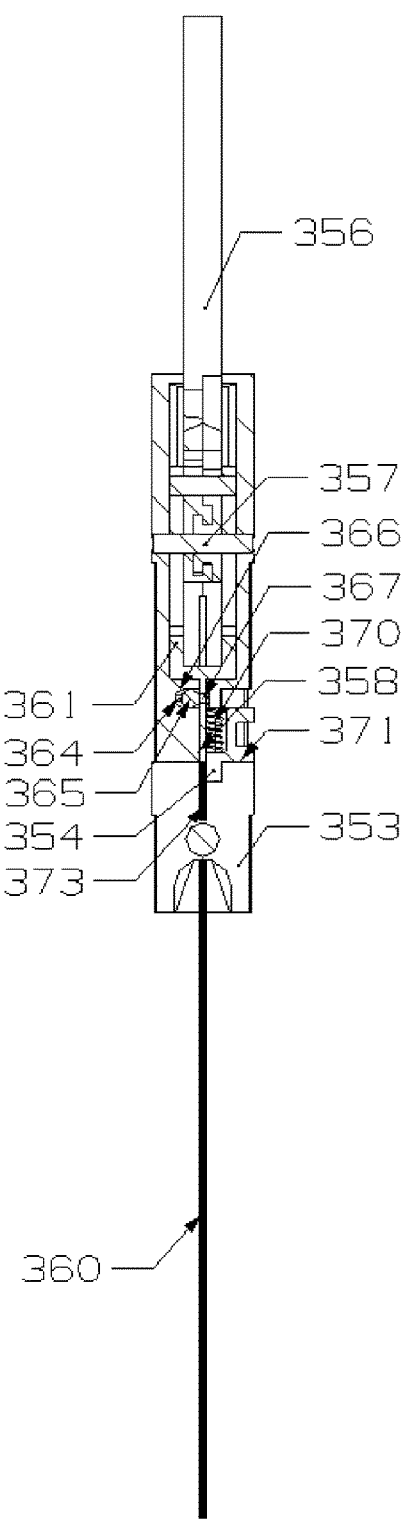
Figures 174, 175:
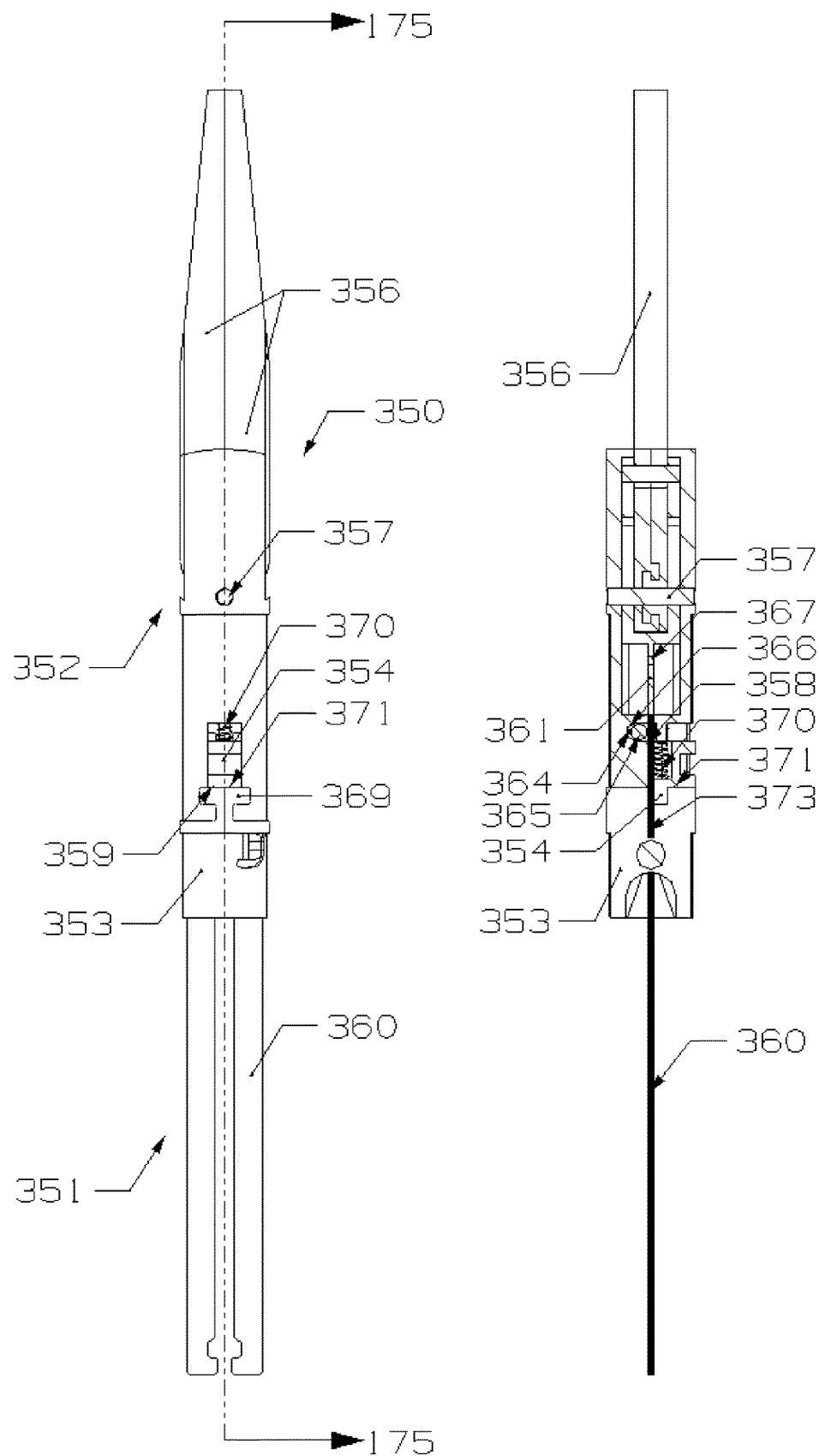
Figure 176:
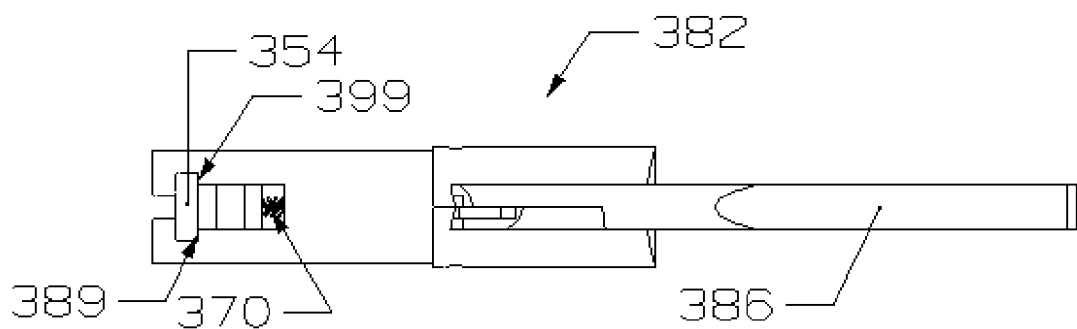
Figure 177:
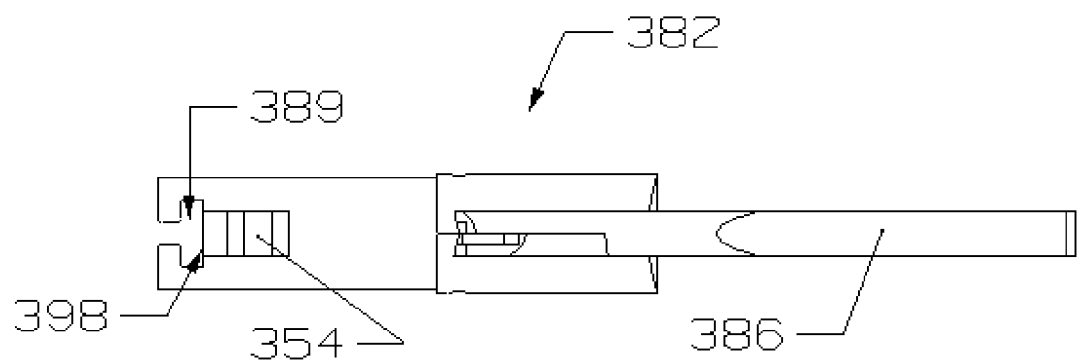
Figure 178:
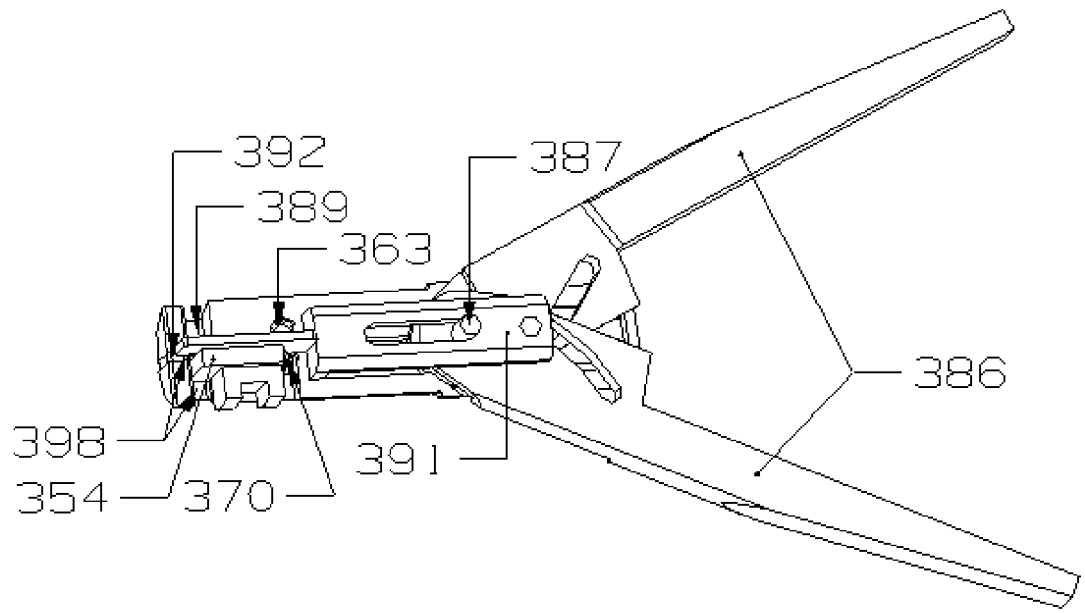
Figure 181:
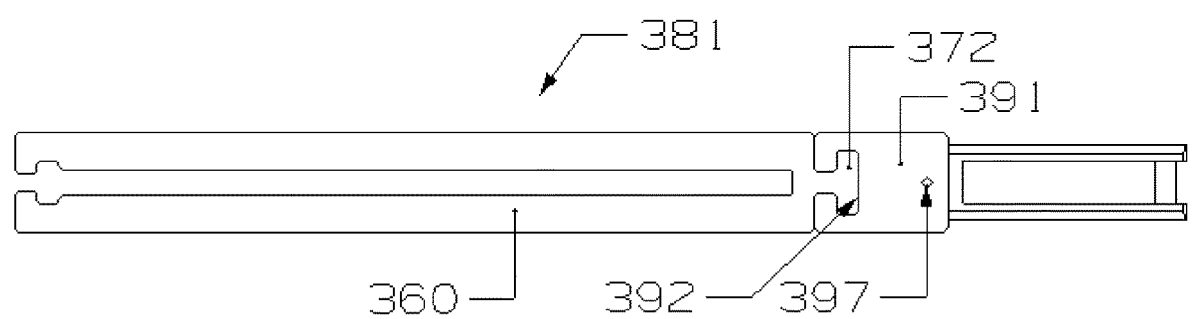
Figure 182:
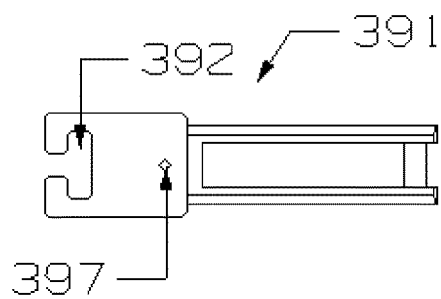
Figure 183:
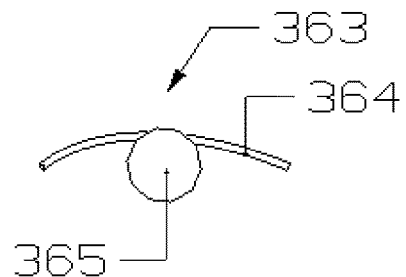

FIG. 171 is a section view of the 171-171 profile of FIG. 170;

FIG. 172 is a front view showing that the interchangeable tool is mounted on the tool holder and the driving head is mounted on the driving bar;

FIG. 173 is a section view of the 173-173 profile of FIG. 172;

FIG. 174 is a front view showing that the driving member of FIG. 172 is moved forward;

FIG. 175 is a section view of the 175-175 profile of FIG. 174;

FIG. 176 is a front view showing that the driving head is mounted in the interchangeable tool according to the thirteenth embodiment of the present disclosure;

FIG. 177 is a front view showing that the locking block of FIG. 176 exits the locking groove;

FIG. 178 is a perspective view showing that some parts are removed from the replaceable part of FIG. 176;

FIG. 179 is a front view showing that the interchangeable tool is mounted on the tool holder, and the driving head is mounted on the driving bar;

FIG. 180 is a section view of the 180-180 profile of FIG. 179;

FIG. 181 is a front view of the driving member in FIG. 179;

FIG. 182 is a front view of the driving head in FIG. 181;

FIG. 183 is an enlarged perspective view showing the locating elastic part in FIG. 179.

DETAILED DESCRIPTION OF THE PREFERRED EMBODIMENTS

The preferred embodiments of the multipurpose endoscopic surgical instrument of the present disclosure are described below by way of examples and with reference to the accompanying drawings. The scope of the present disclosure will be indicated in the claims. It should be recognized that some or all of the accompanying drawings are diagrams for illustrating a preferred embodiment of the present disclosure and do not depict the actual dimensions of the illustrated parts. With reference to the detailed description of the preferred embodiment, a clearer understanding of the means of implementation for achieving the above and other purposes and advantages of the present disclosure will be obtained. In the drawings and the following description, the term "back" refers to the position near the operator of the endoscopic surgical instrument, and the term "front" refers to the position away from the operator of the endoscopic surgical instrument; the term "up" means above the operator of the endoscopic surgical instrument, and the term "down" means below the operator of the endoscopic surgical instrument; the term "left" refers to the left side of the operator of the endoscopic surgical instrument, and the term "right" refers to the right side of the operator of the endoscopic surgical instrument. Terms for other positions and directions can be understood from the accompanying drawings and descriptions below. To emphasize the figures and descriptions of the multipurpose endoscopic surgical instrument and related components of the present disclosure, other components in the accompanying drawings are not described in detail. Regarding the structure, installation, purpose and operation process of various components of the endoscopic surgical instrument, referring to various patents cited in this specification and related other relevant documents.

Figure 1:
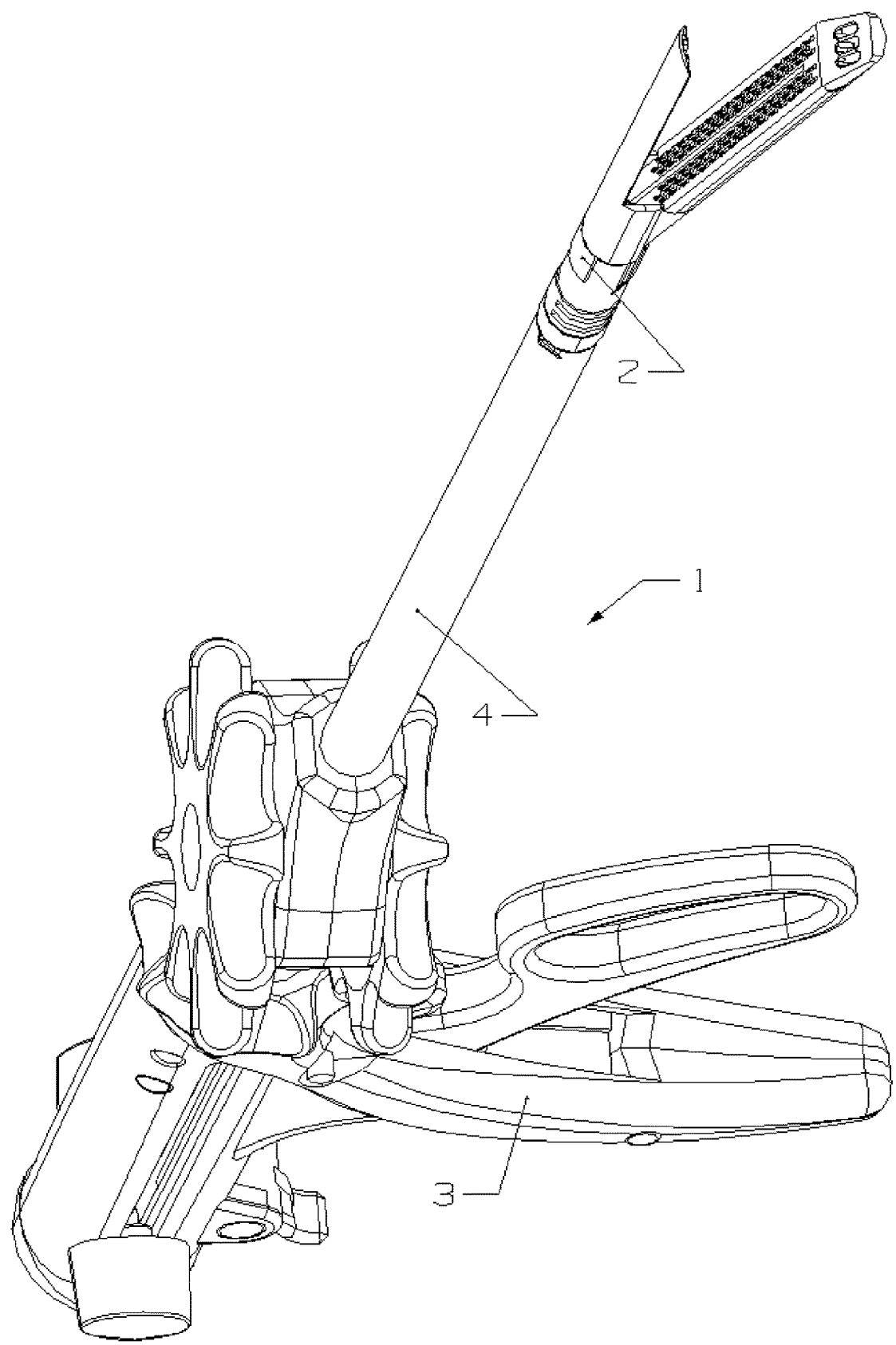
FIG. 1 is a perspective view of a manual multipurpose endoscopic surgical instrument according to the present disclosure.

FIG. 1 illustrates a manual multipurpose endoscopic surgical instrument 1 according to the present disclosure. The endoscopic surgical instrument 1 includes a tool assembly 2, a manual operation assembly 3 and an elongated body 4. The elongated body 4 connects the operation assembly 3 and the tool assembly 2.

Figure 2:
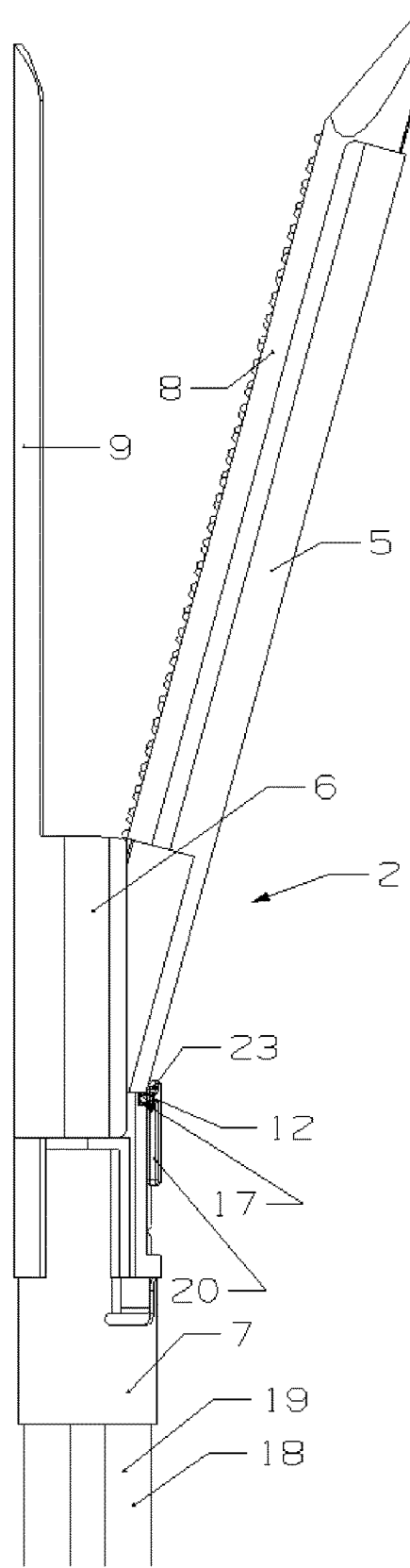
FIG. 2 is a front view of a tool assembly and a driving member according to the first embodiment of the present disclosure.
Figure 3:
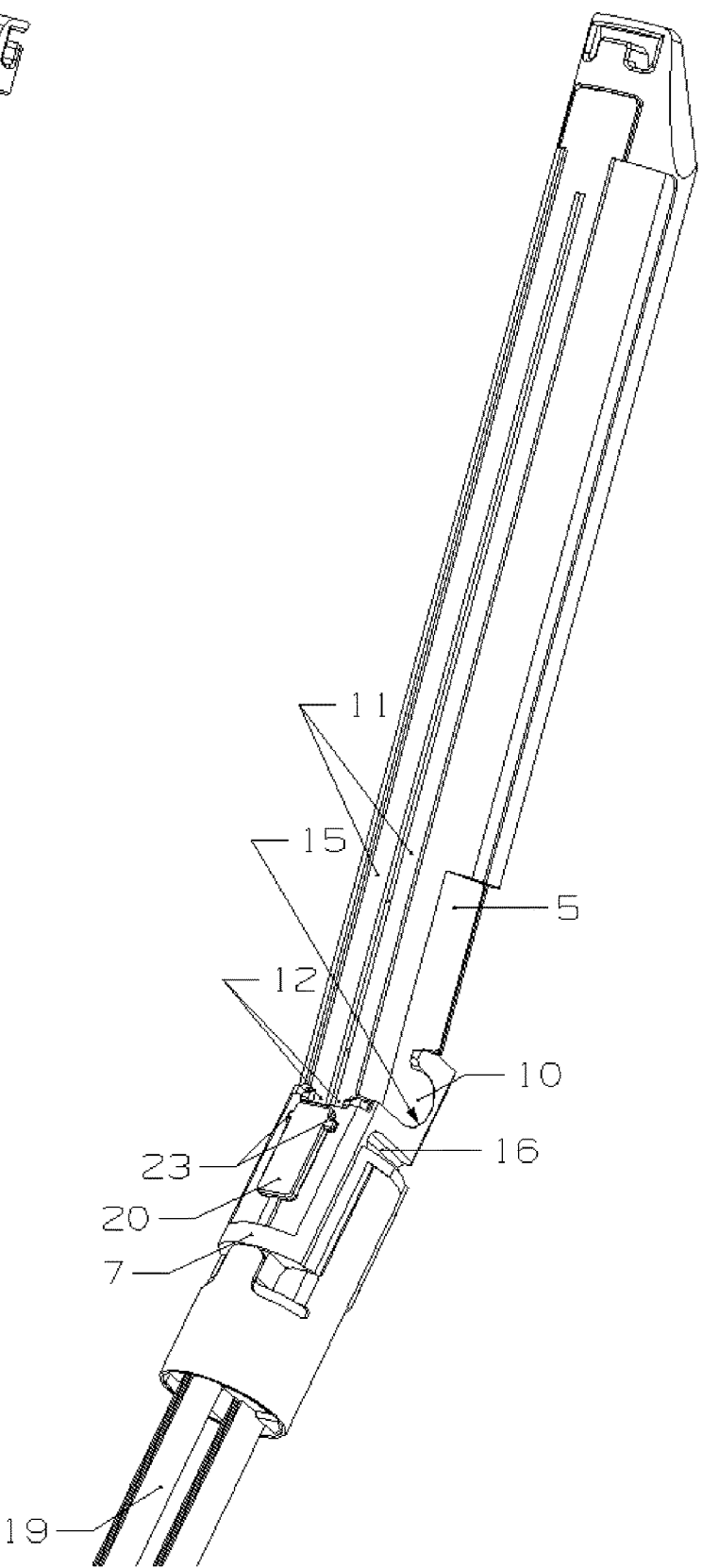
FIG. 3 is a perspective view showing a state in which a first interchangeable tool may be inserted on or removed from a tool holder of FIG. 2.
Figure 5:
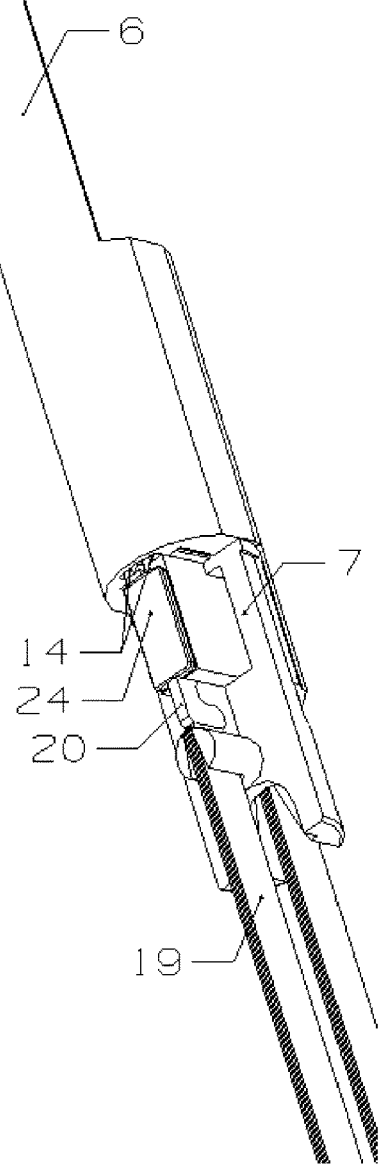
FIG. 5 is a perspective view showing a state in which a second interchangeable tool may be inserted on or removed from the tool holder (some parts are removed) of FIG. 2.
Figure 6:
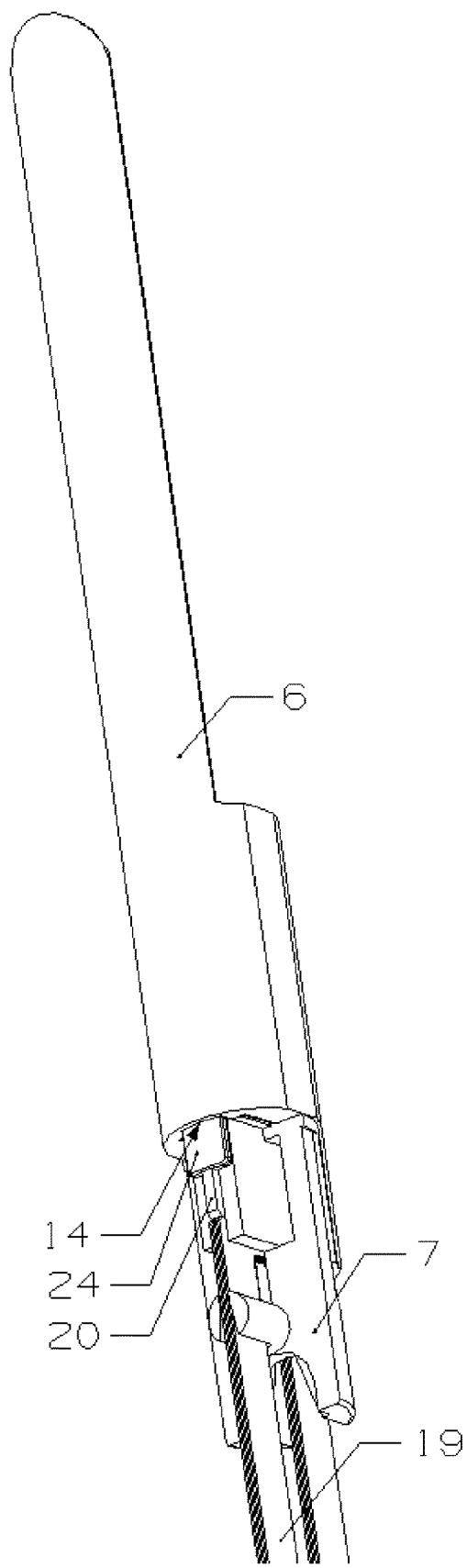
FIG. 6 is a perspective view showing that the second interchangeable tool of FIG. 2 is mounted on the tool holder (some parts are removed)
Figure 7:
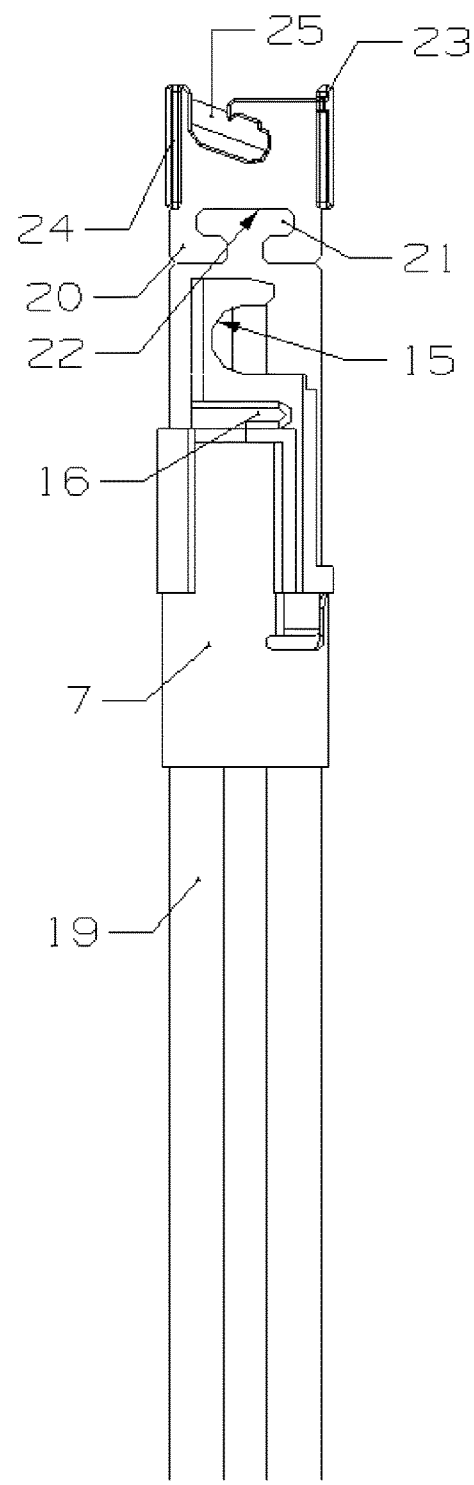
FIG. 7 is a front view showing that a driving head of FIG. 2 extends out of the tool holder.
Figure 8:
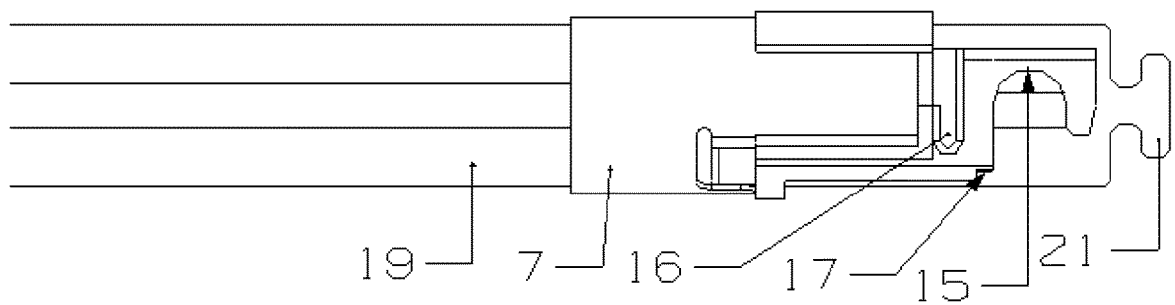
FIG. 8 is a front view showing that the driving head of FIG. 7 is removed from the driving bar.
Figure 9:
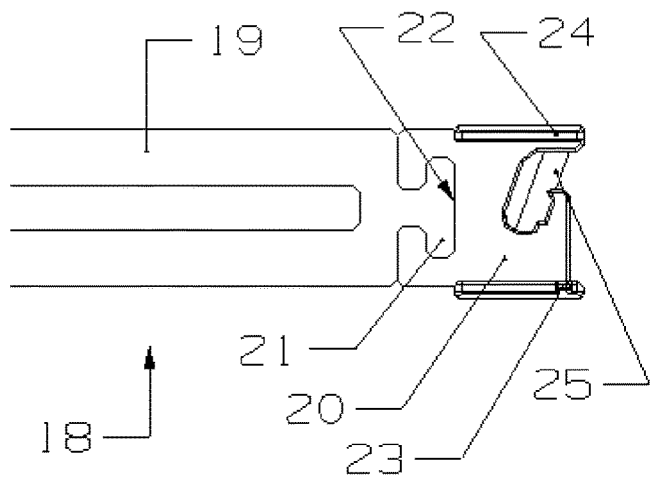
FIG. 9 is a partial front view of the driving member of FIG. 2.
Figure 10:
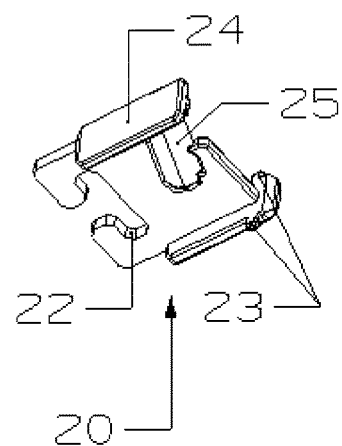
FIG. 10 is a perspective view of the in-use driving head or spare driving head of FIG. 9.
Figure 11:
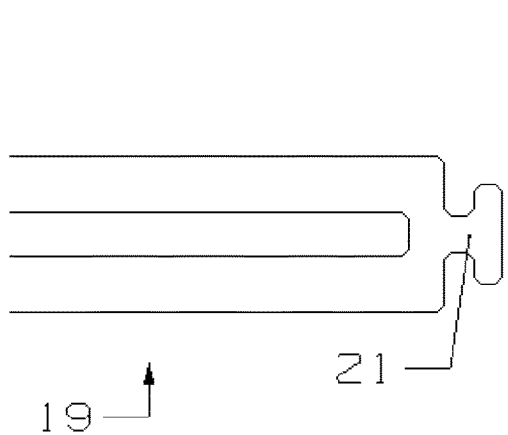
FIG. 11 is a partial front view of the driving bar of FIG. 9.
Figure 12:
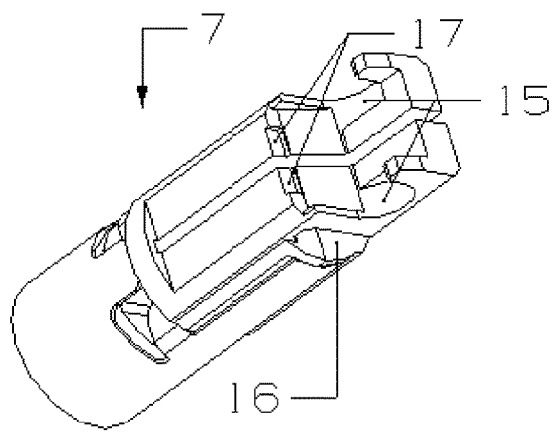
FIG. 12 is a perspective view showing the tool holder of FIG. 2.
Figure 13:
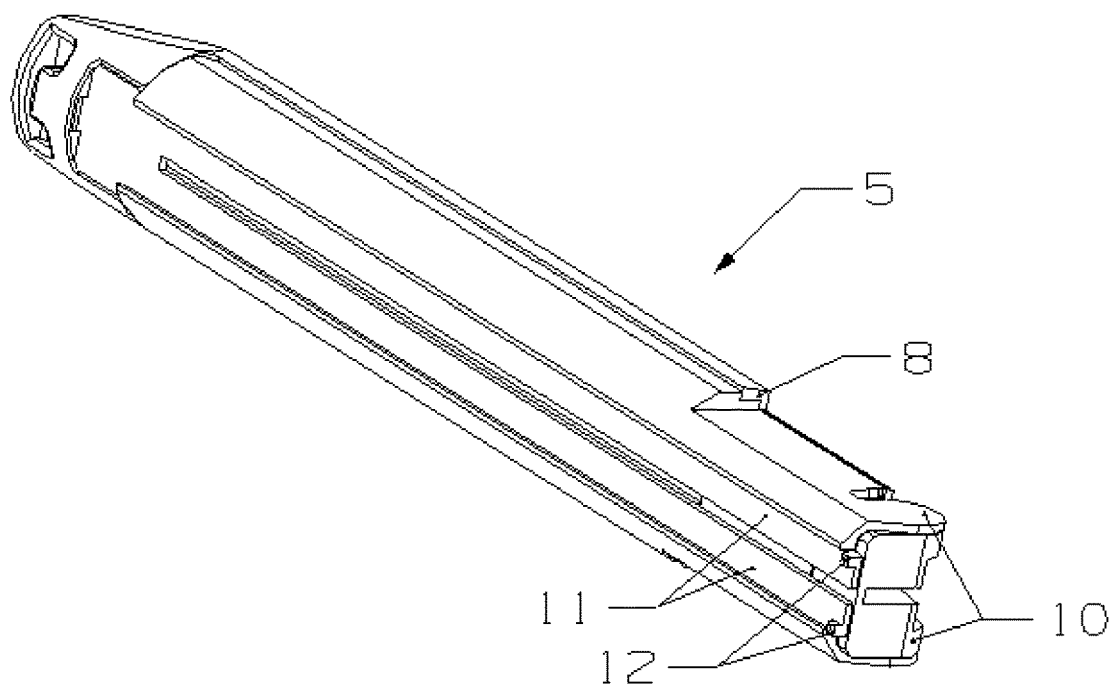
FIG. 13 is a perspective view showing the first interchangeable tool of FIG. 2.
Figure 14:
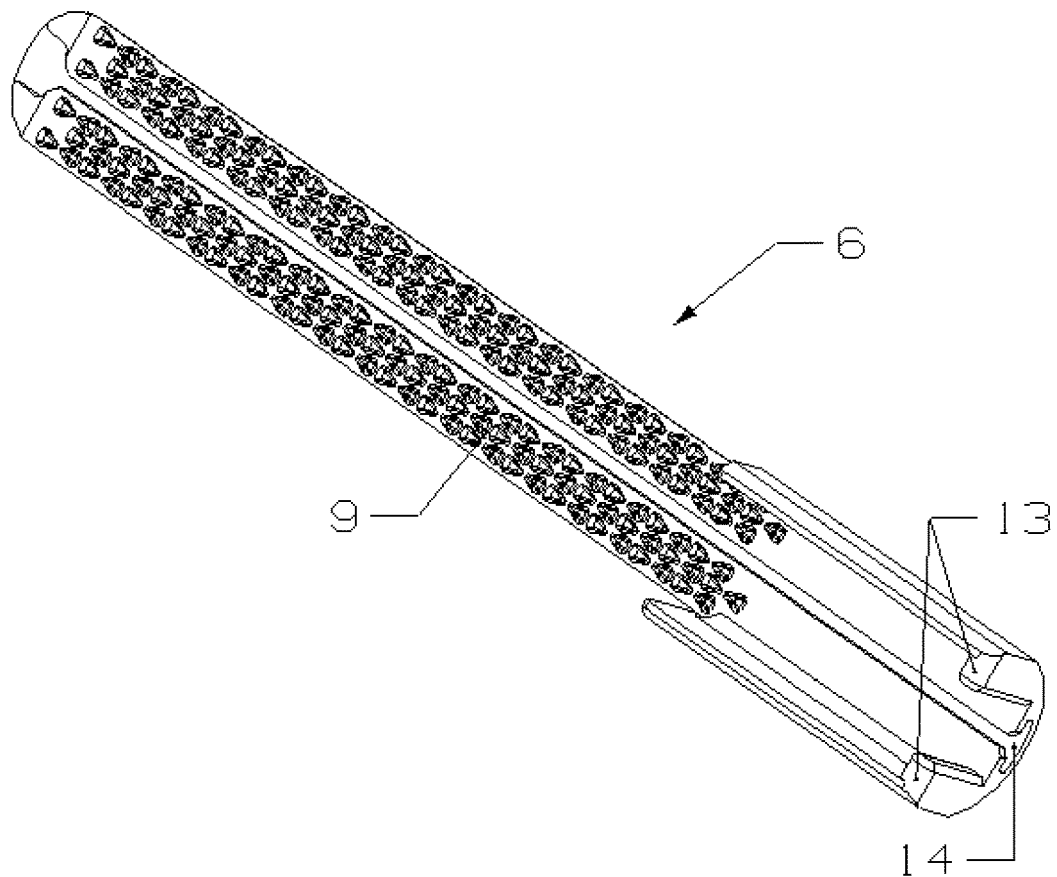
FIG. 14 is a perspective view showing the second interchangeable tool of FIG. 2.

FIGS. 2-14 illustrate the tool assembly 2 and a driving member 18 according to the first embodiment. The tool assembly 2 includes a first interchangeable tool 5, a second interchangeable tool 6 and a tool holder 7 (see FIG. 2). The first interchangeable tool 5 includes a staple cartridge 8. The second interchangeable tool 6 includes an anvil 9. The first interchangeable tool 5 includes a first mounting key 10, a first tool slot 11 in a forward-backward direction and a constraining key 12 (see FIG. 13). The second interchangeable tool 6 includes a second mounting key 13 and a second tool slot 14 in a forward-backward direction (see FIG. 14). The tool holder 7 includes a first open-end mounting groove 15, a second open-end mounting groove 16 and an opening constraining groove 17 (see FIG. 12). The first mounting key 10 is inserted into the first open-end mounting groove 15 between the tool holder 7 and the first interchangeable tool 5 to form a rotating support of the first interchangeable tool 5 (see FIG. 3 and FIG. 4). The first interchangeable tool 5 may rotate within a limited angle around the rotating support of the first interchangeable tool 5, so that the first interchangeable tool 5 rotates between an open state and a closed state. The second interchangeable tool 6 and the tool holder 7 are connected with each other by inserting the second mounting key 13 into the second open-end mounting groove 16. The operation assembly 3 includes a driving member 18. The operation assembly 3 controls the driving member 18 to move forward and backward in the tool assembly 2. The driving member 18 includes a driving bar 19 and a driving head 20 (see FIGS. 9-11). An inlay key 21 is inserted into an inlay groove 22 between the driving bar 19 and the driving head 20 to form a driving head inlay connection. The driving head 20 includes a first inserting block 23, a second inserting block 24 and a knife 25. The first inserting block 23 is located at the opening of the constraining groove 17 (see FIG. 2, FIG. 4 and FIG. 4A). The first inserting block 23 may move back and forth along the first tool slot 11 of the first interchangeable tool 5. The second inserting block 24 may move back and forth along the second tool slot 14 of the second interchangeable tool 6. (see FIG. 5 and FIG. 6). The operation assembly 3 controls the actions of the first interchangeable tool 5 and the second interchangeable tool 6 in the tool assembly 2 through the driving member 18.

Figure 4:
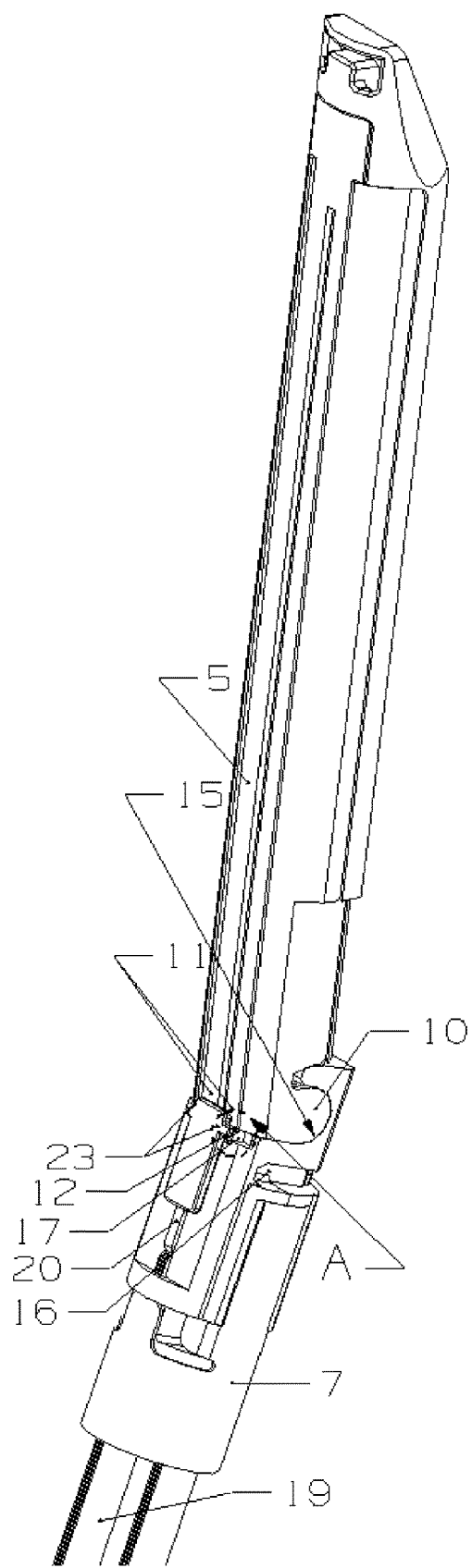
FIG. 4 is a perspective view showing that the first interchangeable tool of FIG. 2 is mounted on the tool holder.
Figure 4A:
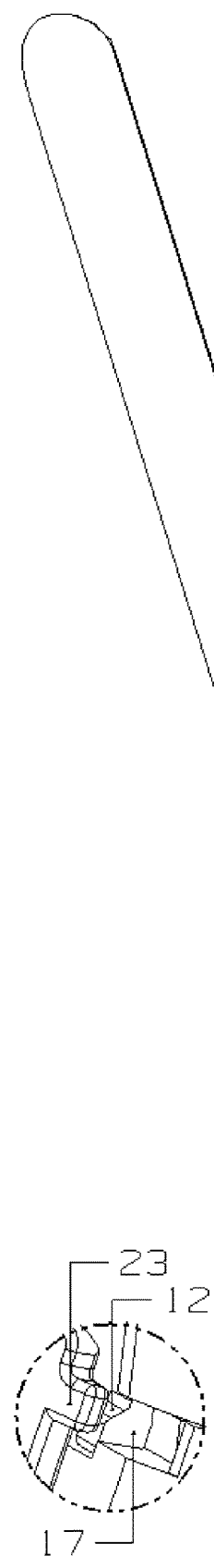
FIG. 4A is an enlarged partial view of region A of FIG. 4.

During the process of mounting the first interchangeable tool 5 to the tool holder 7, step 1, the operation assembly 3 controls the first inserting block 23 on the driving head 20 on the driving bar 19 to move backwards to open the opening of the constraining groove 17; step 2, the first mounting key 10 and the constraining key 12 are inserted into the first mounting groove 15 and the constraining groove 17 through the openings of the first mounting groove 15 and the constraining groove 17, and the first interchangeable tool 5 is inserted on the tool holder 7 (see FIG. 3 and FIG. 4); step 3, the operation assembly 3 controls the first inserting block 23 on the driving head 20 on the driving bar 19 to move forwards and insert into the first tool slot 11 of the first interchangeable tool 5, so as to close the opening of the constraining groove 15 on the tool holder 7, such that the first inserting block 23 prevents the first mounting key 10 and the constraining key 12 from moving out of the openings of the first mounting groove 15 and the constraining groove 17, and the first interchangeable tool 5 is mounted on the tool holder 7 (see FIG. 4 and FIG. 4A). During the process of mounting the second interchangeable tool 6 to the tool holder 7, step 1, the operation assembly 3 controls the second inserting block 24 on the driving head 20 on the driving bar 19 to move backwards; step 2, the second mounting key 13 is inserted into the second mounting groove 16 through the opening of the second mounting groove 16, and the second interchangeable tool 6 is inserted on the tool holder 7 (see FIG. 5, FIG. 12 and FIG. 14); step 3, the operation assembly 3 controls the second inserting block 24 on the driving head 20 on the driving bar 19 to move forwards and insert into the second tool slot 14 of the second interchangeable tool 6, such that the second inserting block 24 prevents the second mounting key 13 from moving out of the opening of the second mounting groove 16, and the second interchangeable tool 6 is mounted on the tool holder 7 (see FIG. 6). During the process of removing the first interchangeable tool 5 from the tool holder 7, step 1, the operation assembly 3 controls the first inserting block 23 on the driving head 20 on the driving bar 19 to move backwards to exit the first tool slot 11 of the first interchangeable tool 5, so as to open the opening of constraining groove 17 (see FIG. 3 and FIG. 4); step 2, the first mounting key 10 and the constraining key 12 are removed from the first mounting groove 15 and the constraining groove 17, then the first interchangeable tool 5 can be removed from the tool holder 7. During the process of removing the second interchangeable tool 6 from the tool holder 7, step 1, the operation assembly 3 controls the second inserting block 24 on the driving head 20 on the driving bar 19 to move backwards to exit the second tool slot 14 of the second interchangeable tool 6 (see FIG. 5); step 2, the second mounting key 13 is removed from the second mounting groove 16, then the second interchangeable tool 6 can be removed from the tool holder 7.

When the operation assembly 3 controls the first inserting block 23 on the driving head 20 on the driving bar 19 to move forwards at the back part of the first tool slot 11 of the first interchangeable tool 5, the first inserting block 23 on the driving head 20 drives the first interchangeable tool 5 to rotate towards the closing direction. When the operation assembly 3 controls the first inserting block 23 on the driving head 20 on the driving bar 19 to move backwards at the back part of the first tool slot 11 of the first interchangeable tool 5, the first inserting block 23 on the driving head 20 on the driving bar 19 drives the constraining key 12 to rotate the first interchangeable tool 5 towards the opening direction (see FIG. 4 and FIG. 4A). When the first inserting block 23 on the driving head 20 on the driving bar 19 moves to the middle front part of the first tool slot 11 of the first interchangeable tool 5, the first interchangeable tool 5 and the second interchangeable tool 6 are kept in a closed state.

The staple cartridge 8 in the first interchangeable tool 5, the anvil 9 in the second interchangeable tool 6 and the knife 25 on the driving head 20 are used to cut and staple tissue. When using the endoscopic surgical instrument 1, if the knife 25 on the driving head 20 is found to be damaged, a spare driving head 20 may be selected to replace the driving head 20 in use. During the process of replacing the driving head 20, step 1, the operation assembly 3 controls the in-use driving head 20 on the driving bar 19 to move backward, and the first interchangeable tool 5 and the second interchangeable tool 6 are removed from the tool holder 7 respectively; step 2, the operation assembly 3 controls the in-use driving head 20 on the driving bar 19 to move forward until the in-use driving head 20 extends out of the tool holder 7 (see FIG. 7), the inlay key 21 is removed from the inlay groove 22, then the in-use driving head 20 could be removed from the driving bar 19 (see FIG. 8); step 3, the inlay key 21 is inserted into the inlay groove 22 between the driving bar 19 and the spare driving head 20 to form a driving head inlay connection, and the spare driving head 20 can be installed on the driving bar 19 (see FIG. 7); step 4, the operation assembly 3 controls the spare driving head 20 on the driving bar 19 to move backward until the spare driving head 20 returns to the tool holder 7; step 5, the first interchangeable tool 5 and the second interchangeable tool 6 are installed on the tool holder 7, respectively (see FIG. 2).

After the endoscopic surgical instrument 1 is used, according to the requirements of endoscopic surgery, a first interchangeable tool with the same anastomotic length and the same anastomotic thickness as the first interchangeable tool 5 may be replaced and installed on the tool holder 7. A first interchangeable tool with the same anastomotic length but different anastomotic thickness as the first interchangeable tool 5 may also be replaced and installed on the tool holder 7. A first interchangeable tool with the same anastomotic thickness as the first interchangeable tool 5 but with a shorter anastomotic length than that of the second interchangeable tool 6 may also be replaced and installed on the tool holder 7. A first interchangeable tool with a different anastomotic thickness from that of the first interchangeable tool 5 but with a shorter anastomotic length than that of the second interchangeable tool 6 may also be replaced and installed on the tool holder 7. A second interchangeable tool with an anastomotic length different from that of the second interchangeable tool 6 may be replaced, then a corresponding first interchangeable tool is installed. According to the requirements of endoscopic surgery, tools with other functions may also be replaced or used.

Figure 17:
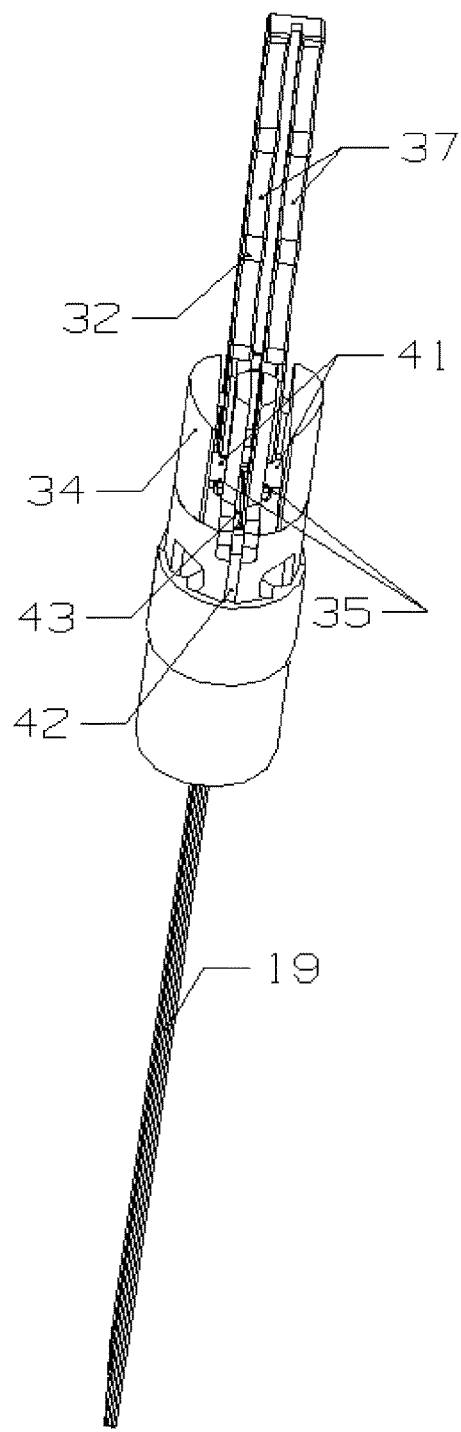
FIG. 17 is a perspective view showing the back of the position of FIG. 16.
Figure 18:
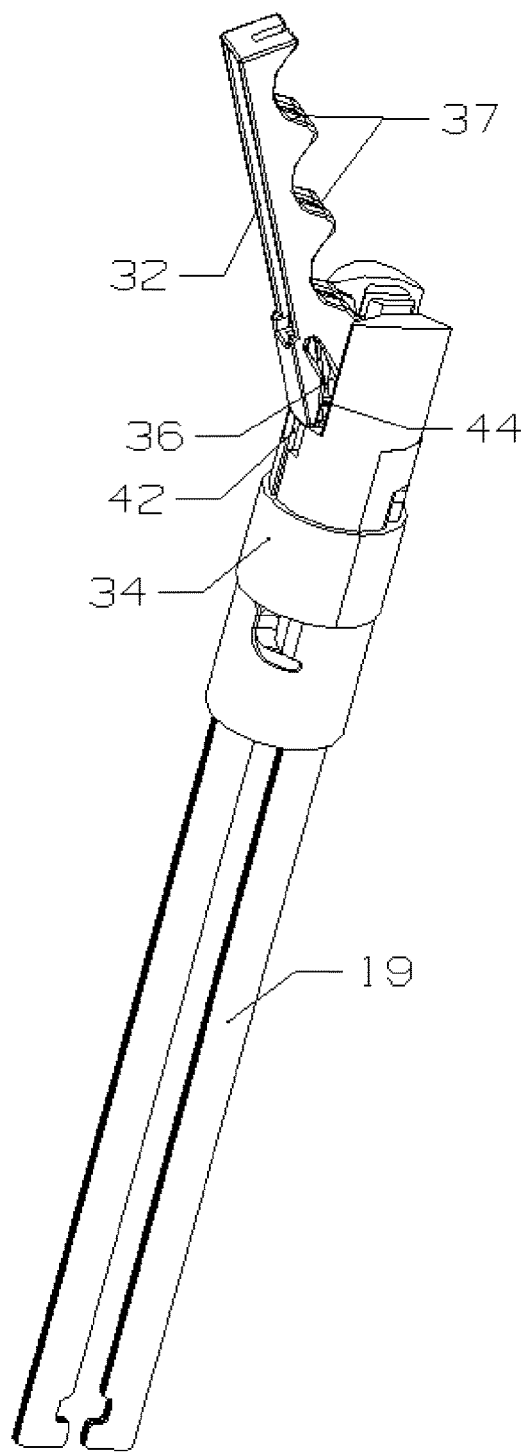
FIG. 18 is a perspective view showing that the first interchangeable tool of FIG. 15 is mounted on the tool holder.
Figure 21:
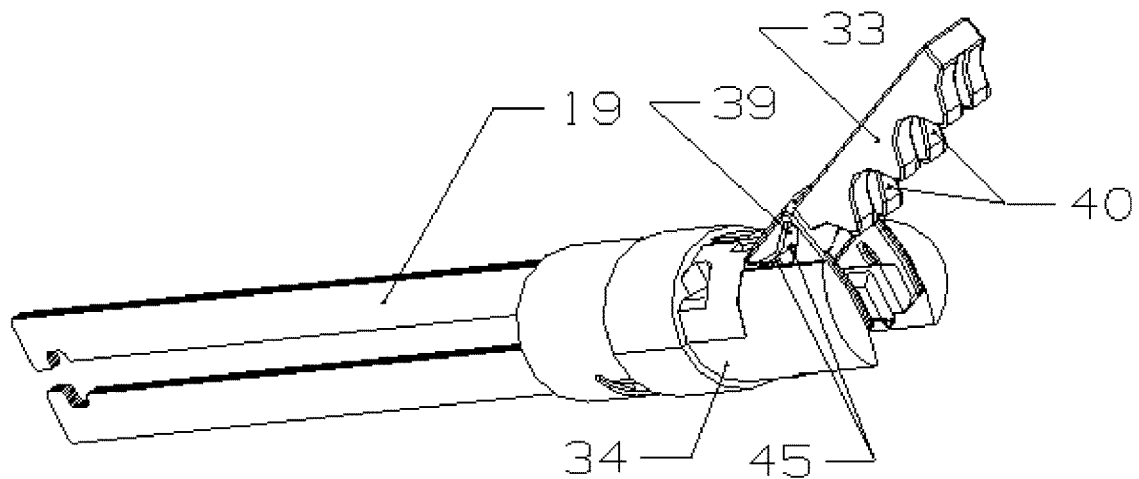
FIG. 21 is a perspective view showing that the second interchangeable tool of FIG. 15 is mounted on the tool holder.
Figure 22:
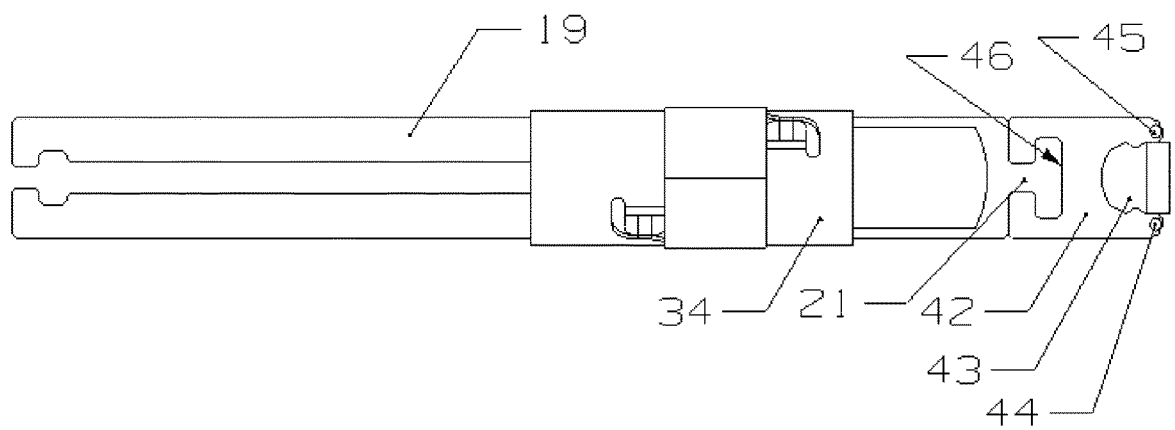
FIG. 22 is a front view showing that the driving head of FIG. 15 extends out of the tool holder.
Figure 23:
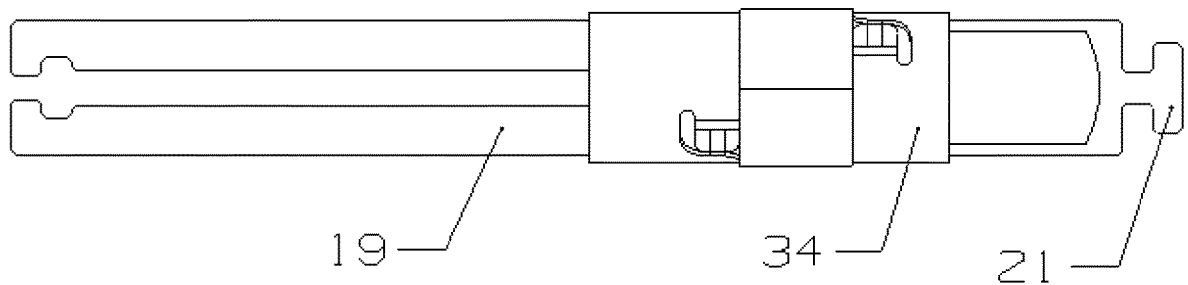
FIG. 23 is a front view showing that the driving head of FIG. 22 is removed from the driving bar.

FIGS. 15-28 illustrate the tool assembly 30 and the driving member 31 according to the second embodiment. The tool assembly 30 includes a first interchangeable tool 32, a second interchangeable tool 33 and a tool holder 34 (see FIG. 15). The first interchangeable tool 32 includes a first open-end mounting groove 35, a first tool slot 36 in a forward-backward direction and a wavelike first tissue contact surface 37 (see FIG. 24). The second interchangeable tool 33 includes a second open-end mounting groove 38, a second tool slot 39 in a forward-backward direction and a wavelike second tissue contact surface 40 (see FIG. 25). The peaks on the first tissue contact surface 37 correspond to the troughs on the second tissue contact surface 40. The tool holder 34 includes a mounting key 41 (see FIG. 28). The mounting key 41 is inserted into the first mounting groove 37 between the tool holder 34 and the first interchangeable tool 32 to form a rotating support of the first interchangeable tool 32 (see FIG. 17). The first interchangeable tool 32 may rotate within a limited angle around the rotating support of the first interchangeable tool 32, so that the first interchangeable tool 32 rotates between an open state and a closed state. The mounting key 41 is inserted into the second mounting groove 38 between the tool holder 34 and the second interchangeable tool 33 to form a rotating support of the second interchangeable tool 33 (see FIG. 20). The second interchangeable tool 33 may rotate within a limited angle around the rotating support of the second interchangeable tool 33, so that the second interchangeable tool 33 rotates between an open state and a closed state. The driving member 31 includes a driving bar 19 and a driving head 42 (see FIG. 26 and FIG. 27). The driving head 42 includes a knife 43, a first inserting block 44, a second inserting block 45 and an inlay groove 46. An inlay key 21 is inserted into the inlay groove 46 between the driving bar 19 and the driving head 42 to form a driving head inlay connection (see FIG. 26). The first inserting block 44 may move back and forth along the first tool slot 36 of the first interchangeable tool 32. The second inserting block 45 may move back and forth along the second tool slot 39 of the second interchangeable tool 33. During the process of replacing the driving head 42, step 1, the operation assembly 3 controls the driving head 42 on the driving bar 19 to move backward, and the first interchangeable tool 32 and the second interchangeable tool 33 are removed from the tool holder 34 respectively; step 2, the operation assembly 3 controls the driving head 42 on the driving bar 19 to move forward until the driving head 42 extends out of the tool holder 34 (see FIG. 22), the inlay key 21 is removed from the inlay groove 46, then the driving head 42 could be removed from the driving bar 19 (see FIG. 23); step 3, the inlay key 21 is inserted into the inlay groove 46 to form a driving head inlay connection between the driving bar 19 and the driving head 42, and the driving head 42 can be installed on the driving bar 19 (see FIG. 22); step 4, the operation assembly 3 controls the driving head 42 on the driving bar 19 to move backward until the driving head 42 returns to the tool holder 34. During the process of respectively mounting the first interchangeable tool 32 and the second interchangeable tool 33 to the tool holder 34, step 1, the operation assembly 3 controls the first inserting block 44 and the second inserting block 45 of the driving head 42 on the driving bar 19 to move backwards, such that the mounting key 41 can be inserted into the first mounting groove 35 through the opening of the first mounting groove 35 to form the rotating support of the first interchangeable tool 32 (see FIG. 16 and FIG. 17), and the mounting key 41 can be inserted into the second mounting groove 38 through the opening of the second mounting groove 38 to form the rotating support of the second interchangeable tool 33 (See FIG. 19 and FIG. 20), the first interchangeable tool 32 and the second interchangeable tool 33 are respectively inserted on the tool holder 34; step 2, the first interchangeable tool 32 and the second interchangeable tool 33 are in a fully open state, the operation assembly 3 controls the driving head 42 on the driving bar 19 to move forward, and the first inserting block 44 on the driving head 42 insert into the first tool slot 36 of the first interchangeable tool 32, such that the first inserting block 44 prevents the mounting key 41 from moving out of the opening of the first mounting groove 35, and the first interchangeable tool 32 is mounted on the tool holder 43 (see FIG. 18); similarly, the second inserting block 45 on the driving head 45 moves forward and insert into the second tool slot 39 of the second interchangeable tool 33, such that the second inserting block 45 prevents the mounting key 41 from moving out of the opening of the second mounting groove 38, and the second interchangeable tool 33 is mounted on the tool holder 34 (see FIG. 21).

When the first interchangeable tool 32 and the second interchangeable tool 33 are in an open state, the operation assembly 3 controls the first inserting block 44 and the second inserting block 45 on the driving head 42 on the driving bar 19 to move forward at the back parts of the first tool slot 36 of the first interchangeable tool 32 and the second tool slot 39 of the second interchangeable tool 33, respectively, so as to drive the first interchangeable tool 32 and the second interchangeable tool 33 to rotate around the rotating support of the first interchangeable tool 32 and the rotating support of the second interchangeable tool 33 towards the closing direction, respectively. When the first inserting block 44 and the second inserting block 45 on the driving head 42 are respectively moved to different locations at the back parts of the first tool slot 36 of the first interchangeable tool 32 and the second tool slot 39 of the second interchangeable tool 33, the open/close angle between the first interchangeable tool 32 and the second interchangeable tool 33 is changed. When the first interchangeable tool 32 and the second interchangeable tool 33 are in a closed state, the tissue to be cut is clamped between the peaks and troughs of the first tissue contact surface 37 of the first interchangeable tool 32 and the second tissue contact surface 40 of the second interchangeable tool 33. After that the first inserting block 44 on the driving head 42 moves forward along the first tool slot 36 of the first interchangeable tool 32 and the second inserting block 45 on the driving head 42 moves forward along the second tool slot 39 of the second interchangeable tool 33, the first interchangeable tool 32 and the second interchangeable tool 33 are kept in a closed state. At the same time, the knife 43 at the front part of the driving head 42 cuts the tissue clamped between the first tissue contact surface 37 of the first interchangeable tool 32 and the second tissue contact surface 40 of the second interchangeable tool 33.

Figure 29:
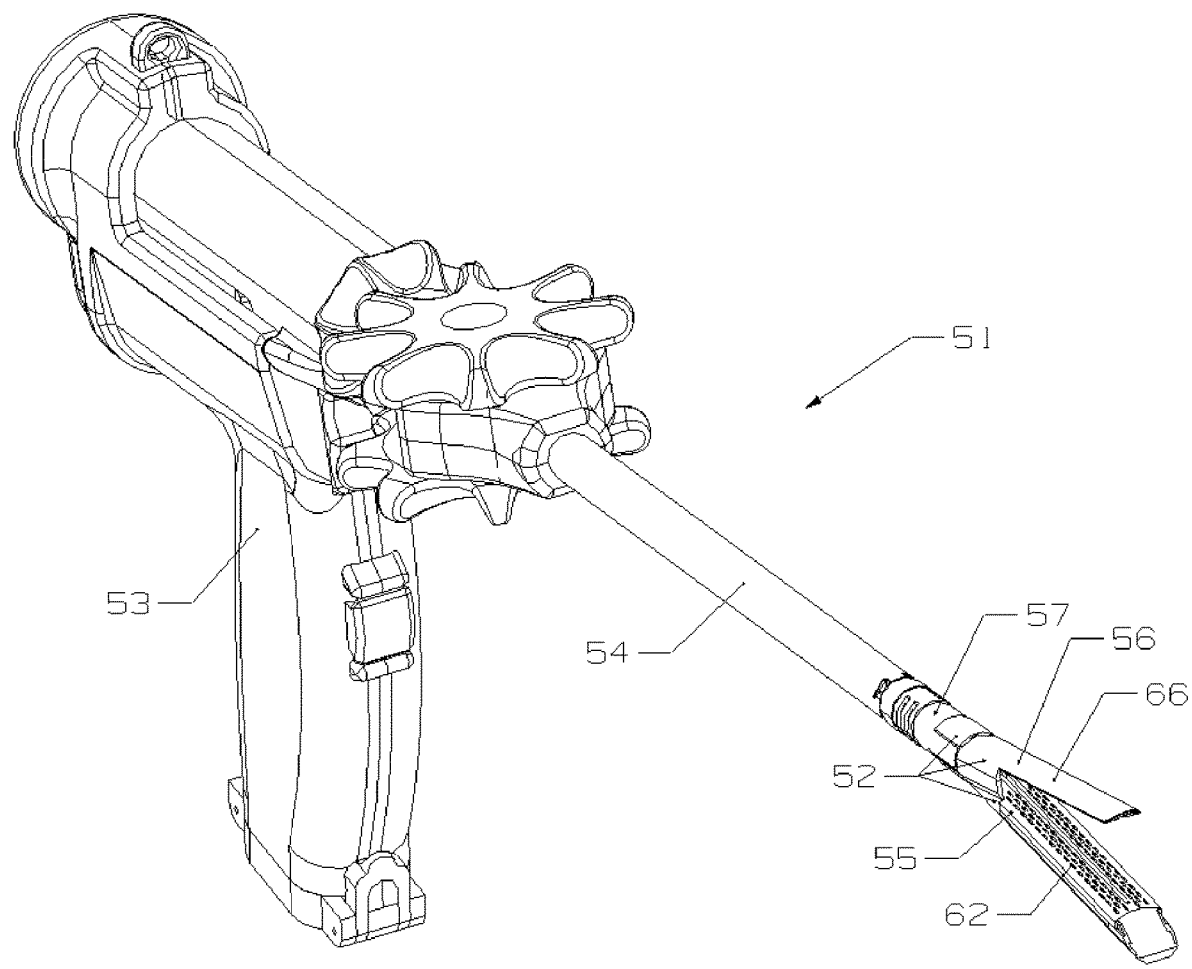
FIG. 29 is a perspective view of an electric multipurpose endoscopic surgical instrument according to the present disclosure.
Figure 30:
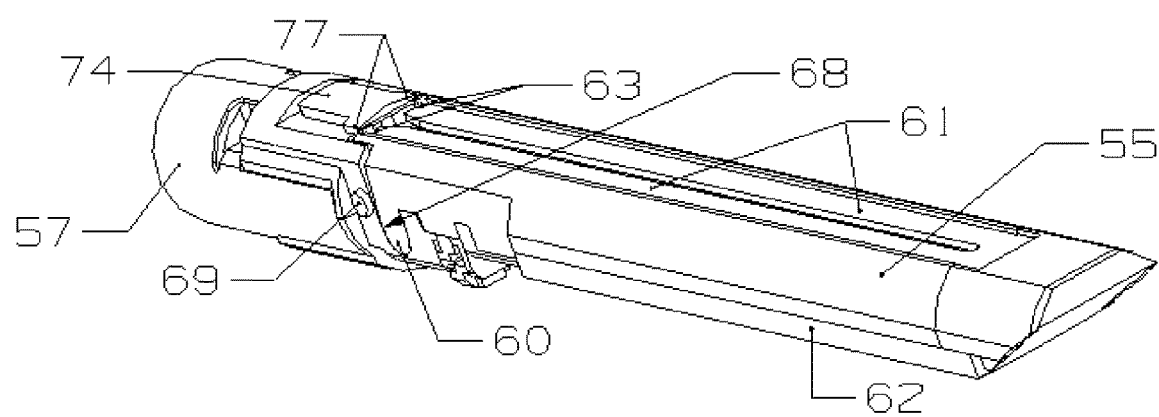
FIG. 30 is a perspective view showing that the first interchangeable tool is pressed on the tool holder according to the third embodiment of the present disclosure.

FIG. 29 is an electric multipurpose endoscopic surgical instrument 51 according to the present disclosure. The endoscopic surgical instrument 51 includes a tool assembly 52, an electric operation assembly 53 and an elongated body 54. The elongated body 54 connects the operation assembly 53 and the tool assembly 52.

Figures 31, 32:
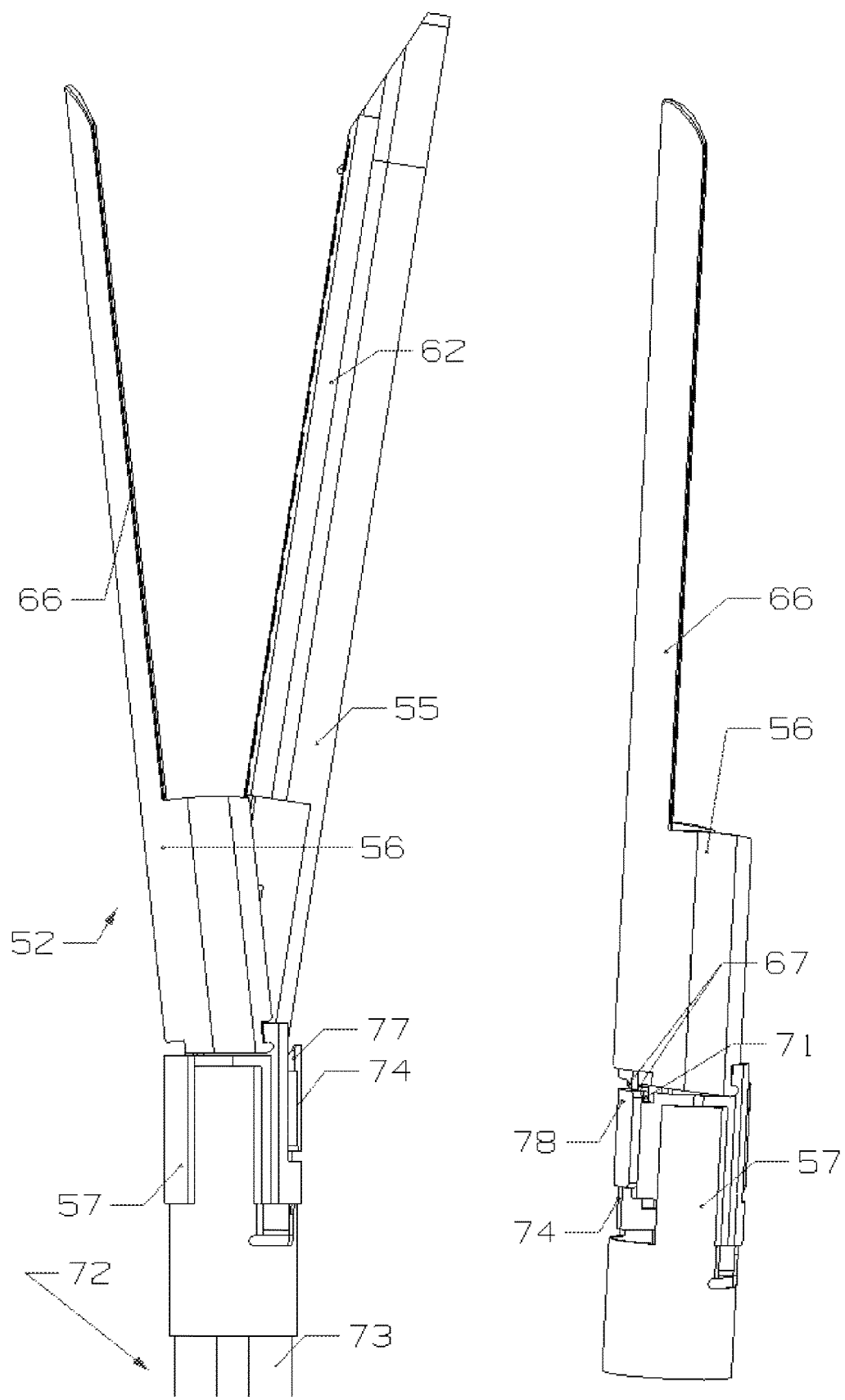
FIG. 31 is a front view of the tool assembly and driving member according to the third embodiment of the present disclosure.
FIG. 32 is a perspective view showing a state in which the second interchangeable tool is pressed on the tool holder of FIG. 31.
Figure 39:
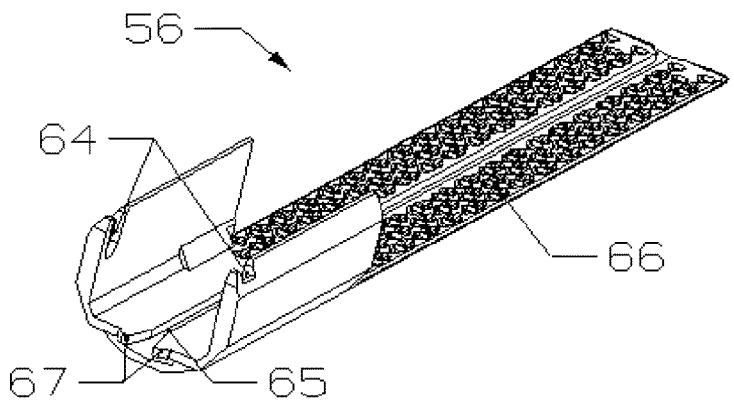
FIG. 39 is a perspective view showing the second interchangeable tool of FIG. 31.
Figure 40:
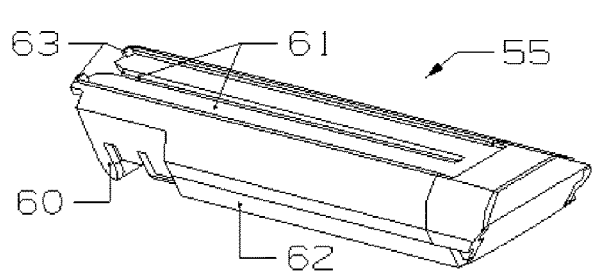
FIG. 40 is a perspective view showing the first interchangeable tool of FIG. 31.
Figure 41:
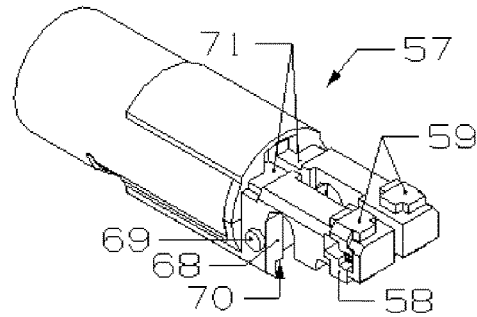
FIG. 41 is a perspective view showing the tool holder of FIG. 31.

FIGS. 30-46 illustrate the tool assembly 52 and the driving member 72 according to the third embodiment. The tool assembly 52 includes a first interchangeable tool 55, a second interchangeable tool 56 and a tool holder 57 (see FIG. 31). The first interchangeable tool 55 includes a first mounting key 60, a first tool slot 61 in a forward-backward direction, a staple cartridge 62 and a first constraining key 63 (see FIG. 40). The second interchangeable tool 56 includes a second open-end mounting groove 64, a second tool slot 65 in a forward-backward direction, an anvil 66 and a second constraining key 67 (see FIG. 39). The tool holder 57 includes a first open-end mounting groove 68, a second mounting key 69, a first opening constraining groove 70, a second opening constraining groove 71, a first opening elastic part 58 and a second opening elastic part 59 (see FIG. 41). The first mounting key 60 is inserted into the first open-end mounting groove 68 between the first interchangeable tool 55 and the tool holder 57 to form a rotating support of the first interchangeable tool 55 (see FIG. 35). The force of the first opening elastic part 58 on the first interchangeable tool 55 is located at the middle back part of the first interchangeable tool 55. The force of the first opening elastic part 58 causes the first interchangeable tool 55 to rotate within a limited angle around the rotating support of the first interchangeable tool 55 toward the opening direction. The second mounting key 69 is inserted into the second open-end mounting groove 64 between the second interchangeable tool 56 and the tool holder 57 to form a rotating support of the second interchangeable tool 56. The force of the second opening elastic part 59 on the second interchangeable tool 56 is located at the middle back part of the second interchangeable tool 56 (see FIG. 37). The force of the second opening elastic part 59 causes the second interchangeable tool 56 to rotate within a limited angle around the rotating support of the second interchangeable tool 56 toward the opening direction.

Figure 42:
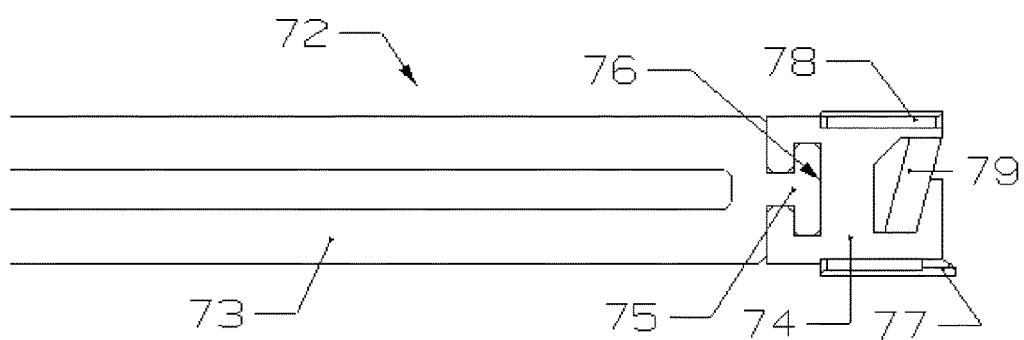
FIG. 42 is a partial front view of the driving member of FIG. 31.
Figure 43:
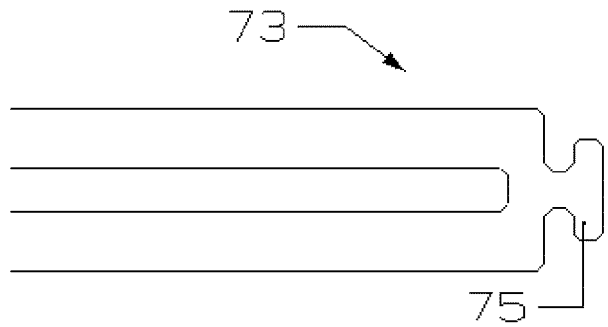
FIG. 43 is a partial front view of the driving bar of FIG. 42.
Figure 44:
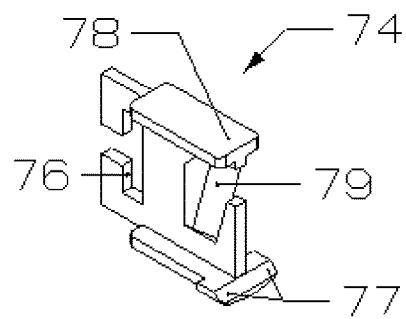
FIG. 44 is a perspective view of the driving head of FIG. 42.
Figure 45:
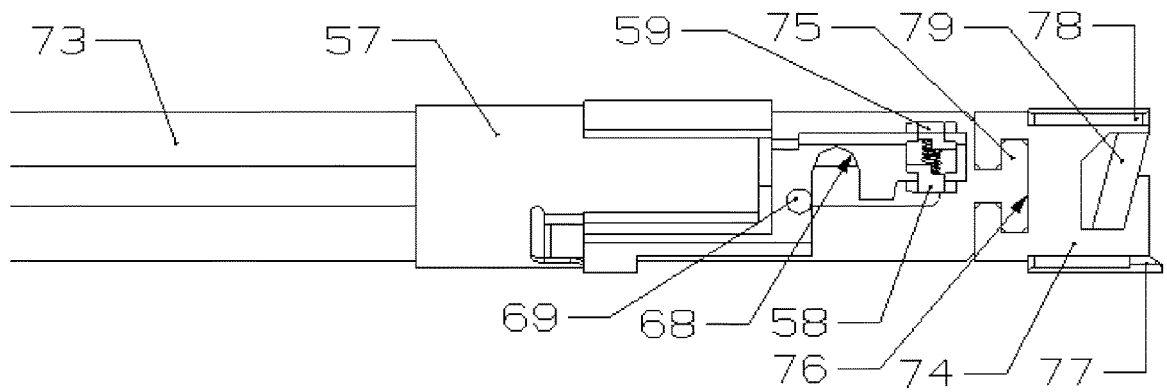
FIG. 45 is a front view showing that the driving head of FIG. 31 extends out of the tool holder.
Figure 46:
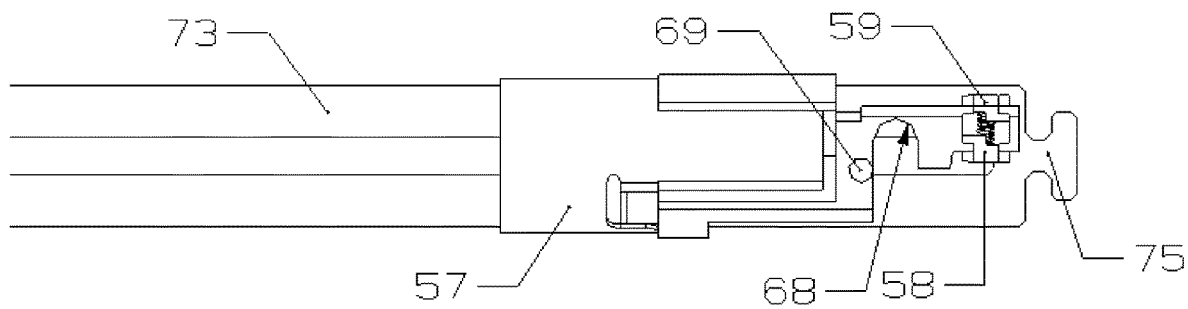
FIG. 46 is a front view showing that the driving head of FIG. 45 is removed from the driving bar.

As shown in FIGS. 42-44, the operation assembly 53 includes a driving member 72. The operation assembly 53 controls the driving member 72 to move forward and backward. The driving member 72 includes a driving bar 73 and a driving head 74. An inlay key 75 is inserted into an inlay groove 76 between the driving bar 73 and the driving head 74 to form a driving head inlay connection. The driving head 74 includes a first inserting block 77, a second inserting block 78 and a knife 79. The first inserting block 77 may move back and forth along the first tool slot 61 of the first interchangeable tool 55. The second inserting block 78 may move back and forth along the second tool slot 65 of the second interchangeable tool 56. The operation assembly 53 controls the actions of the first interchangeable tool 55 and the second interchangeable tool 56 in the tool assembly 52 through the driving member 72.

Figure 35:
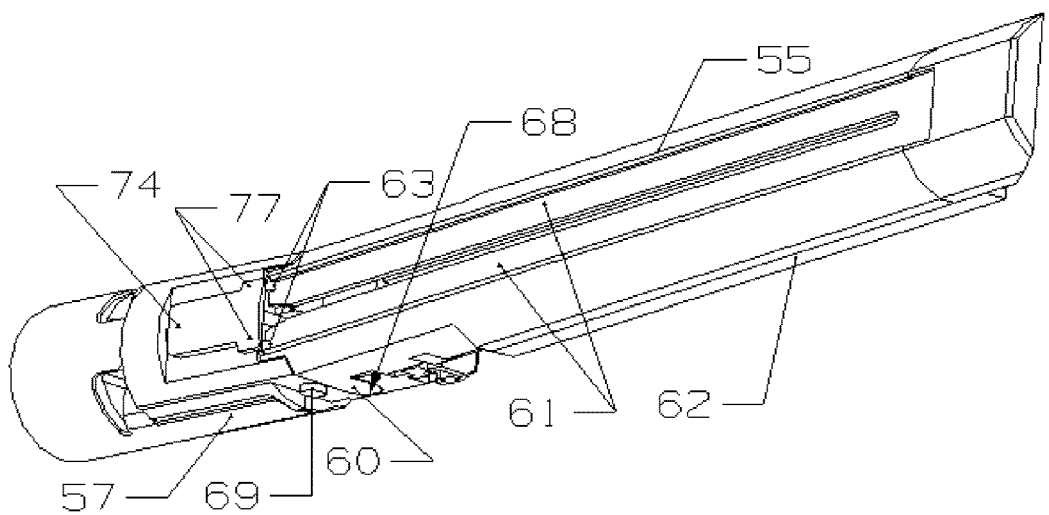
FIG. 35 is a perspective view showing that the first interchangeable tool of FIG. 30 is mounted on the tool holder.
Figure 36:
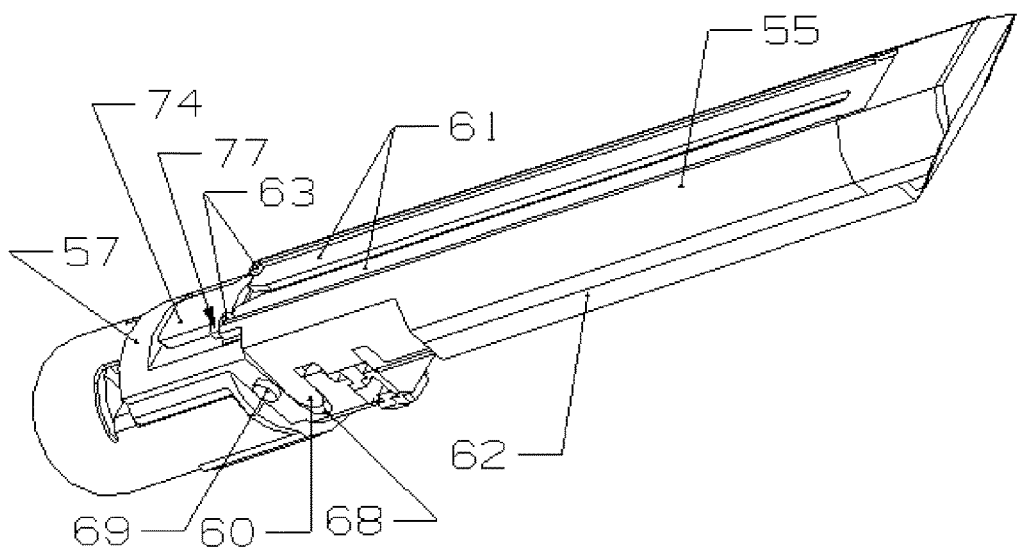
FIG. 36 is a perspective view showing a state in which the first interchangeable tool of FIG. 30 is partially removed from the tool holder.

During the process of mounting the first interchangeable tool 55 to the tool holder 57, step 1, the force of the first opening elastic part 58 is overcome to press it on the middle back part of the first interchangeable tool 55 toward the direction of the rotating support of the first interchangeable tool 55, and the first mounting key 60 is inserted into the first mounting groove 68 through the opening of the first mounting groove 68, then the first interchangeable tool 55 is loosened (see FIG. 30); step 2, under the action of the first opening elastic part 58, the first mounting key 60 rotates in the first mounting groove 68, so as to drive the first constraining key 63 of the first interchangeable tool 55 to rotate into the first constraining groove 70 of the tool holder 57, then the first interchangeable tool 55 is mounted on the tool holder 57 (see FIG. 35). During the process of removing the first interchangeable tool 55 from the tool holder 57, step 1, the force of the first opening elastic part 58 is overcome to press it on the front part of the first interchangeable tool 55 toward the direction of the rotating support of the first interchangeable tool 55, such that the first mounting key 60 rotates in the first mounting groove 68, so as to drive the first constraining key 63 of the first interchangeable tool 55 to rotate out of the first constraining groove 70 of the tool holder 57 (see FIG. 30); step 2, the force of the first opening elastic part 58 which is located at the middle back part of the first interchangeable tool 55 pushes the first interchangeable tool 55 toward the opposite direction of the rotating support of the first interchangeable tool 55, so as to push the first mounting key 60 out towards the opening of the first mounting groove 68, then the first interchangeable tool 55 could be removed out of the tool holder 57 (see FIG. 36).

Figure 33:
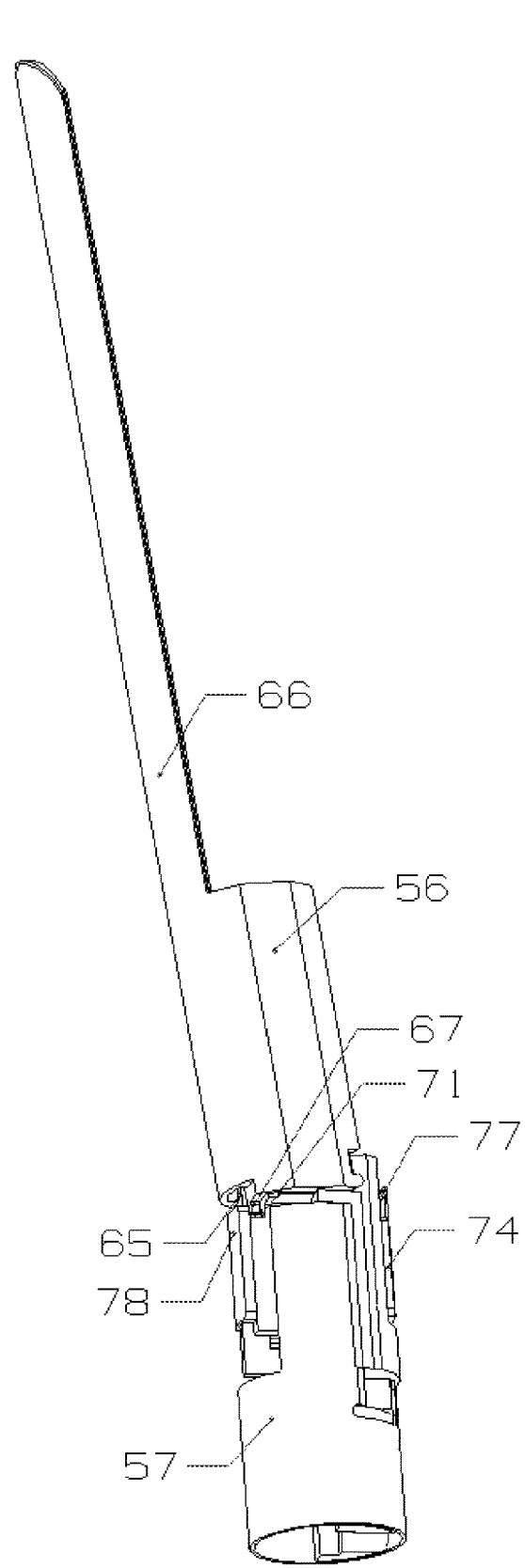
FIG. 33 is a perspective view showing that the second interchangeable tool of FIG. 31 is mounted on the tool holder.
Figure 34:
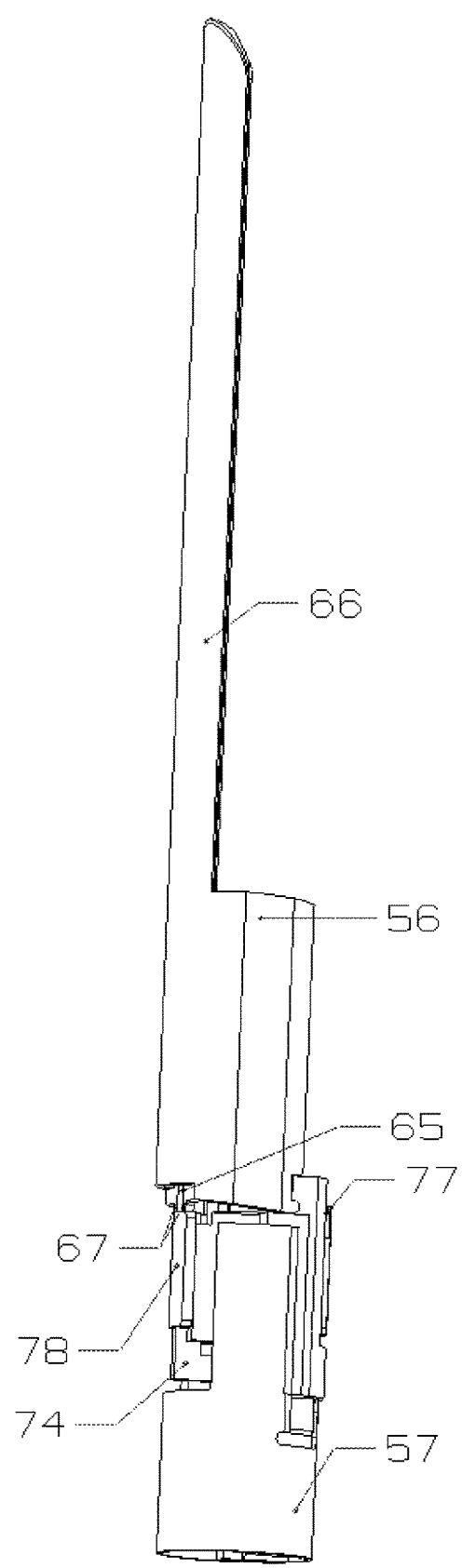
FIG. 34 is a perspective view showing a state in which the second interchangeable tool of FIG. 31 is partially removed from the tool holder.
Figure 37:
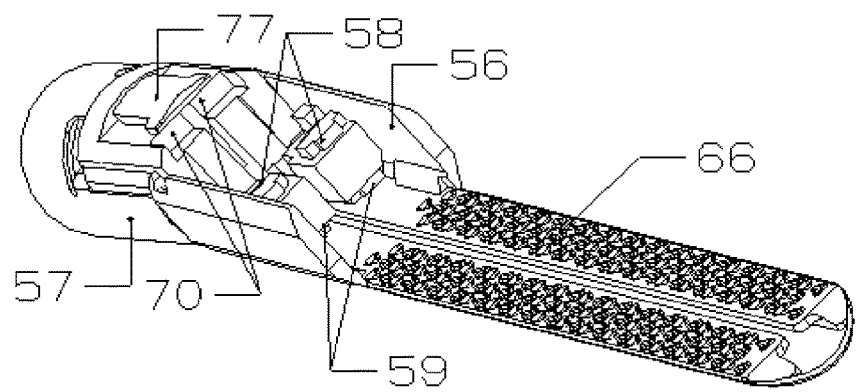
FIG. 37 is a perspective view showing the back of the position of FIG. 33.
Figure 38:
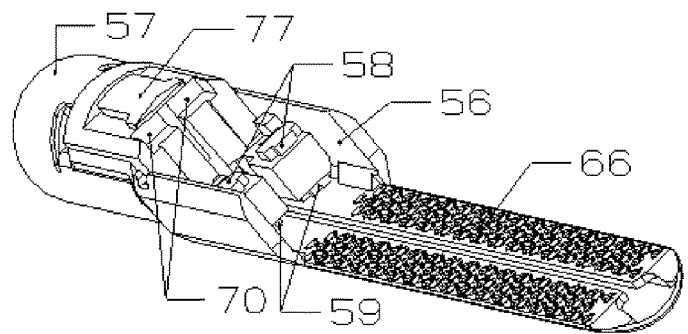
FIG. 38 is a perspective view showing the back of the position of FIG. 34.

During the process of mounting the second interchangeable tool 56 to the tool holder 57, step 1, the force of the second opening elastic part 59 is overcome to press it on the middle back part of the second interchangeable tool 56 toward the direction of the rotating support of the second interchangeable tool 56, and the second mounting key 69 is inserted into the second mounting groove 64 through the opening of the second mounting groove 64, then the second interchangeable tool 56 is loosened (see FIG. 32); step 2, under the action of the second opening elastic part 59, the second mounting key 69 rotates in the second mounting groove 64, so as to drive the second constraining key 67 of the second interchangeable tool 56 to rotate into the second constraining groove 71 of the tool holder 57, and the second interchangeable tool 56 is mounted on the tool holder 57 (see FIG. 33 and FIG. 37). During the process of removing the second interchangeable tool 56 from the tool holder 57, step 1, the force of the second opening elastic part 59 is overcome to press it on the front part of the second interchangeable tool 56 toward the direction of the rotating support of the second interchangeable tool 56, such that the second mounting key 69 rotates in the second mounting groove 64, so as to drive the second constraining key 67 of the second interchangeable tool 56 to rotate out of the second constraining groove 71 of the tool holder 57 (see FIG. 32); step 2, the force of the second opening elastic part 59 located at the middle back part of the second interchangeable tool 56 pushes the second interchangeable tool 56 toward the opposite direction of the rotating support of the second interchangeable tool 56, so as to push the second mounting key 69 out towards the opening of the second mounting groove 64 (see FIG. 34 and FIG. 38), then the second interchangeable tool 56 could be removed out of the tool holder 57.

When the operation assembly 53 controls the first inserting block 77 and the second inserting block 78 on the driving head 74 on the driving bar 73 to respectively press on the back part of the first tool slot 61 of the first interchangeable tool 55 and the second tool slot 65 of the second interchangeable tool 56 to move forwards, the first opening elastic part 58 and the second opening elastic part 59 respectively keep that the first inserting block 77 and the second inserting block 78 on the driving head 74 are in contact with the first tool slot 61 of the first interchangeable tool 55 and the second tool slot 65 of the second interchangeable tool 56. The first inserting block 77 and the second inserting block 78 on the driving head 74 drive the first interchangeable tool 55 and the second interchangeable tool 56 to rotate towards the closing direction, respectively. When the operation assembly 53 controls the first inserting block 77 and the second inserting block 78 on the driving head 74 on the driving bar 73 to respectively press on the back part of the first tool slot 61 of the first interchangeable tool 55 and the second tool slot 65 of the second interchangeable tool 56 to move backwards, the first opening elastic part 58 and the second elastic part 59 respectively keep that the first inserting block 77 and the second inserting block 78 on the driving head 74 are in contact with the first tool slot 61 of the first interchangeable tool 55 and the second tool slot 65 of the second interchangeable tool 56. The first inserting block 77 and the second inserting block 78 on the driving head 74 drive the first interchangeable tool 55 and the second interchangeable tool 56 to rotate towards the opening direction, respectively. When the first inserting block 77 and the second inserting block 78 on the driving head 74 on the driving bar 73 are moved to the middle front part of the first tool slot 61 of the first interchangeable tool 55 and the second tool slot 65 of the second interchangeable tool 56, the first interchangeable tool 55 and the second interchangeable tool 56 are kept in a closed state.

The staple cartridge 62 in the first interchangeable tool 55, the anvil 66 in the second interchangeable tool 56 and the knife 79 on the driving head 74 may be used to cut and staple the tissue. In the use of the endoscopic surgical instrument 51, if the knife 79 on the driving head 74 is found to be damaged, a spare driving head 74 may be selected to replace the in-use driving head 74. During the process of replacing the driving head 74, step 1, the operation assembly 53 controls the first inserting block 77 and the second inserting block 78 on the in-use driving head 74 on the driving bar 73 to move backward, and moves the first interchangeable tool 55 and the second interchangeable tool 56 out of the tool holder 57, respectively; step 2, the operation assembly 53 controls the in-use driving head 74 on the driving bar 73 to move forward until the in-use driving head 74 extends out of the tool holder 57 (see FIG. 45), the inlay key 75 is removed from the inlay groove 76, then the in-use driving head 74 could be removed from the driving bar 73 (see FIG. 46); step 3, the inlay key 75 is inserted into the inlay groove 76 between the driving bar 73 and the spare driving head 74 to form a driving head inlay connection, and the spare driving head 74 can be installed on the driving bar 73; step 4, the operation assembly 53 controls the spare driving head 74 on the driving bar 73 to move backward until the spare driving head 74 returns to the tool holder 57; step 5, the first interchangeable tool 55 and the second interchangeable tool 56 are installed on the tool holder 57, respectively (see FIG. 31).

After the endoscopic surgical instrument 51 is used, according to the requirements of endoscopic surgery, the first interchangeable tool or the second interchangeable tool with the same specification may be replaced; or, the first interchangeable tool or the second interchangeable tool with a different specification may be replaced; tools with other functions may also be replaced or used.

Figure 47:
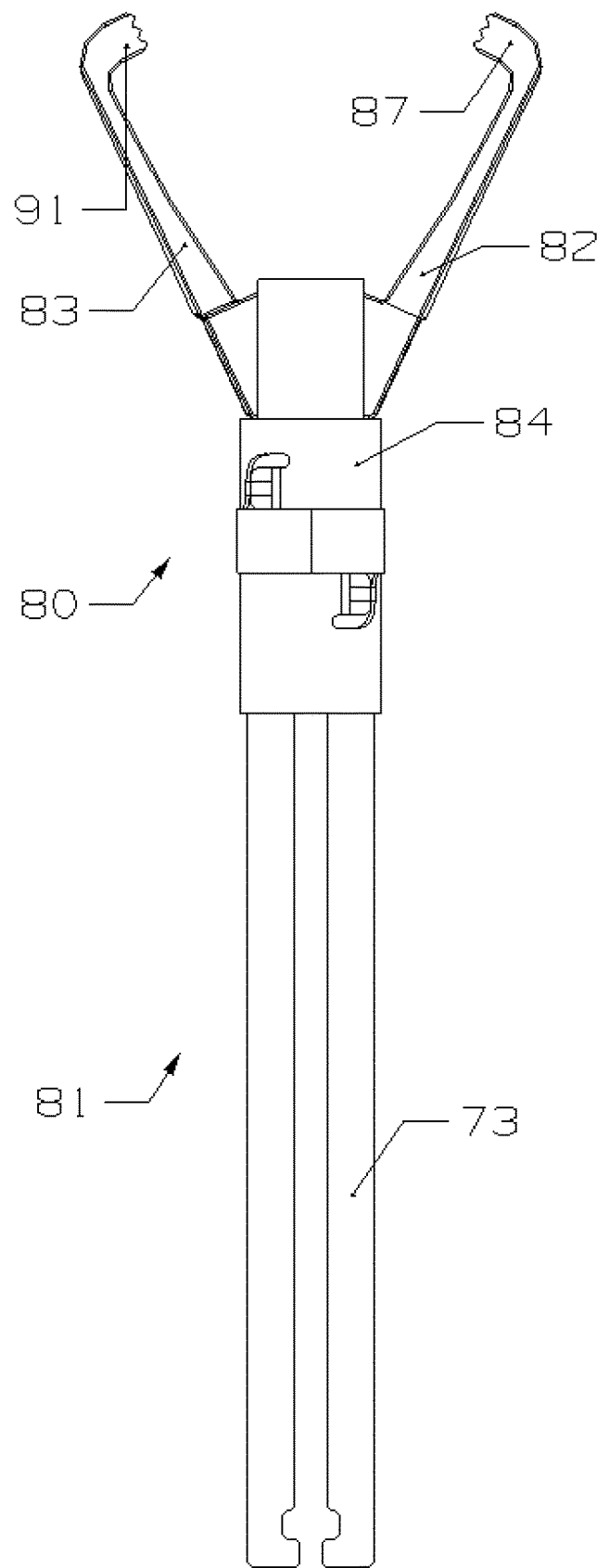
FIG. 47 is a front view of the tool assembly and driving member according to the fourth embodiment of the present disclosure.
Figure 48:
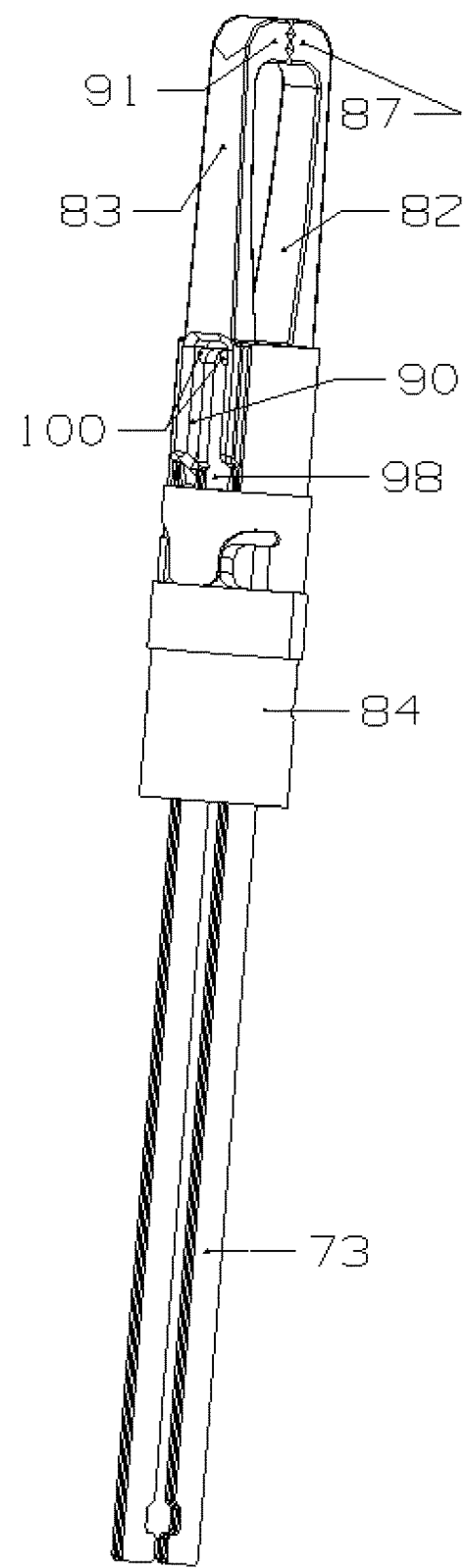
FIG. 48 is a perspective view showing that the first interchangeable tool and the second interchangeable tool in FIG. 47 are clamped.
Figure 49:
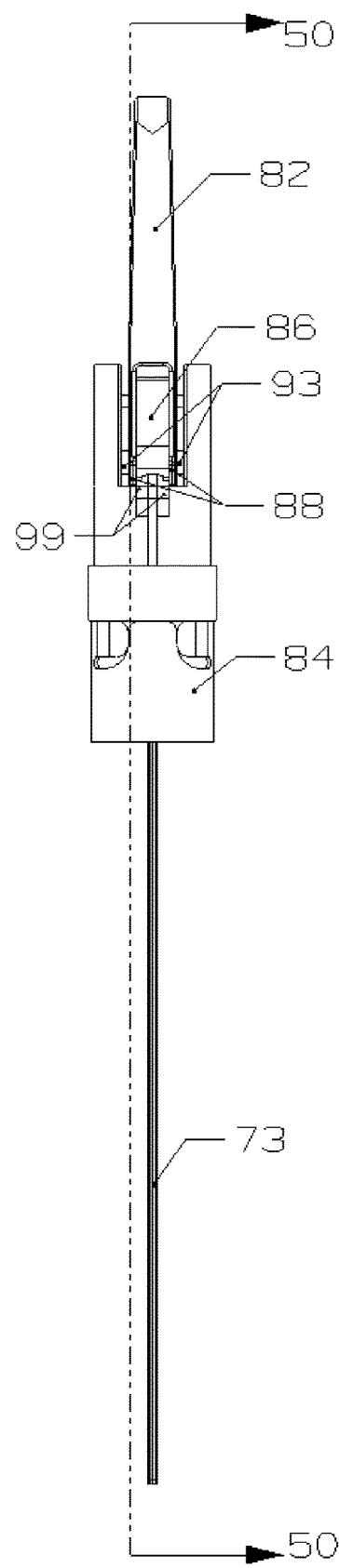
FIG. 49 is a bottom view showing a state in which the first interchangeable tool is pressed on the tool holder of FIG. 47.
Figure 50:
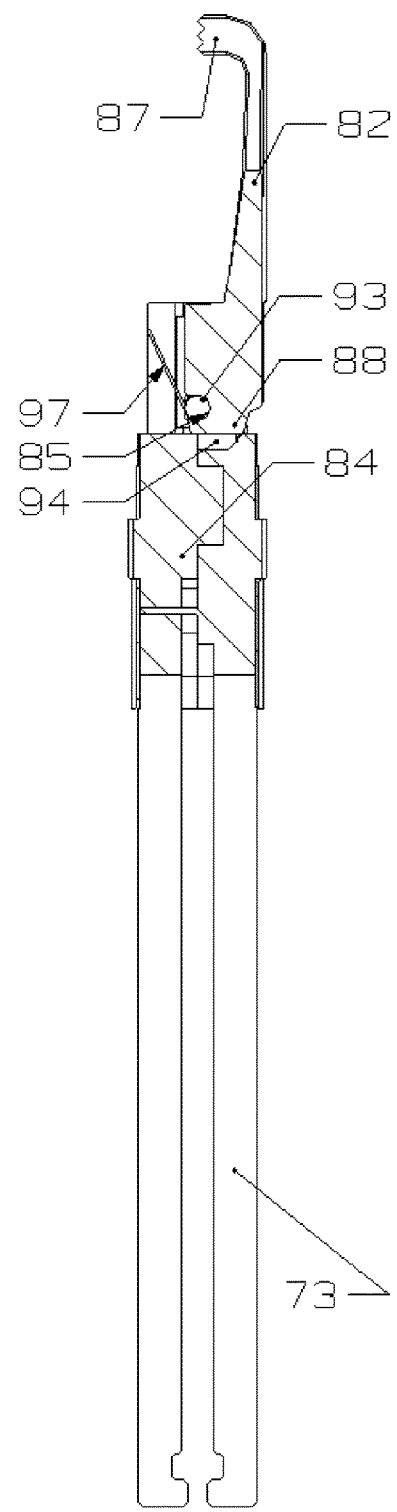
FIG. 50 is a sectional view of the 50-50 profile of FIG. 49.
Figure 56:
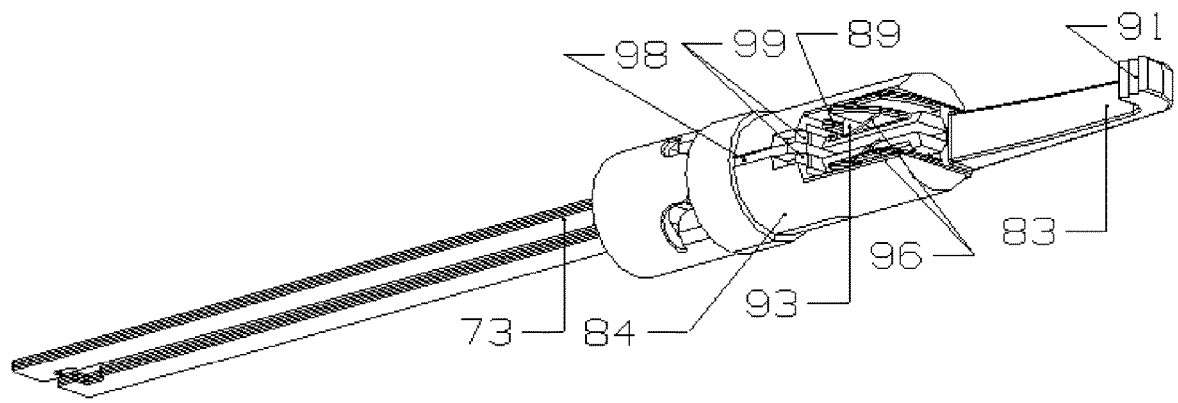
FIG. 56 is a perspective view showing the back of the position of FIG. 55.
Figure 60:
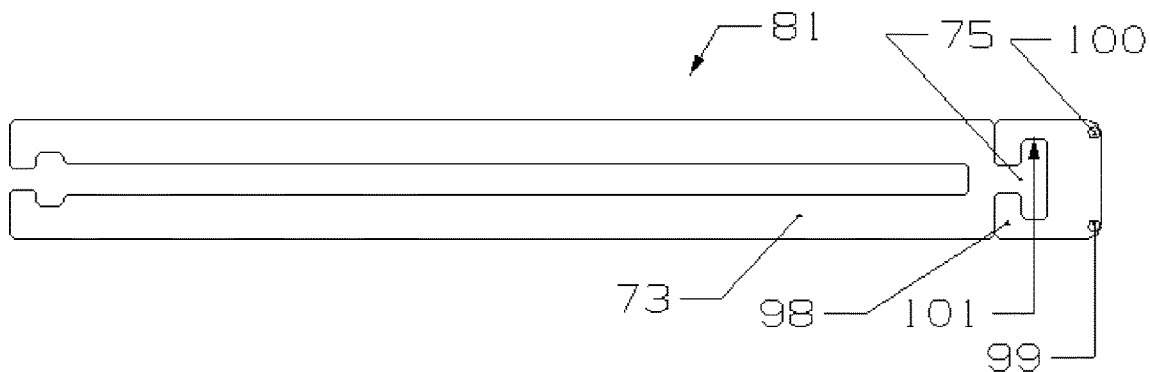
FIG. 60 is a front view of the driving member of FIG. 47.
Figure 61:
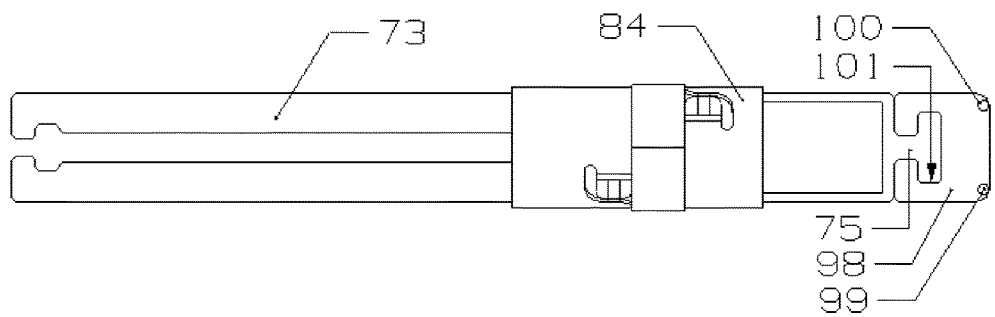
FIG. 61 is a front view showing that the driving head extends out of the tool holder.
Figure 62:
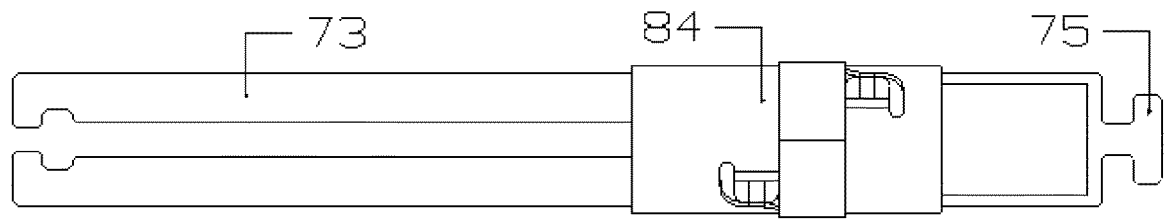
FIG. 62 is a front view showing that the driving head of FIG. 61 is removed from a driving bar.
Figures 63, 64:
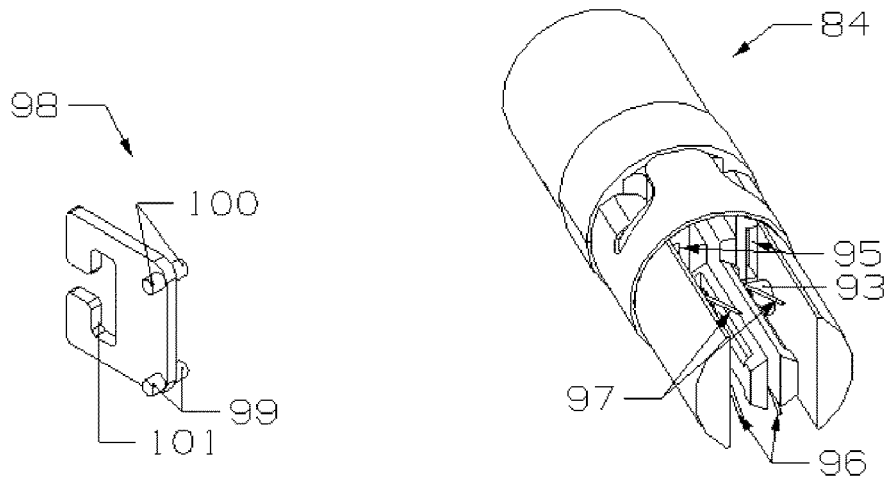
FIG. 63 is a perspective view of the driving head of FIG. 60.
FIG. 64 is a perspective view showing the tool holder of FIG. 47.
Figure 65:
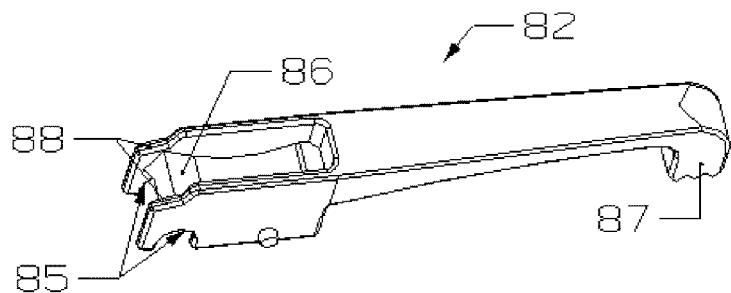
FIG. 65 is a perspective view showing the first interchangeable tool of FIG. 47.
Figure 66:
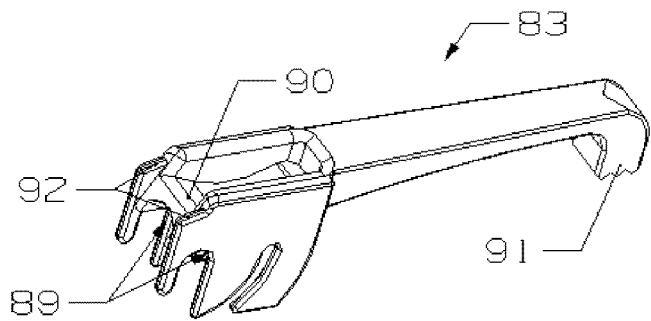
FIG. 66 is a perspective view showing the second interchangeable tool of FIG. 47.

FIGS. 47-66 describe the tool assembly 80 and the driving member 81 according to the fourth embodiment. The tool assembly 80 includes a first interchangeable tool 82, a second interchangeable tool 83 and a tool holder 84 (see FIG. 47). The first interchangeable tool 82 includes a first open-end mounting groove 85, a first tool slot 86 in a forward-backward direction, a jaw 87 and a first constraining key 88 (see FIG. 65). The second interchangeable tool 83 includes a second open-end mounting groove 89, a second tool slot 90 in a forward-backward direction, a jaw 91 and a second constraining key 92 (see FIG. 66). The tool holder 84 includes a mounting key 93, a first opening constraining groove 94, a second opening constraining groove 95, a first opening elastic part 96 and a second opening elastic part 97 (see FIG. 50, FIG. 52, FIG. 54 and FIG. 64). The mounting key 93 is inserted into the first open-end mounting groove 85 between the first interchangeable tool 82 and the tool holder 84 to form a rotating support of the first interchangeable tool 82 (see FIG. 52). The force of the first opening elastic part 96 on the first interchangeable tool 82 is located at the middle back part of the first interchangeable tool 82. The force of the first opening elastic part 96 causes the first interchangeable tool 82 to rotate within a limited angle around the rotating support of the first interchangeable tool 82 toward the opening direction. The mounting key 93 is inserted into the second open-end mounting groove 89 between the second interchangeable tool 83 and the tool holder 84 to form a rotating support of the second interchangeable tool 83 (see FIG. 56). The force of the second opening elastic part 97 on the second interchangeable tool 83 is located at the middle back part of the second interchangeable tool 83. The force of the second opening elastic part 97 causes the second interchangeable tool 83 to rotate within a limited angle around the rotating support of the second interchangeable tool 83 toward the opening direction. The driving member 81 includes a driving bar 73 and a driving head 98 (see FIG. 60 and FIG. 63). The driving head 98 includes a first inserting block 99, a second inserting block 100 and an inlay groove 101. An inlay key 75 is inserted into the inlay groove 101 between the driving bar 73 and the driving head 98 to form a driving head inlay connection.

During the process of replacing the driving head 96, step 1, the operation assembly 53 controls the driving head 98 on the driving bar 73 to move backward, and moves the first interchangeable tool 82 and the second interchangeable tool 83 out of the tool holder 84 respectively; step 2, the operation assembly 53 controls the driving head 98 on the driving bar 73 to move forward until the driving head 98 extends out of the tool holder 84 (see FIG. 61), the inlay key 75 is removed from the inlay groove 101, then the driving head 98 could be removed from the driving bar 73 (see FIG. 62); step 3, the inlay key 75 is inserted into the inlay groove 101 between the driving bar 73 and the driving head 98 to form the driving head inlay connection, and the driving head 98 can be installed on the driving bar 73 (see FIG. 61); step 4, the operation assembly 53 controls the driving head 98 on the driving bar 73 to move backward until the driving head 98 returns to the tool holder 84.

Figure 51:
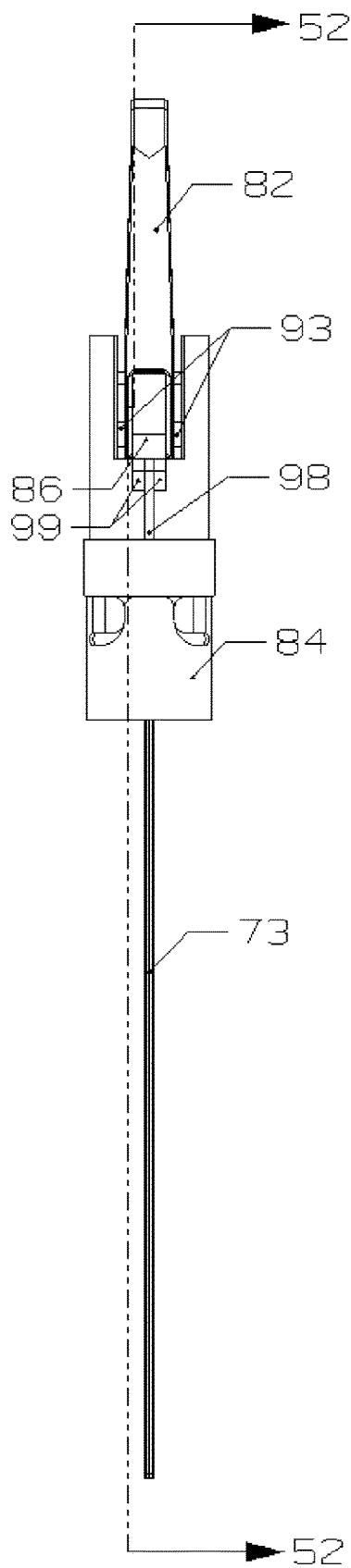
FIG. 51 is a bottom view showing that the first interchangeable tool of FIG. 47 is mounted on the tool holder.
Figure 52:
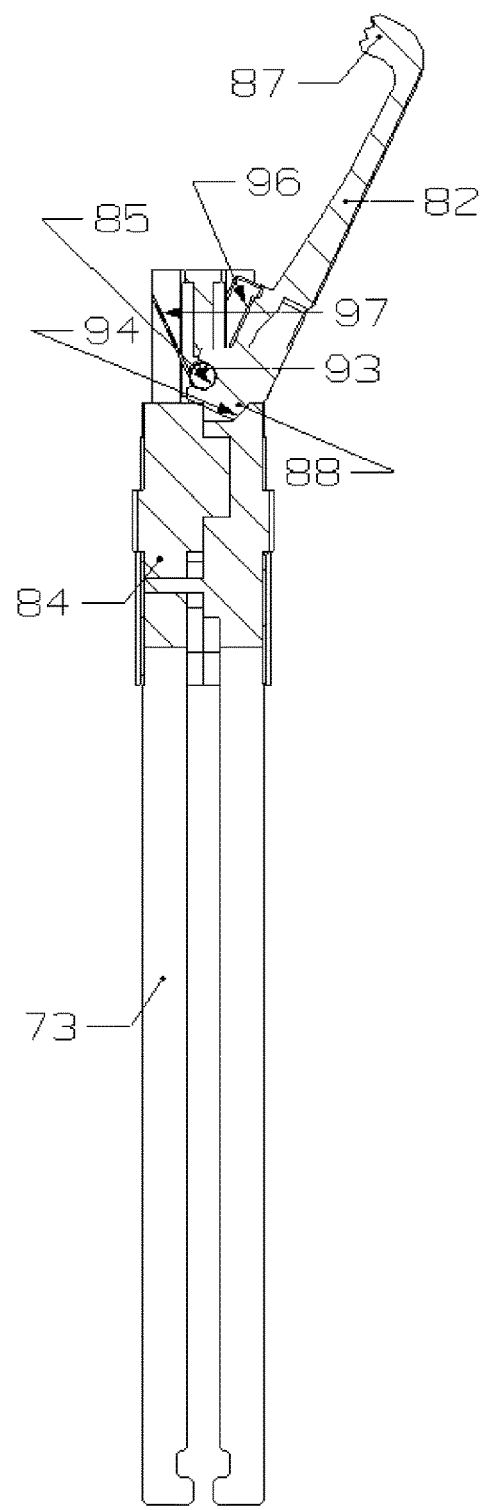
FIG. 52 is a section view of the 52-52 profile of FIG. 51.
Figure 53:
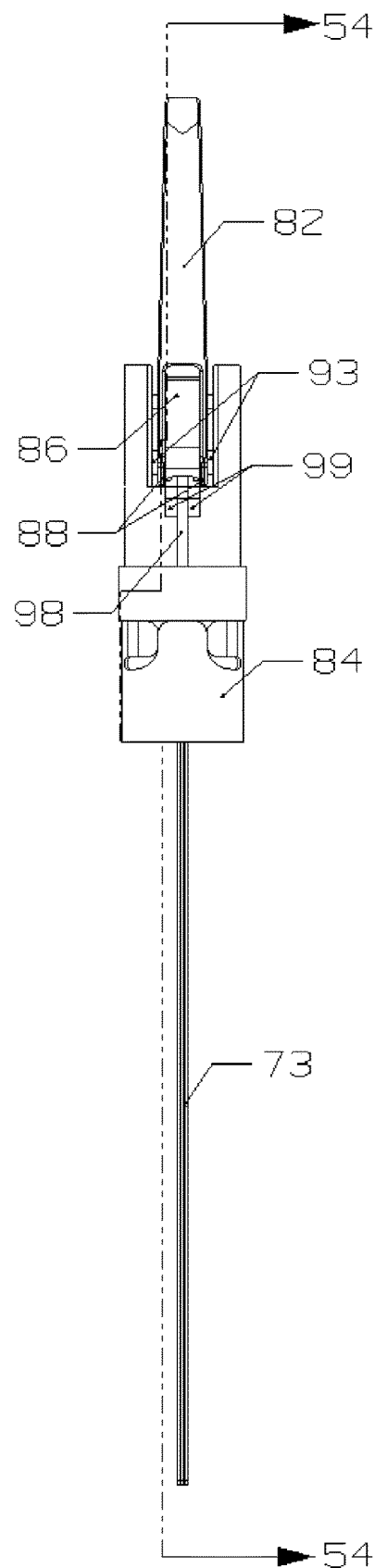
FIG. 53 is a bottom view showing a state in which the first interchangeable tool of FIG. 47 is partially removed from the tool holder.
Figure 54:
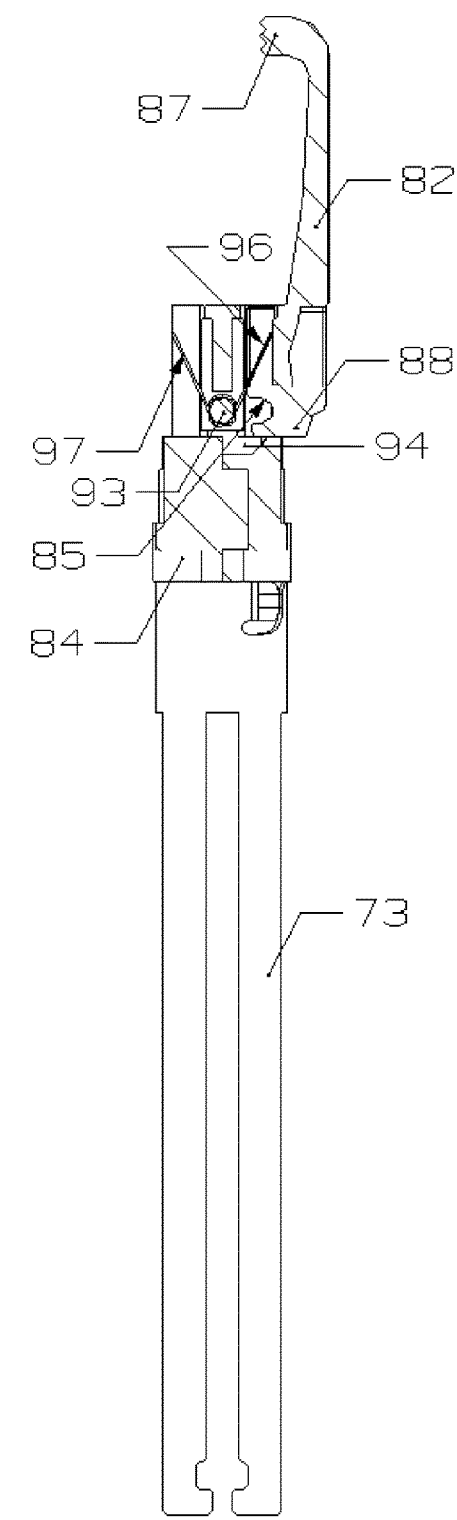
FIG. 54 is a section view of the 54-54 profile of FIG. 53.
Figure 55:
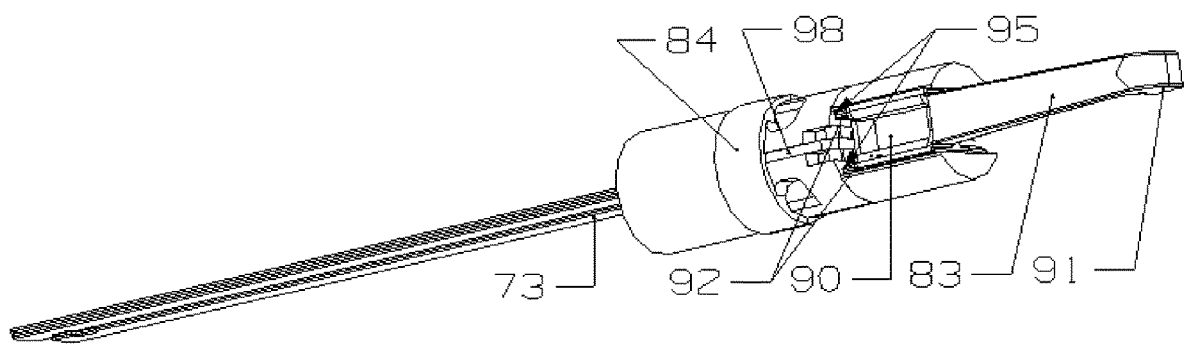
FIG. 55 is a perspective view showing a state in which the second interchangeable tool is pressed on the tool holder of FIG. 47.

During the process of mounting the first interchangeable tool 82 to the tool holder 84, step 1, the force of the first opening elastic part 96 is overcome to press it on the middle back part of the first interchangeable tool 82 toward the direction of the rotating support of the first interchangeable tool 82, and the mounting key 93 is inserted into the first mounting groove 85 through the opening of the first mounting groove 85, then the first interchangeable tool 82 is loosened (see FIG. 49 and FIG. 50); step 2, under the action of the first opening elastic part 96, the mounting key 93 rotates in the first mounting groove 85, so as to drive the first constraining key 88 of the first interchangeable tool 82 to rotate into the first constraining groove 94 of the tool holder 84, then the first interchangeable tool 82 is mounted on the tool holder 84 (see FIG. 51 and FIG. 52). During the process of removing the first interchangeable tool 82 from the tool holder 84, step 1, the force of the first opening elastic part 96 is overcome to press it on the front part of the first interchangeable tool 82 toward the direction of the rotating support of the first interchangeable tool 82, such that the mounting key 93 rotates in the first mounting groove 85, so as to drive the first constraining key 88 of the first interchangeable tool 82 to rotate out of the first constraining groove 94 of the tool holder 84 (see FIG. 49 and FIG. 50); step 2, the force of the first opening elastic part 96 located at the middle back part of the first interchangeable tool 82 pushes the first interchangeable tool 82 toward the opposite direction of the rotating support of the first interchangeable tool 82, so as to push the mounting key 93 out towards the opening of the first mounting groove 85 (see FIG. 53 and FIG. 54), then the first interchangeable tool 82 could be removed out of the tool holder 84.

Figure 57:
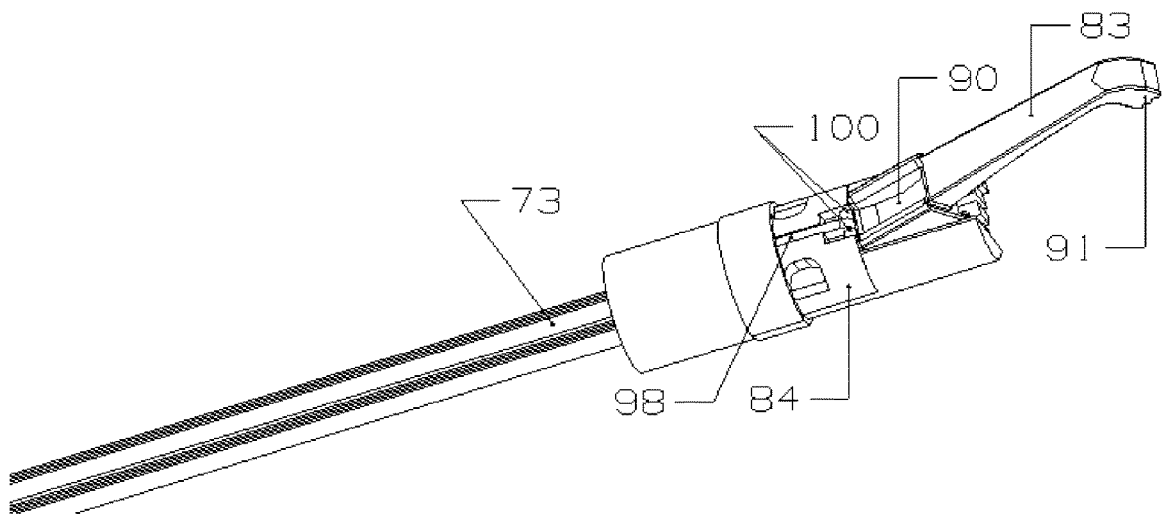
FIG. 57 is a perspective view showing that the second interchangeable tool of FIG. 47 is mounted on the tool holder.
Figure 58:
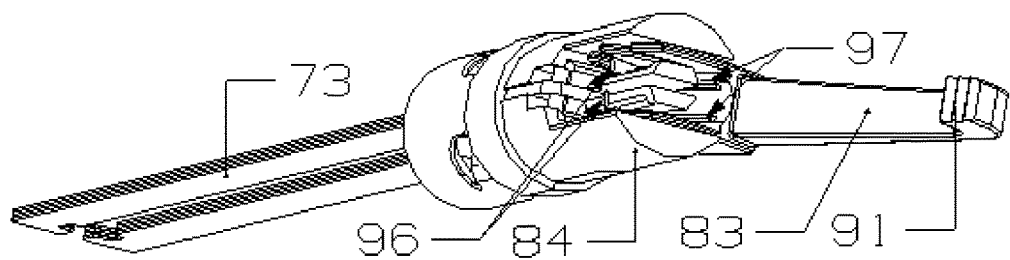
FIG. 58 is a perspective view showing the back of the position of FIG. 57.
Figure 59:
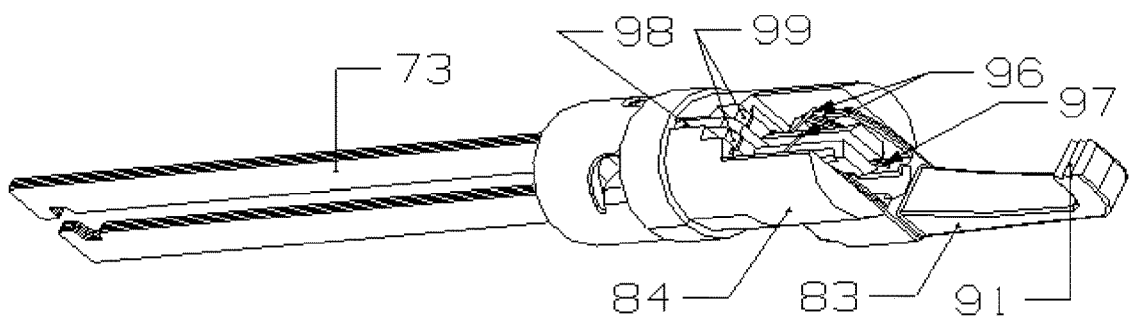
FIG. 59 is a perspective view showing a state in which the second interchangeable tool of FIG. 47 is partially removed from the tool holder.

During the process of mounting the second interchangeable tool 83 to the tool holder 84, step 1, the force of the second opening elastic part 97 is overcome to press it on the middle back part of the second interchangeable tool 83 toward the direction of the rotating support of the second interchangeable tool 83, and the mounting key 93 is inserted into the second mounting groove 89 through the opening of the second mounting groove 89, then the second interchangeable tool 83 is loosened (see FIG. 55 and FIG. 56); step 2, under the action of the second opening elastic part 97, the mounting key 93 rotates in the second mounting groove 89, so as to drive the second constraining key 92 of the second interchangeable tool 83 to rotate into the second constraining groove 95 of the tool holder 84, then the second interchangeable tool 83 is mounted on the tool holder 84 (see FIG. 57 and FIG. 58). During the process of removing the second interchangeable tool 83 from the tool holder 84, step 1, the force of the second opening elastic part 97 is overcome to press it on the front part of the second interchangeable tool 83 toward the direction of the rotating support of the second interchangeable tool 83, such that the mounting key 93 rotates in the second mounting groove 89, so as to drive the second constraining key 92 of the second interchangeable tool 83 to rotate out of the second constraining groove 95 of the tool holder 84 (see FIG. 55 and FIG. 56); step 2, the force of the second opening elastic part 97 located at the middle back part of the second interchangeable tool 83 pushes the second interchangeable tool 83 toward the opposite direction of the rotating support of the second interchangeable tool 83, so as to push the mounting key 93 out towards the opening of the second mounting groove 89 (see FIG. 59), then the second interchangeable tool 83 could be removed out of the tool holder 84.

The first inserting block 99 may move back and forth along the first tool slot 86 of the first interchangeable tool 82. The second inserting block 100 may move back and forth along the second tool slot 90 of the second interchangeable tool 83. When the operation assembly 53 controls the first inserting block 99 and the second inserting block 100 on the driving head 98 on the driving bar 73 to press on the first tool slot 86 of the first interchangeable tool 82 and the second tool slot 90 of the second interchangeable tool 83 to move forwards, the first opening elastic part 96 and the second opening elastic part 97 respectively keep that the first inserting block 99 and the second inserting block 100 on the driving head 98 are in contact with the first tool slot 86 of the first interchangeable tool 82 and the second tool slot 90 of the second interchangeable tool 83. The first inserting block 99 and the second inserting block 100 on the driving head 98 drive the first interchangeable tool 82 and the second interchangeable tool 83 to rotate towards the closing direction, respectively (see FIG. 48). When the operation assembly 53 controls the first inserting block 99 and the second inserting block 100 on the driving head 98 on the driving bar 73 to press on the first tool slot 86 of the first interchangeable tool 82 and the second tool slot 90 of the second interchangeable tool 83 to move backwards, the first opening elastic part 96 and the second opening elastic part 97 respectively keep that the first inserting block 99 and the second inserting block 100 on the driving head 98 are in contact with the first tool slot 86 of the first interchangeable tool 82 and the second tool slot 90 of the second interchangeable tool 83. The first inserting block 99 and the second inserting block 100 on the driving head 98 drive the first interchangeable tool 82 and the second interchangeable tool 83 to rotate towards the opening direction, respectively (see FIG. 47). When the first inserting block 99 and the second inserting block 100 on the driving head 98 on the driving bar 73 are moved to different locations on the first tool slot 86 of the first interchangeable tool 82 and the second tool slot 90 of the second interchangeable tool 83, the open/close angle between the first interchangeable tool 82 and the second interchangeable tool 83 is changed.

Figure 67:
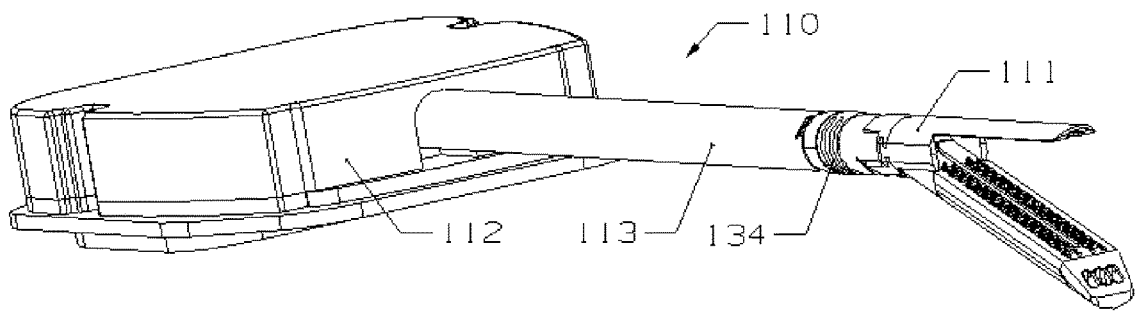
FIG. 67 shows a perspective view of a robotic multipurpose endoscopic surgical instrument according to the present disclosure.

FIG. 67 is a robotic multipurpose endoscopic surgical instrument 110 according to the present disclosure. The endoscopic surgical instrument 110 includes a tool assembly 111, a robotic operation assembly 112 and an elongated body 113. The elongated body 113 connects the operation assembly 112 and the tool assembly 111. The elongated body 113 includes an articulation component 134. The articulation component 134 is connected to the tool assembly 111 and the elongated body 113.

FIGS. 68-79 describe the tool assembly 111 and the driving member 126 according to the fifth embodiment. The tool assembly 111 includes an interchangeable tool 114 and a tool holder 115 (see FIG. 68). The interchangeable tool 114 includes a second replaceable part 116 and a first replaceable part 117. The first replaceable part 117 includes an anvil 118, a first tool slot 119, a first mounting key 120 and a second open-end mounting groove 121 (see FIG. 71). The second replaceable part 116 includes a staple cartridge 122, a second tool slot 123 and a second mounting key 124 (see FIG. 78). The second replaceable part 116 is mounted on the first replaceable part 117 by inserting the second mounting key 124 into the second mounting groove 121. The tool holder 115 includes a first open-end mounting groove 125 and a holder slot 135 (see FIG. 79). The first mounting groove 125 is inserted on the first mounting key 120 between the interchangeable tool 114 and the tool holder 115 to form a tool inlay connection (see FIG. 68). The operation assembly 112 includes a driving member 126. The operation assembly 112 controls the driving member 126 to move forward and backward in the tool assembly 111. The driving member 126 includes a first inserting block 127 at the front. The first inserting block 127 may move back and forth along the first tool slot 119 and the second tool slot 123 of the interchangeable tool 114. The driving member 126 includes a driving bar 128 and a driving head 129 (see FIG. 76 and FIG. 77). The driving bar 128 includes an inlay key 130. The driving head 129 includes a knife 131, an inlay groove 132 and a second inserting block 133. An inlay key 130 is inserted into the inlay groove 132 between the driving bar 128 and the driving head 129 to form a driving head inlay connection.

During the process of removing the interchangeable tool 114 from the tool holder 115, step 1, the operation assembly 112 controls the first inserting block 127 on the driving member 126 to move backwards along the first tool slot 119 and holder slot 135 until the first inserting block 127 on the driving member 126 retreats to the back of the first mounting groove 125 (see FIG. 69 and FIG. 70); step 2, the first mounting groove 125 is moved out of the first mounting key 120 from the tool inlay connection, then the interchangeable tool 114 can be removed from the tool holder 115. During the process of mounting the interchangeable tool 114 on the tool holder 115, step 1, the operation assembly 112 controls the first inserting block 127 on the driving member 126 to move backwards along the holder slot 135 until the first inserting block 127 on the driving member 126 retreats to the back of the first mounting groove 125 (see FIG. 69 and FIG. 70); step 2, the first mounting key 120 is inserted into the first mounting groove 125 to form the tool inlay connection (see FIG. 72); step 3, the operation assembly 112 controls the first inserting block 127 on the driving member 126 to move forwards along the holder slot 135 and insert into the first tool slot 119, such that the first inserting block 127 on the driving member 126 could prevent the first mounting groove 125 from moving out of the first mounting key 120 of the tool inlay connection, and the interchangeable tool 114 is mounted on the tool holder 115 (see FIG. 68 and FIG. 73).

Figure 68:
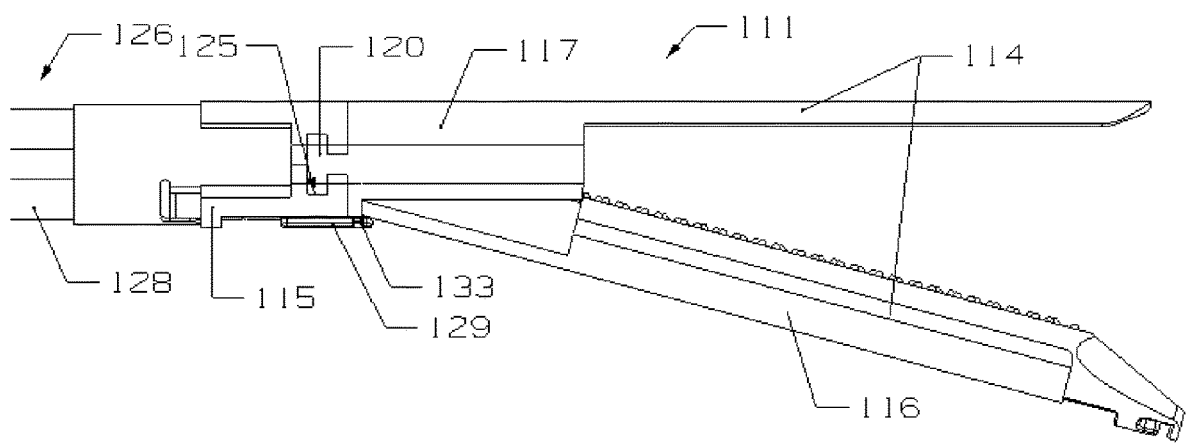
FIG. 68 is a front view of the tool assembly and driving member according to the fifth embodiment of the present disclosure.
Figure 69:
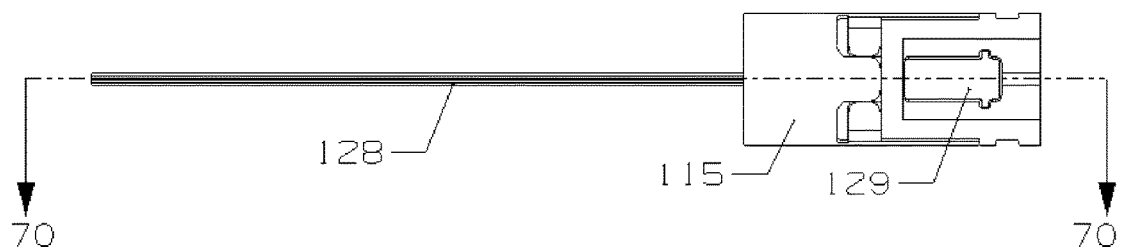
Figure 70:
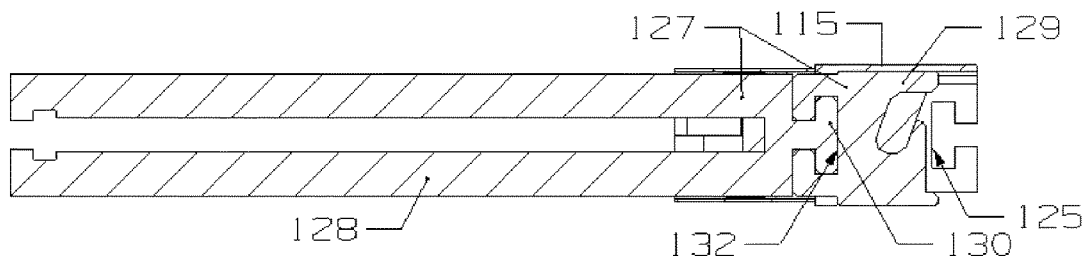
FIG. 70 is a section view of the 70-70 profile of FIG. 69.
Figure 71:
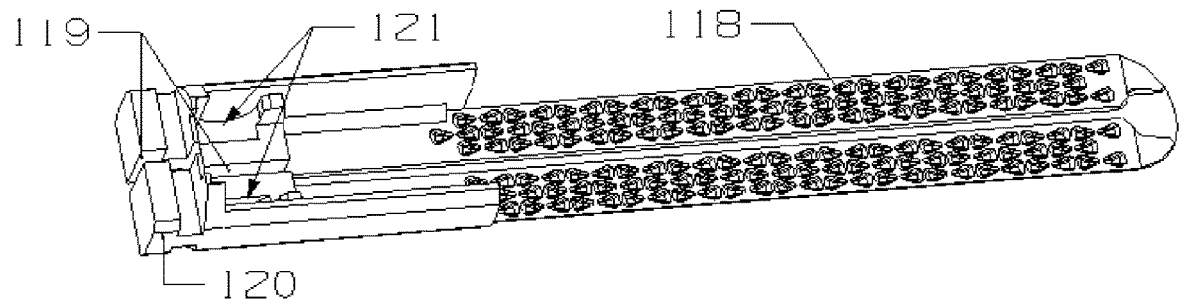
FIG. 71 is a perspective view showing the replaceable holder of FIG. 68.
Figure 72:
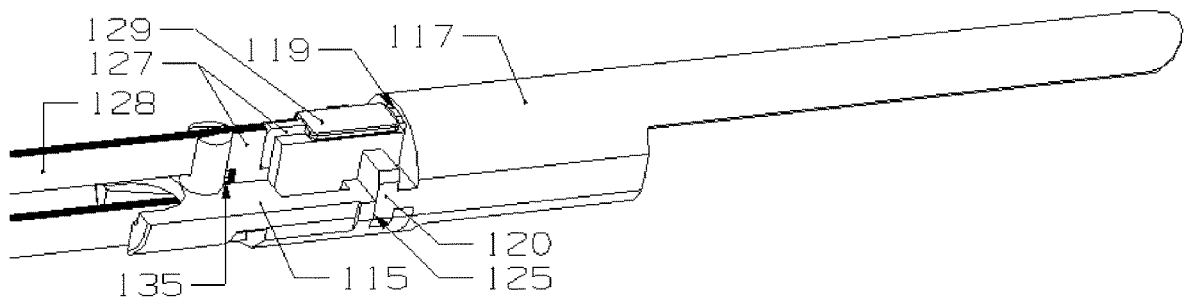
FIG. 72 is a perspective view showing that the replaceable holder of FIG. 68 is inlaid on the tool holder (some parts are removed)
Figure 73:
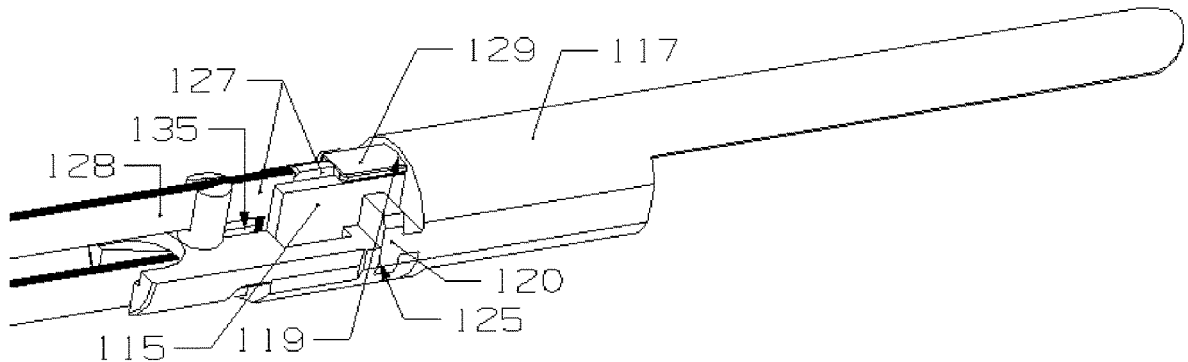
FIG. 73 is a perspective view showing that the replaceable holder of FIG. 68 is mounted on the tool holder (some parts are removed)
Figure 74:
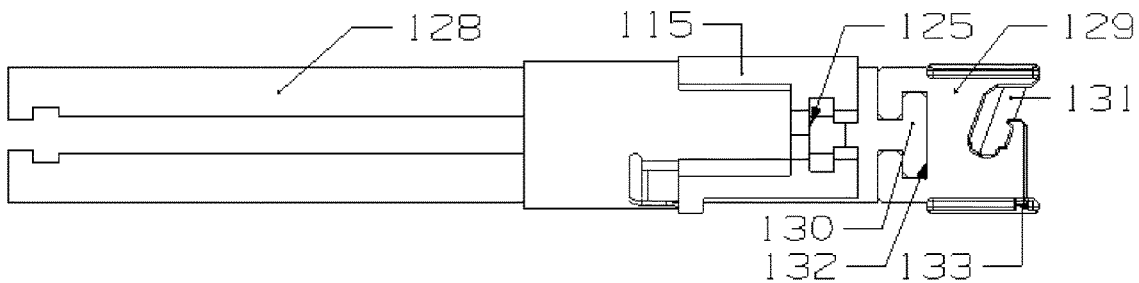
FIG. 74 is a front view showing that the driving head of FIG. 68 extends out of the tool holder.
Figure 81:
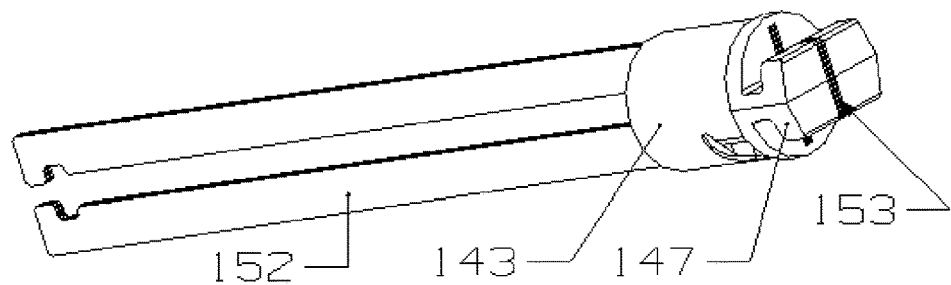
FIG. 81 is a perspective view showing the tool holder and driving bar.
Figure 82:
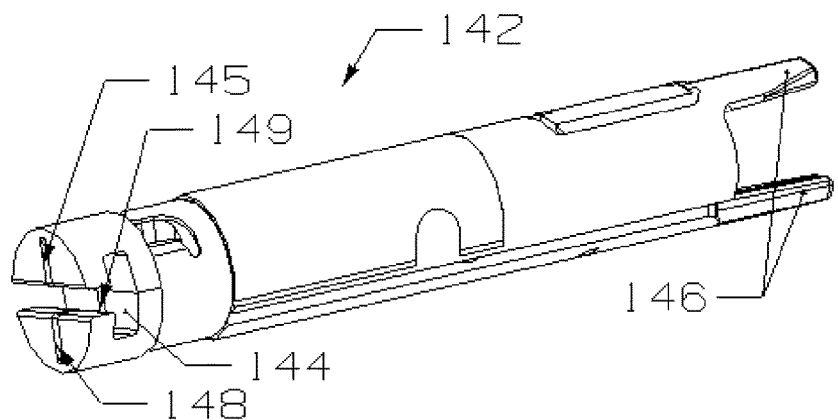
FIG. 82 is a perspective view showing the interchangeable tool and driving head.
Figure 83:
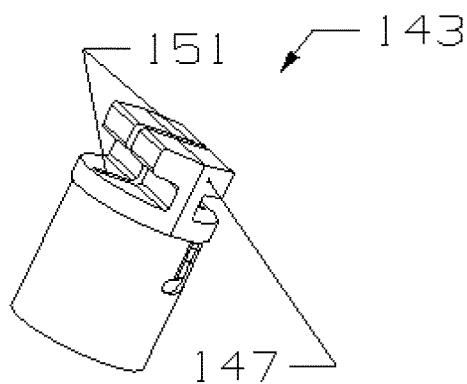
FIG. 83 is a perspective view showing the tool holder of FIG. 81.
Figure 84:
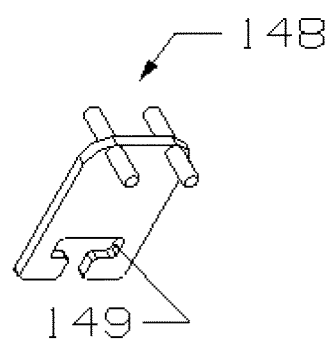
FIG. 84 is a perspective view showing the driving head of FIG. 82.
Figure 85:
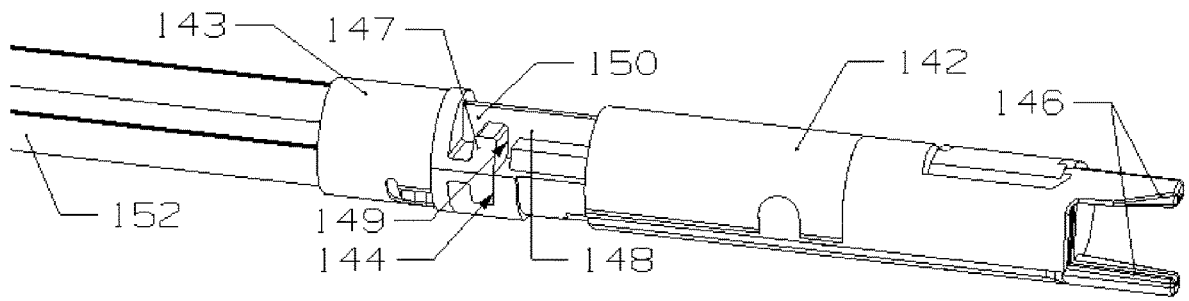
FIG. 85 is a perspective view showing that the tool holder and the driving member of FIG. 80 are in a state in which the inlay connection may be inserted on or removed from the interchangeable tool (some parts are removed) and the driving head.
Figure 86:
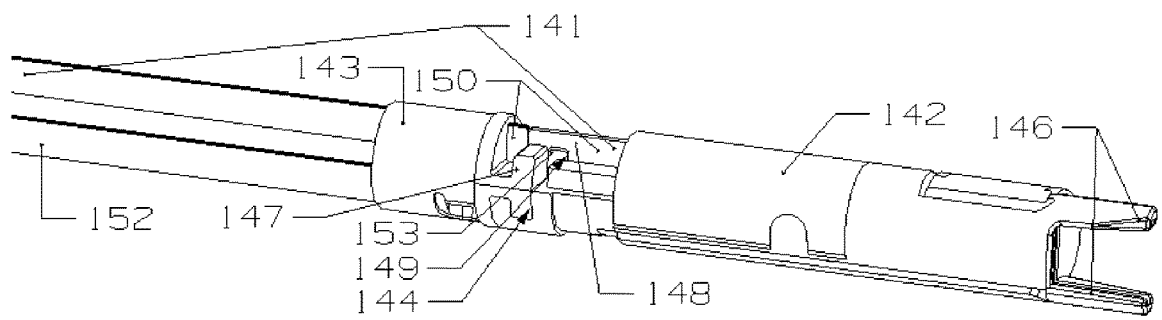
FIG. 86 is a perspective view showing that the interchangeable tool (some parts are removed) and the driving head of FIG. 81 are mounted on the tool holder and the driving bar.

During the process of mounting the second replaceable part 116 on the first replaceable part 117, step 1, the second mounting key 124 is inserted into the second mounting groove 121 through the opening of the second mounting groove 121, and the second replaceable part 116 is inserted on the first replaceable part 117; step 2, the second inserting block 133 moves forwards along the second tool slot 123 and is inserted into the second replaceable part 116 to prevent the second mounting key 124 from moving out of the opening of the second mounting groove 121, then the second replaceable part 116 is mounted on the first replaceable part 117 (see FIG. 68). During the process of removing the second replaceable part 116 from the first replaceable part 117, step 1, the second inserting block 133 moves backwards along the second tool slot 123 of the second replaceable part 116 to exit the second replaceable part 116; step 2, the second mounting key 124 is removed from the opening of the second mounting groove 121, and the second replaceable part 116 can be removed from the first replaceable part 117.

The staple cartridge 122 and the anvil 118 in the interchangeable tool 114 and the knife 131 on the driving head 129 may be used to cut and staple tissue. In the use of the endoscopic surgical instrument 110, if the knife 131 on the driving head 129 is found to be damaged, a spare driving head 129 may be selected to replace the in-use driving head 129. During the process of replacing the in-use driving head 129, step 1, the operation assembly 112 controls the in-use driving head 129 on the driving bar 128 to move backward, then the interchangeable tool 114 moves out of the tool holder 115; step 2, the operation assembly 112 controls the in-use driving head 129 on the driving bar 128 to move forward until the in-use driving head 129 extends out of the tool holder 115 (see FIG. 74), and the inlay key 130 removes from the inlay groove 132 in the driving head inlay connection, then the in-use driving head 129 could be removed from the driving bar 128 (see FIG. 75); step 3, the inlay key 130 is inserted into the inlay groove 132 between the driving bar 128 and the spare driving head 129 to form the driving head inlay connection, and the spare driving head 129 can be installed on the driving bar 128 (see FIG. 74); step 4, the operation assembly 112 controls the spare driving head 129 on the driving bar 128 to move backward until the spare driving head 129 returns to the tool holder 115; step 5, the interchangeable tool 114 is installed on the tool holder 115.

After the endoscopic surgical instrument 110 is used, according to the requirements of endoscopic surgery, the interchangeable tool with the same specification may be replaced; the interchangeable tool with a different specification may also be replaced; or tools with other functions may also be replaced.

FIGS. 80-86 describe the tool assembly 140 and driving member 141 according to the sixth embodiment. The tool assembly 140 includes an interchangeable tool 142 and a tool holder 143 (see FIG. 80). The interchangeable tool 142 includes an open-end mounting groove 144, a tool slot 145 and a clip applier 146 (see FIG. 82). The tool holder 143 includes a mounting key 147 and a holder slot 151 (see FIG. 83). The mounting key 147 is inserted into the mounting groove 144 between the interchangeable tool 142 and the tool holder 143 to form a tool inlay connection (see FIG. 80). The driving member 141 includes a driving bar 152 and a driving head 148. An inlay key 153 is inserted into the inlay groove 149 between the driving bar 152 and the driving head 148 to form a driving head inlay connection (see FIG. 86). The position of the tool inlay connection is aligned to the position of the driving head inlay connection to form a replaceable inlay connection that may be inserted or removed (see FIG. 85). The driving member 141 includes an inserting block 150 at the front part (see FIG. 86). The inserting block 150 may move back and forth along the tool slot 145 and the holder slot 151. During the process of removing the interchangeable tool 142 from the tool holder 143 and removing the driving head 148 from the driving bar 152, step 1, the operation assembly 112 controls the inserting block 150 on the driving member 141 to move backwards along the tool slot 145 and the holder slot 151, and aligns the position of the tool inlay connection between the mounting key 147 and the mounting groove 144 with the position of the driving head inlay connection between the inlay key 153 and the inlay groove 149 (see FIG. 85); step 2, the mounting groove 144 and the inlay groove 149 (see FIG. 82) are removed from the mounting key 147 and the inlay key 153 from the aligned tool inlay connection and driving head inlay connection at the same time (see FIG. 81), then the interchangeable tool 142 can be removed from the tool holder 143 and the driving head 148 can be removed from the driving bar 152 at the same time. During the process of mounting the interchangeable tool 142 to the tool holder 143 and mounting the driving head 148 to the driving bar 152, step 1, the operation assembly 112 controls the driving bar 152 to move backwards until the driving bar 152 retreats to the position where the position of the tool inlay connection between the mounting key 147 and the mounting groove 144 is aligned with the position of the driving head inlay connection between the inlay key 153 and the inlay groove 149; step 2, the aligned mounting groove 144 and inlay groove 149 (see FIG. 82) are inserted on the aligned mounting key 147 and inlay key 153 simultaneously (see FIG. 81) to form the aligned tool inlay connection and driving head inlay connection (see FIG. 85); step 3, the operation assembly 112 controls the inserting block 150 on the driving member 141 to move forwards along the holder slot 151 to insert into the tool slot 145 of the interchangeable tool 142, such that the inserting block 150 on the driving member 141 prevents the mounting key 147 from moving out of the mounting groove 144 of the tool inlay connection, and the interchangeable tool 142 is mounted on the tool holder 143; at the same time, the tool slot 145 and the holder slot 151 prevent the inlay key 130 from moving out of the inlay groove 149 of the driving head inlay connection, and the driving head 148 is mounted on the driving bar 128 (see FIG. 80 and FIG. 86).

After the endoscopic surgical instrument 110 is used, according to the requirements of endoscopic surgery, the interchangeable tool with the same specification may be replaced; the interchangeable tool with a different specification may be replaced; tools with other functions may also be replaced.

Figure 87:
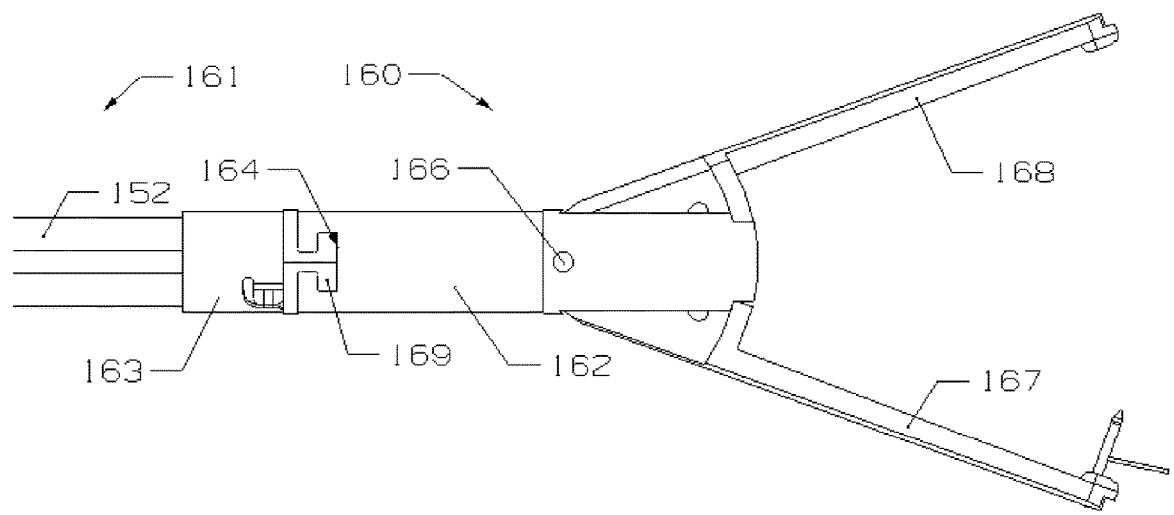
FIG. 87 is a front view showing the first type of interchangeable tool, the tool holder and the driving member according to the seventh embodiment of the present disclosure.
Figure 88:
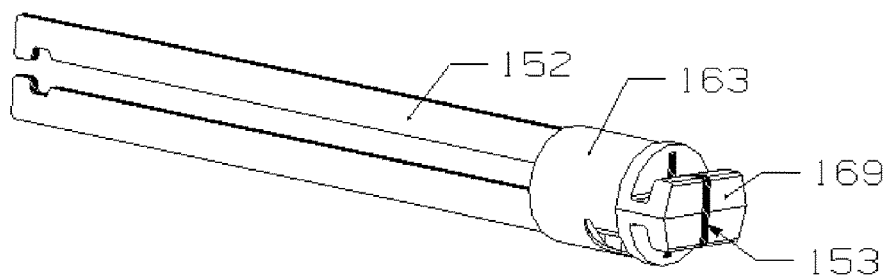
FIG. 88 is a perspective view showing the tool holder and driving bar of FIG. 87.
Figure 89:
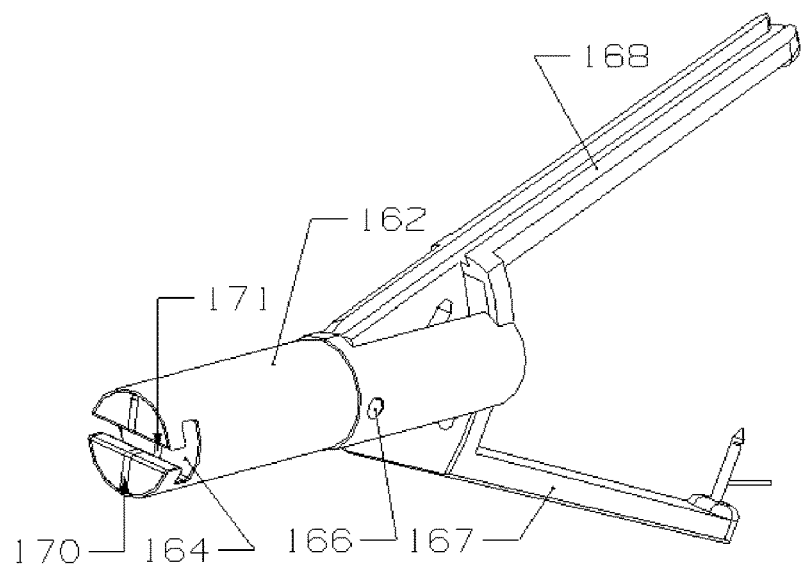
FIG. 89 is a perspective view showing the first type of interchangeable tool and driving head of FIG. 87.
Figure 90:
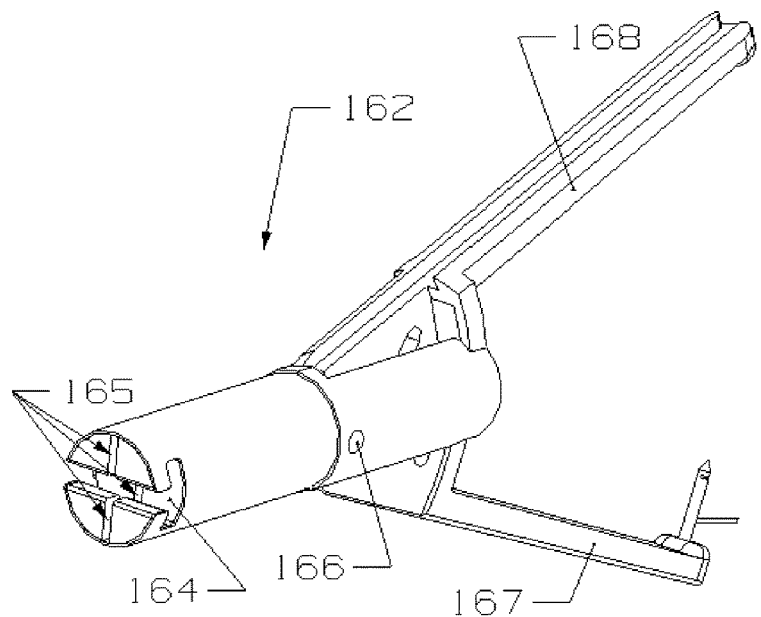
FIG. 90 is a perspective view showing the first type of interchangeable tool of FIG. 89.
Figure 91:
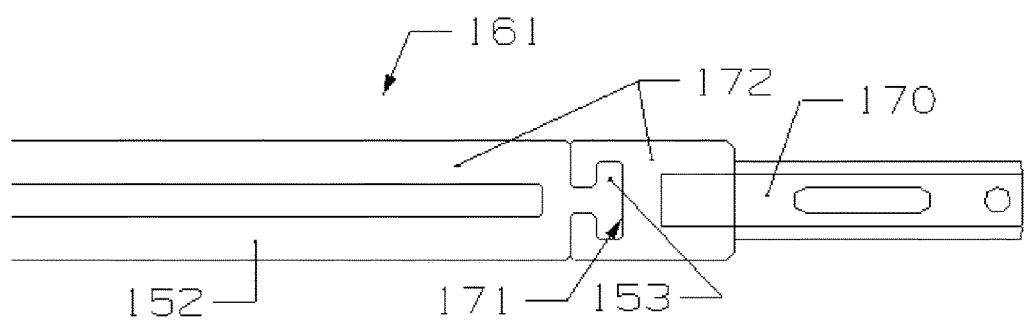
FIG. 91 is a partial front view of the driving member of FIG. 87.
Figure 96:
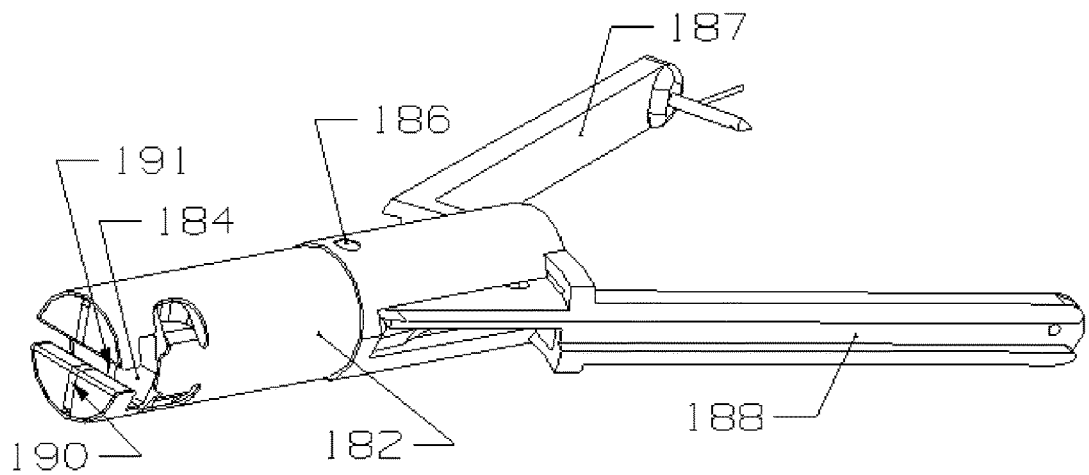
FIG. 96 is a perspective view showing the second type of interchangeable tool and driving head of FIG. 95.
Figure 97:
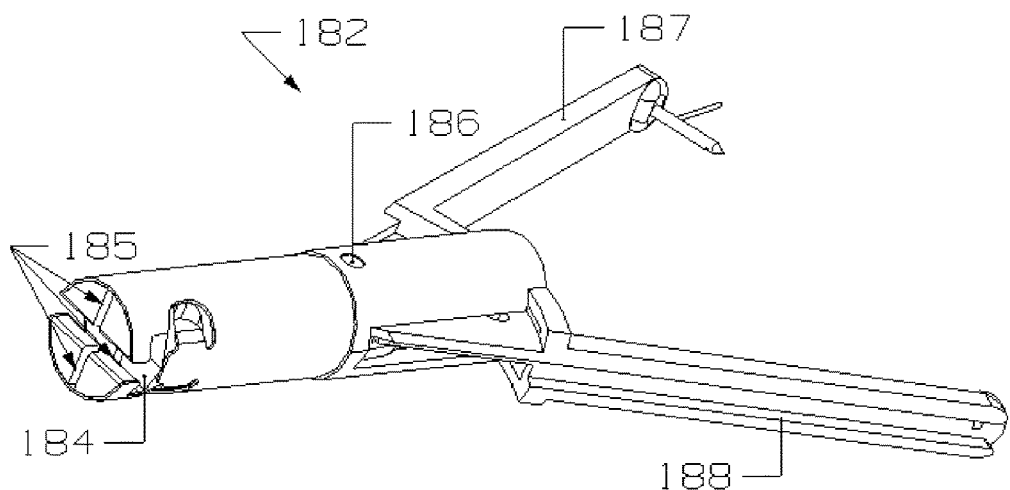
FIG. 97 is a perspective view of the second type of interchangeable tool of FIG. 95.
Figure 98:
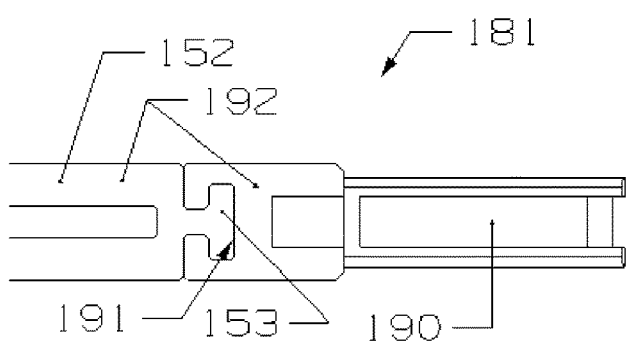
FIG. 98 is a partial front view of the driving member of FIG. 95.
Figure 99:
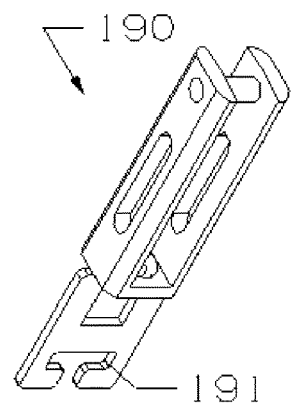
FIG. 99 is a perspective view of the driving head of FIG. 98.
Figure 100:
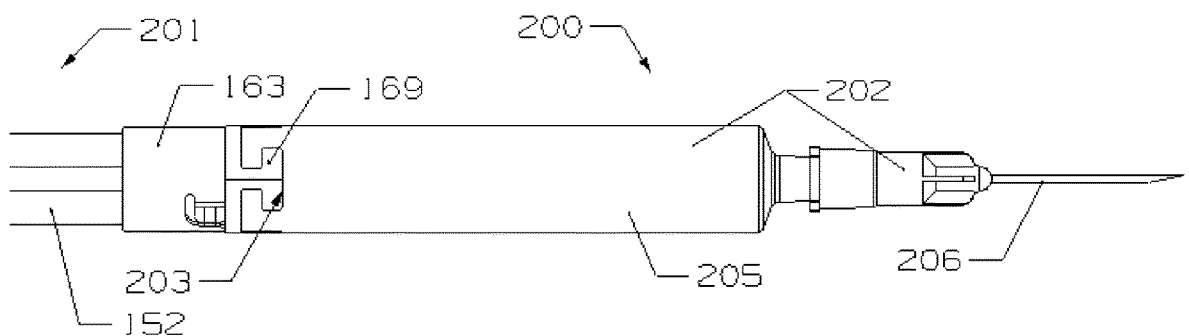
FIG. 100 is a front view of the tool assembly and driving member according to the eighth embodiment of the present disclosure.
Figure 101:
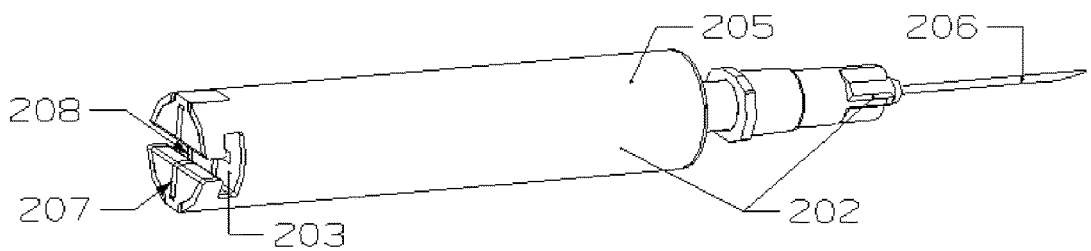
FIG. 101 is a perspective view showing the interchangeable tool and driving head of FIG. 100.
Figure 102:
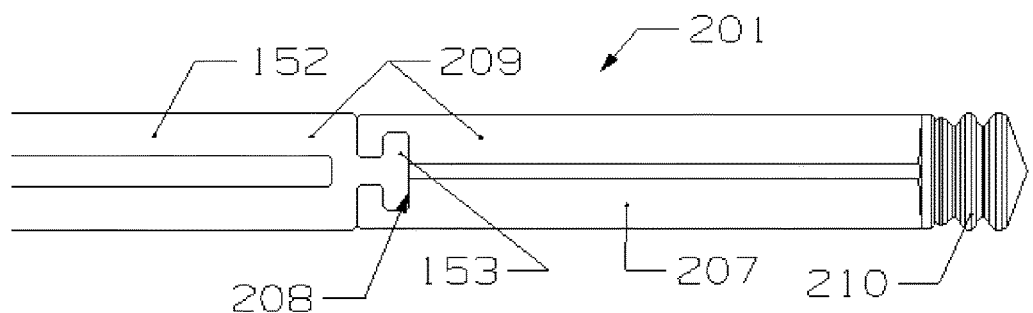
FIG. 102 is a partial front view of the driving member of FIG. 100.
Figure 103:
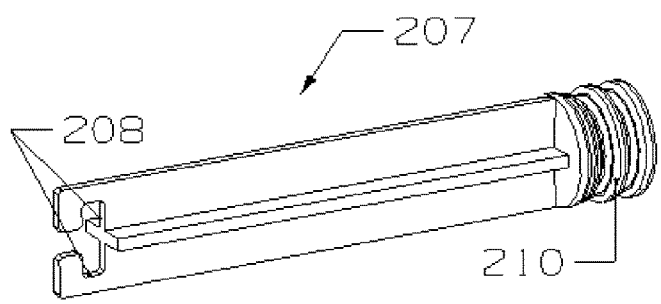
FIG. 103 is a perspective view of the driving head of FIG. 102.
Figure 104:
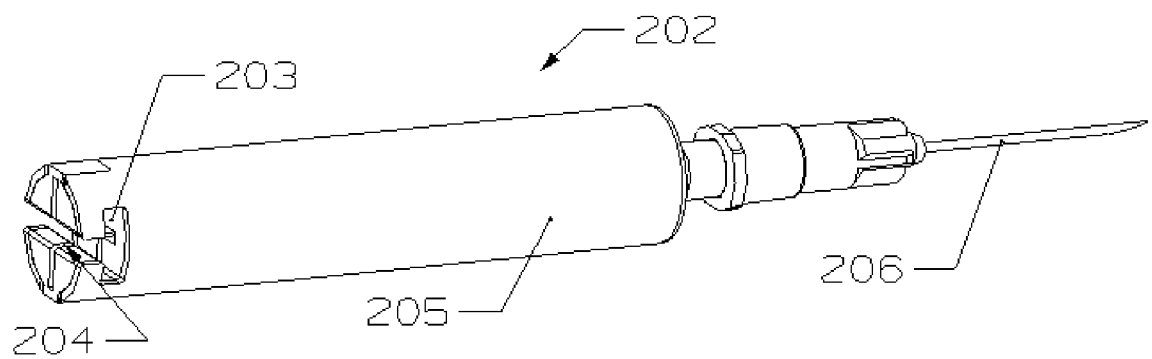
FIG. 104 is a perspective view of the interchangeable tool of FIG. 101.
Figure 105:
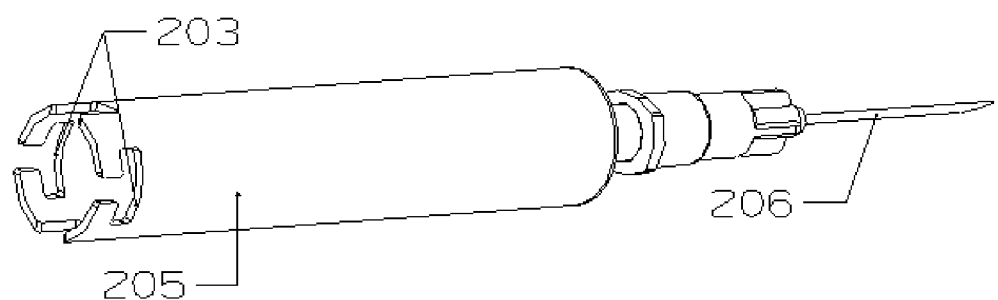
FIG. 105 is a perspective view of the syringe barrel and needle of FIG. 104.

FIGS. 87-99 describe the tool assembly and the driving member according to the seventh embodiment. The tool assembly 160 includes a first type of interchangeable tool 162 and a tool holder 163 (see FIG. 87). The first type of interchangeable tool 162 includes an open-end mounting groove 164, a tool slot 165, a first type of pivot 166 and first tools 167 and 168 (see FIG. 90). The tool holder 163 includes a mounting key 169 and a holder slot 151 (see FIG. 94). The mounting key 169 is inserted into the mounting groove 164 between the first type of interchangeable tool 162 and the tool holder 163 to form a tool inlay connection (see FIG. 87). The driving member 161 includes a driving bar 152 and a driving head 170. An inlay key 153 is inserted into the inlay groove 171 between the driving bar 152 and the driving head 170 to form a driving head inlay connection (see FIGS. 91-93). The position of the tool inlay connection is aligned to the position of the driving head inlay connection to form a replaceable inlay connection that may be inserted or removed. The driving member 161 includes an inserting block 172 at the front. The inserting block 172 may move back and forth along the tool slot 165 and the holder slot 151. When the driving head 170 moves back and forth within the first type of interchangeable tool 162, the first tools 167 and 168 respectively rotate around the first type of pivot 166 to achieve the opening and closing actions of the first tools 167 and 168. During the process of removing the first type of interchangeable tool 162 from the tool holder 163 and removing the driving head 170 from the driving bar 152, step 1, the operation assembly 112 controls the inserting block 172 on the driving member 161 to move backwards along the tool slot 165 and the holder slot 151 and aligns the position of the tool inlay connection between the mounting key 169 and the mounting groove 164 with the position of the driving head inlay connection between the inlay key 153 and the inlay groove 171; step 2, the mounting groove 164 and the inlay groove 171 (see FIG. 89) are removed from the mounting key 169 and the inlay key 153 from the aligned tool inlay connection and driving head inlay connection at the same time (see FIG. 88), then the first type of interchangeable tool 162 can be removed from the tool holder 163 and the driving head 170 can be removed from the driving bar 152 at the same time. During the process of mounting the first type of interchangeable tool 162 to the tool holder 163 and mounting the driving head 170 to the driving bar 152, step 1, the operation assembly 112 controls the driving bar 152 to move backwards until the driving bar 152 retreats to the position where the position of the tool inlay connection between the mounting key 169 and the mounting groove 164 is aligned with the position of the driving head inlay connection between the inlay key 153 and the inlay groove 171; step 2, the aligned mounting groove 164 and inlay groove 171 (see FIG. 89) are inserted on the aligned mounting key 169 and inlay key 153 simultaneously (see FIG. 88) to form the aligned tool inlay connection and driving head inlay connection; step 3, the operation assembly 112 controls the inserting block 172 on the driving member 161 to move forwards along the holder slot 151 to insert into the tool slot 165, such that the inserting block 172 on the driving member 161 prevents the mounting key 169 from moving out of the mounting groove 164 of the tool inlay connection, and the first type of interchangeable tool 162 is mounted on the tool holder 163 (see FIG. 87); at the same time, the tool slot 165 and the holder slot 151 prevent the inlay key 153 from moving out of the inlay groove 171 of the driving head inlay connection, then the driving head 170 is mounted on the driving bar 152 (see FIG. 91).

The tool assembly 180 may also adopt a second type of interchangeable tool 182 and a tool holder 163 (see FIG. 95). The second type of interchangeable tool 182 includes an open-end mounting groove 184, a tool slot 185, a second type of pivot 186 and second tools 187 and 188 (see FIG. 97). The mounting key 169 is inserted into the mounting groove 184 between the second type of interchangeable tool 182 and the tool holder 163 to form a tool inlay connection (see FIG. 95). The driving member 181 includes a driving bar 152 and a driving head 190. An inlay key 153 is inserted into the inlay groove 191 between the driving bar 152 and the driving head 190 to form a driving head inlay connection (see FIG. 98 and FIG. 99). The position of the tool inlay connection is aligned to the position of the driving head inlay connection to form a replaceable inlay connection that may be inserted or removed. The driving member 181 includes an inserting block 192 at the front. The inserting block 192 may move back and forth along the tool slot 185 and the holder slot 151. When the driving head 190 moves back and forth within the second type of interchangeable tool 182, the second tools 187 and 188 respectively rotate around the second type of pivot 186 to achieve the opening and closing actions of the second tools 187 and 188. During the process of removing the second type of interchangeable tool 182 from the tool holder 163 and removing the driving head 190 from the driving bar 152, step 1, the operation assembly 112 controls the inserting block 192 on the driving member 181 to move backwards along the tool slot 185 and the holder slot 151 and aligns the position of the tool inlay connection between the mounting key 169 and the mounting groove 184 with the position of the driving head inlay connection between the inlay key 153 and the inlay groove 191; step 2, the mounting groove 184 and the inlay groove 191 (see FIG. 96) are removed from the mounting key 169 and the inlay key 153 from the aligned tool inlay connection and driving head inlay connection at the same time (see FIG. 88), then the second type of interchangeable tool 182 can be removed from the tool holder 163 and the driving head 190 can be removed from the driving bar 152 at the same time. During the process of mounting the second type of interchangeable tool 182 to the tool holder 163 and mounting the driving head 190 to the driving bar 152, step 1, the operation assembly 112 controls the driving bar 152 to move backwards until the driving bar 152 retreats to the position where the position of the tool inlay connection between the mounting key 169 and the mounting groove 184 is aligned with the position of the driving head inlay connection between the inlay key 153 and the inlay groove 191; step 2, the aligned mounting groove 184 and inlay groove 191 (see FIG. 96) are inserted on the aligned mounting key 169 and inlay key 153 simultaneously (see FIG. 88) to form the aligned tool inlay connection and driving head inlay connection; step 3, the operation assembly 112 controls the inserting block 192 on the driving member 181 to move forwards along the holder slot 151 to insert into the tool slot 185, such that the inserting block 192 on the driving member 181 prevents the mounting key 169 from moving out of the mounting groove 184 of the tool inlay connection, then the second type of interchangeable tool 182 is mounted on the tool holder 163; at the same time, the tool slot 185 and the holder slot 151 prevent the inlay key 153 from moving out of the inlay groove 191 of the driving head inlay connection, then the driving head 190 is mounted on the driving bar 128 (see FIG. 95).

Due to that after the first type of interchangeable tool 162 of the seventh embodiment is mounted on the tool holder 163, the axis direction of the first type of pivot 166 (see FIG. 87) forms an angle with the axis direction of the second type of pivot 186 after the second type of interchangeable tool 182 is mounted on the tool holder 163 (see FIG. 95), so when the articulation component 134 of the endoscopic surgical instrument 110 rotates in the same plane, the open/close direction of the first tools 167 and 168 of the first type of interchangeable tool 162 forms an angle with the open/close direction of the second tools 187 and 188 of the second type of interchangeable tool 182. Therefore, according to the requirements of endoscopic surgeries on the open/close direction of the tool, the first type of interchangeable tool 162 or the second type of interchangeable tool 182 may be selected to be mounted on the tool holder 163, thereby increasing the scope of the endoscopic surgeries.

FIGS. 100-105 describe the tool assembly 200 and the driving member 201 according to the eighth embodiment. The tool assembly 200 includes an interchangeable tool 202 and a tool holder 163 (see FIG. 100). The interchangeable tool 202 includes an open-end mounting groove 203, a tool slot 204, a syringe barrel 205 and a needle 206 (see FIG. 104 and FIG. 105). The needle 206 is inserted tightly at the front end of the syringe barrel 205. The mounting key 169 is inserted into the mounting groove 203 between the interchangeable tool 202 and the tool holder 163 to form a tool inlay connection (see FIG. 100). The driving member 201 includes a driving bar 128 and a driving head 207. An inlay key 153 is inserted into the inlay groove 208 between the driving bar 152 and the driving head 207 to form a driving head inlay connection (see FIG. 102 and FIG. 103). The position of the tool inlay connection is aligned to the position of the driving head inlay connection to form a replaceable inlay connection that may be inserted or removed. The driving member 201 includes an inserting block 209 at the front. The inserting block 209 may move back and forth along the tool slot 204 of the interchangeable tool 202. The driving head 207 includes a piston 210 at the front part. When the piston 210 of the driving head 207 moves back and forth in the syringe barrel 205 of the interchangeable tool 202, the injection operation is performed.

During the process of removing the interchangeable tool 202 from the tool holder 163 and removing the driving head 207 from the driving bar 152, step 1, the operation assembly 112 controls the inserting block 209 on the driving member 201 to move backwards along the tool slot 204 of the interchangeable tool 202 and aligns the position of the tool inlay connection between the mounting key 169 and the mounting groove 203 with the position of the driving head inlay connection between the inlay key 153 and the inlay groove 208; step 2, the mounting groove 203 and the inlay groove 208 (see FIG. 101) are moved out of the mounting key 169 and the inlay key 153 from the aligned tool inlay connection and driving head inlay connection at the same time (see FIG. 88), then the interchangeable tool 202 can be moved out of the tool holder 163 and the driving head 207 can be moved out of the driving bar 152 at the same time. During the process of mounting the interchangeable tool 202 to the tool holder 163 and mounting the driving head 207 to the driving bar 152, step 1, the operation assembly 112 controls the driving bar 152 to move backwards until the driving bar 152 retreats to the position where the position of the tool inlay connection between the mounting key 169 and the mounting groove 203 is aligned with the position of the driving head inlay connection between the inlay key 153 and the inlay groove 208; step 2, the aligned mounting groove 203 and inlay groove 208 (see FIG. 101) are inserted on the aligned mounting key 169 and inlay key 153 simultaneously (see FIG. 88) to form the aligned tool inlay connection and driving head inlay connection; step 3, the operation assembly 112 controls the inserting block 209 on the driving member 201 to move forwards to insert into the tool slot 204 of the interchangeable tool 202, such that the inserting block 209 on the driving member 201 prevents the mounting key 169 from moving out of the mounting groove 203 of the tool inlay connection, and the interchangeable tool 202 is mounted on the tool holder 163; at the same time, the tool slot 204 of the interchangeable tool 202 prevents the inlay key 153 from moving out of the inlay groove 208 of the driving head inlay connection, and the driving head 207 is mounted on the driving bar 152 (see FIG. 100).

Figure 106:
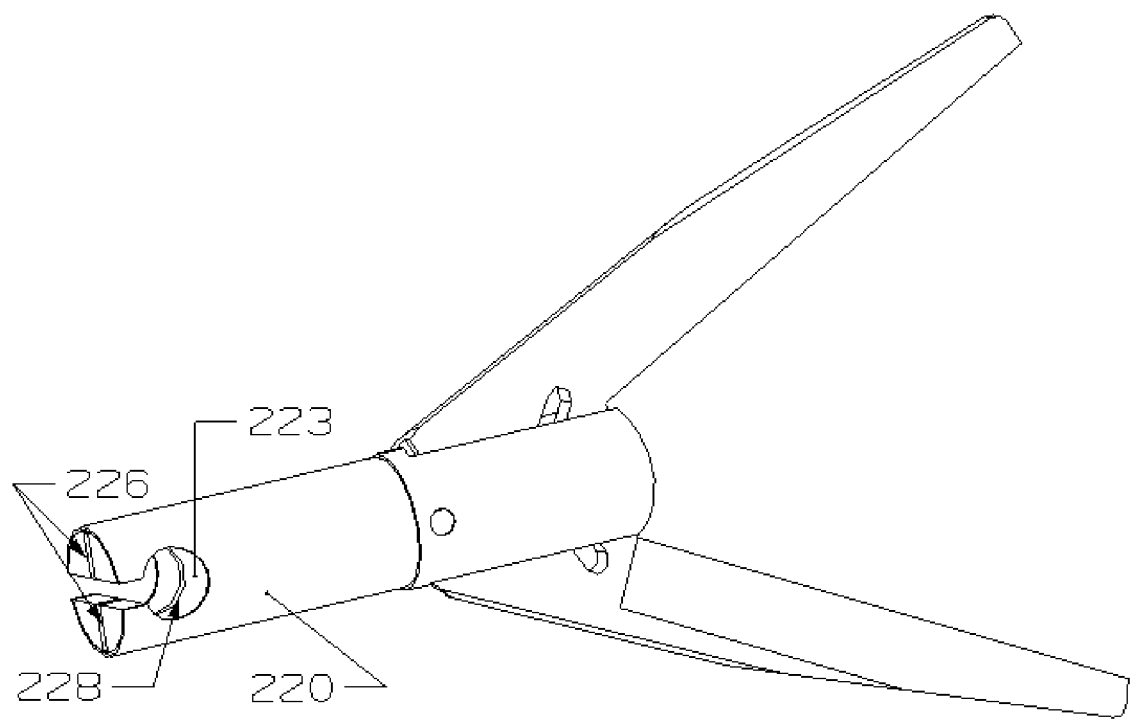
FIG. 106 is a perspective view showing the interchangeable tool, the driving head and the circular inlay groove thereof.
Figure 107:
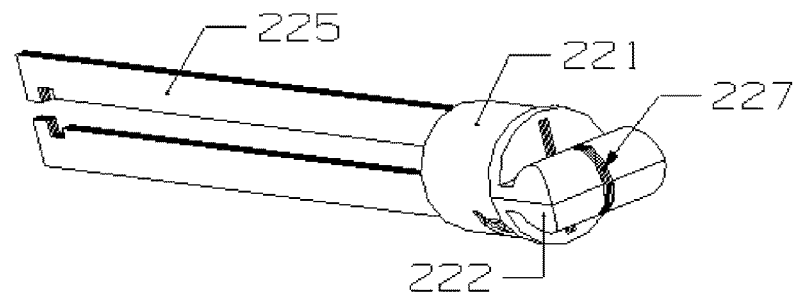
FIG. 107 is a perspective view showing the tool holder and driving bar that may form the inlay connection of FIG. 106.

As shown in FIG. 106 and FIG. 107, a circular mounting key 222 may also be inserted into the opening mounting groove 223 between the interchangeable tool 220 and the tool holder 221 to form a tool inlay connection. A circular inlay key 227 may also be inserted into the opening inlay groove 228 between the driving bar 225 and the driving head 226 to form a driving head inlay connection.

Figure 108:
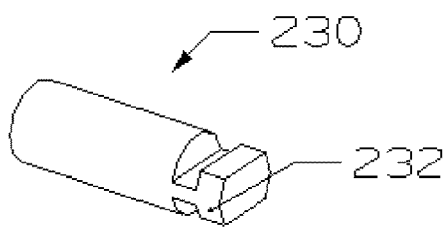
FIG. 108 is a perspective view of the cylindrical driving bar and the inlay block thereof.
Figure 109:
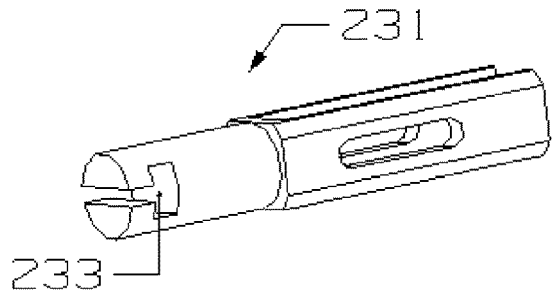
FIG. 109 is a perspective view showing the driving head that may form the inlay connection of FIG. 108.

As shown in FIG. 108 and FIG. 109, an inlay key 232 may also be inserted into the opening inlay groove 233 between the cylindrical driving bar 230 and the cylindrical driving head 231 to form a driving head inlay connection. This type of driving head inlay connection is particularly suitable for endoscopic surgical instruments with a tool assembly with an electric operation assembly.

Figure 110:
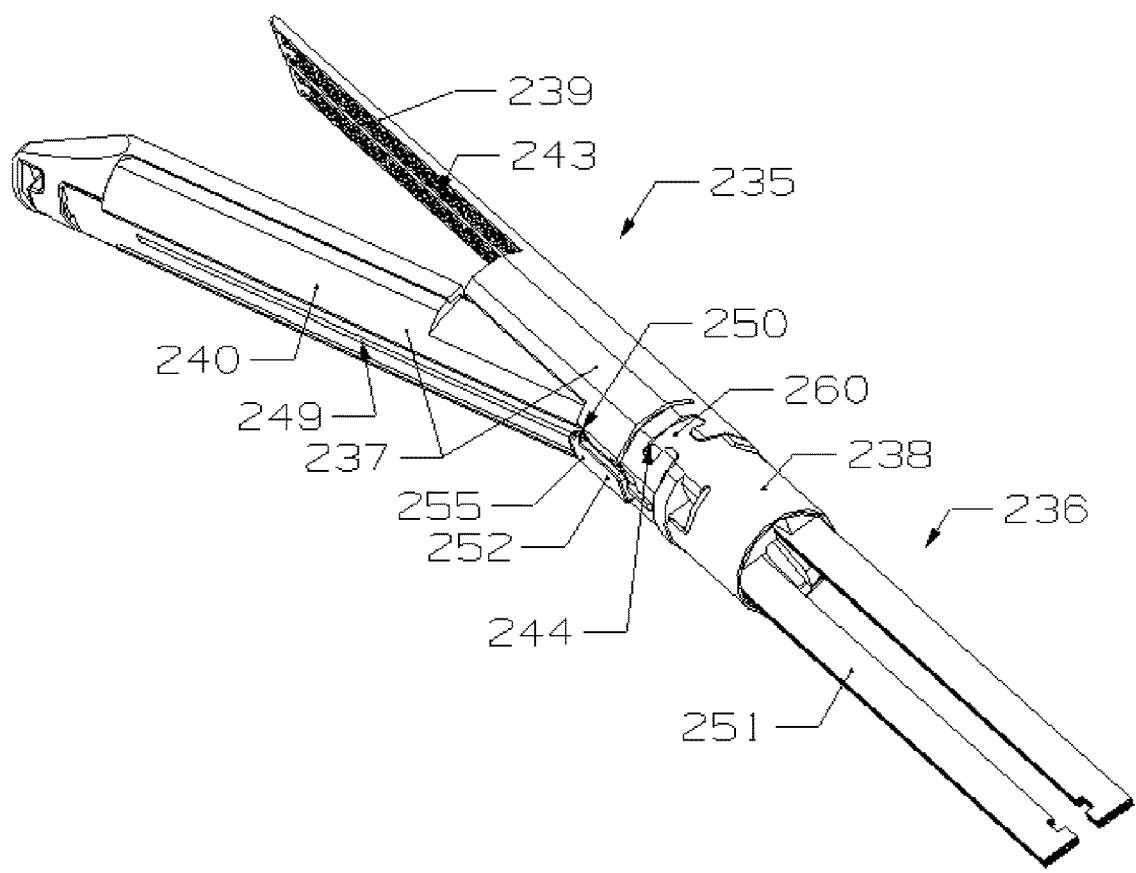
FIG. 110 is a perspective view of the mounted tool assembly and driving member according to the ninth embodiment of the present disclosure.
Figure 122:
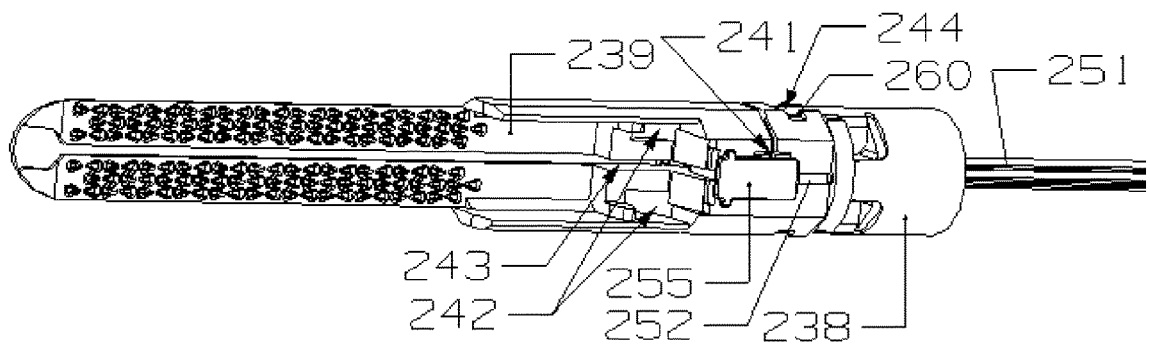
Figure 125:
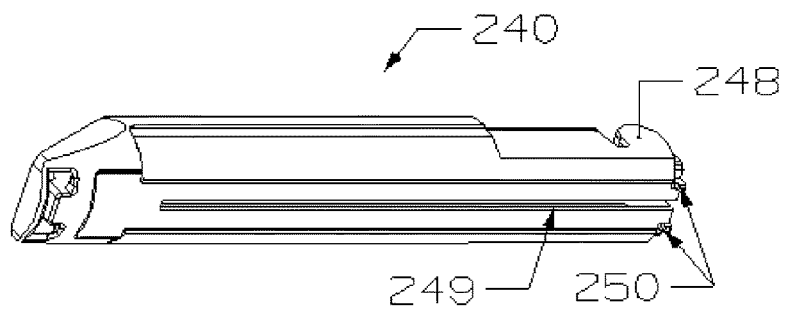
Figure 126:
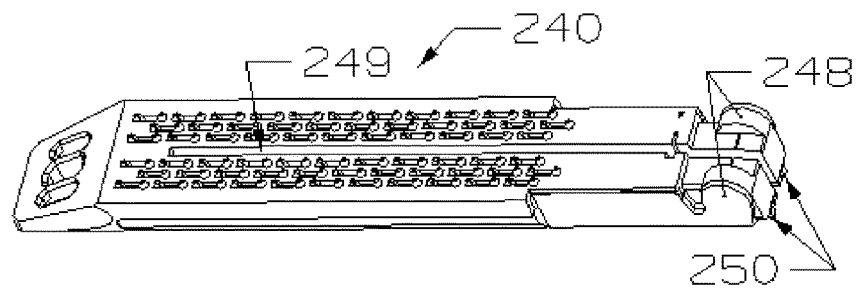
Figure 127:
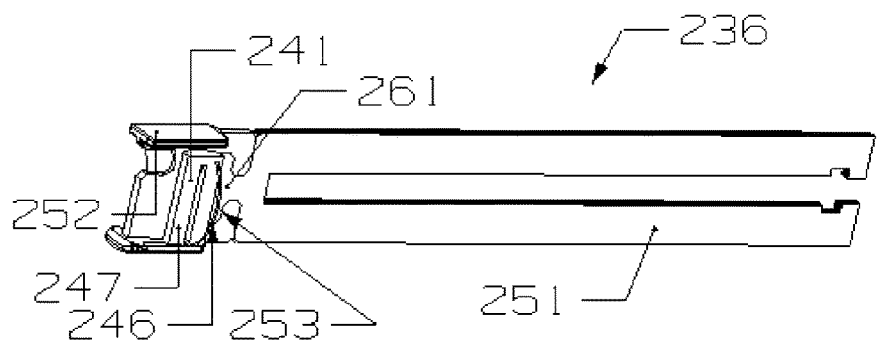

FIGS. 110-129 describe the tool assembly 235 and the driving member 236 according to the ninth embodiment of the present disclosure. The driving member 236 may move forward and backward in the tool assembly 235. The driving member 236 participates in controlling the actions of the tool assembly 235. The tool assembly 235 includes an interchangeable tool 237 and a tool holder 238 (see FIG. 110). The interchangeable tool 237 includes a straight replaceable anvil 239, a straight staple cartridge 240 and a locating elastic part 241 (see FIG. 110 and FIG. 115). The straight replaceable anvil 239 includes an opening groove 242, a tool slot 243 in a forward-backward direction and an open-end mounting groove 244 located at the back part (see FIGS. 113-115). A spring groove 245 (see FIG. 113) is provided in a side surface of the tool slot 243 of the straight replaceable anvil 239. One part of the locating elastic part 241 has a spring 246 and a positioning part 247 (see FIG. 117). The locating elastic part 241 is mounted in the spring groove 245 (see FIG. 114). The spring 246 acts on the positioning part 247. The spring groove 245 prevents the locating elastic part 241 from moving back and forth within the straight replaceable anvil 239. The straight staple cartridge 240 includes a key 248, a staple cartridge slot 249 in a forward-backward direction and a constraining key 250 located at the back part (see FIG. 125 and FIG. 126). The key 248 is inserted into the groove 242 between the straight replaceable anvil 239 and the straight staple cartridge 240 to form a rotating support of the straight staple cartridge. The driving member 236 includes a driving bar 251 and a straight driving head 252 (see FIG. 120). The straight driving head 252 includes an open-end inlay groove 253 at the back part, an upper beam 254 at the upper end, a lower beam 255 at the lower end, a constraining groove 256 at a side surface and a knife 257 at the front part (see FIG. 116, FIG. 118 and FIG. 119). The knife 257 may be fixed at the front part of the straight driving head 252, or may be assembled and disassembled at the front part of the straight driving head 252. The upper beam 254 of the straight driving head 252 may move back and forth along the tool slot 243 of the straight replaceable anvil 239, and the lower beam 255 may move back and forth along the staple cartridge slot 249 of the straight staple cartridge 240 (see FIG. 115, FIGS. 122-124).

When the upper beam 254 of the straight driving head 282 is inserted into the tool slot 243 of the straight replaceable anvil 239 by using a hand or a tool to overcome the force of the locating elastic part 241, the straight driving head 252 is therefore mounted in the straight replaceable anvil 239, and the upper beam 254 of the straight driving head 252 may move back and forth along the tool slot 243 of the straight replaceable anvil 239; at this time, moving the upper beam 254 of the straight driving head 252 back and forth along the tool slot 243 of the straight replaceable anvil 239, the position of the straight driving head 252 on the straight replaceable anvil 239 is adjusted so that the positioning part 247 of the locating elastic part 241 springs from the spring groove 245 of the straight replaceable anvil 239 into the constraining groove 256 of the straight driving head 252, and the positioning part 247 of the locating elastic part 241 constrains the mounting groove 244 of the straight replaceable anvil 239 and the inlay groove 253 of the straight driving head 252 at positions aligned with each other to form a replaceable inlay groove 258 (see FIG. 115). When the upper beam 254 of the straight driving head 252 is extracted out of the tool slot 243 of the straight replaceable anvil 239 by using a hand or a tool to overcome the force of the locating elastic part 241, the straight driving head 252 is therefore departed from the straight replaceable anvil 239 (see FIG. 114); at this time, the straight driving head 252 or the knife 257 may be selected.

Figure 123:
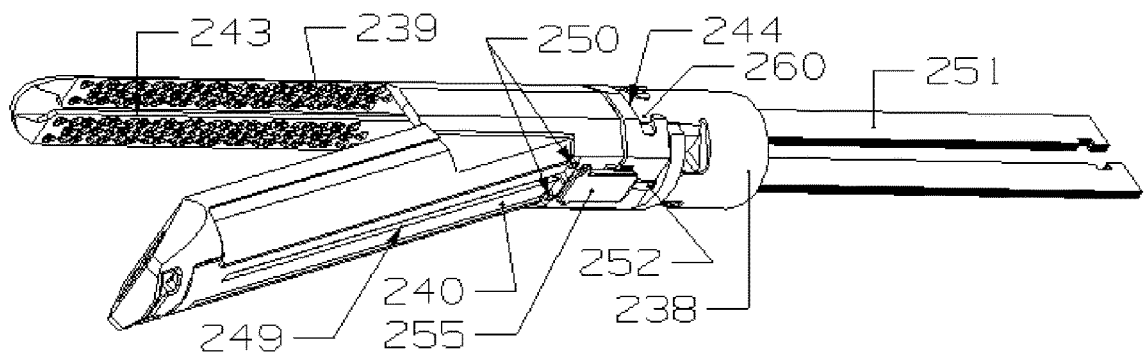

During the process of mounting the straight staple cartridge 240 to the straight replaceable anvil 239, step 1, the lower beam 255 of the straight driving head 252 is moved backward to exit the mounting position of the straight staple cartridge 240 (see FIG. 122); step 2, the key 248 is inserted into the groove 242, and the straight staple cartridge 240 is inserted on the straight replaceable anvil 239; step 3, the straight staple cartridge 240 rotates around the rotating support of the straight staple cartridge, such that the constraining key 250 of the straight staple cartridge 240 rotates to the position above the lower beam 255 of the straight driving head 252; step 4, the straight driving head 252 moves forward along the staple cartridge slot 249 and the tool slot 243, such that the lower beam 255 of the straight driving head 252 prevents the constraining key 250 of the straight staple cartridge 240 from rotating and moving down, then the straight staple cartridge 240 is mounted on the straight replaceable anvil 239 (see FIG. 123). During the process of removing the straight staple cartridge 240 from the straight replaceable anvil 239, step 1, the straight driving head 252 moves backward along the staple cartridge slot 249 and the tool slot 243, such that the lower beam 255 of the straight driving head 252 departs from the constraining key 250 of the straight staple cartridge 240 (see FIG. 122); step 2, the key 248 is removed from the opening of the groove 242, then the straight staple cartridge 240 could be removed from the straight replaceable anvil 239; at this time, the straight staple cartridge 240 may be selected.

The tool holder 238 includes a holder slot 259 in a forward-backward direction and a mounting key 260 located at the front part (see FIG. 112). The mounting key 260 is inserted into the mounting groove 244 between the tool holder 238 and the interchangeable tool 237 to form a tool inlay connection, and the interchangeable tool 237 is mounted on the tool holder 238 (see FIG. 110). The driving bar 251 includes an inlay key 261 at the front part (see FIG. 121). The inlay key 261 is inserted into the inlay groove 253 between the driving bar 251 and the straight driving head 252 of the driving member 236 to form a driving head inlay connection, and the straight driving head 252 is mounted on the driving bar 251 (see FIG. 120). When the mounting key 260 of the tool holder 238 and the inlay key 261 of the driving bar 251 are located at positions aligned with each other, a replaceable inlay key 262 is formed (see FIG. 111). When the replaceable inlay key 262 is inserted into the replaceable inlay groove 258, a replaceable inlay connection is formed (see FIG. 123). The driving member 236 could move back and forth in the tool slot 243 of the straight replaceable anvil 239 and in the holder slot 259 of the tool holder 238. During the process of removing the interchangeable tool 237 from the tool holder 238 and removing the straight driving head 252 from the driving bar 251 simultaneously, step 1, the driving member 236 drives the straight driving head 252 to overcome the force of the locating elastic part 241 to move along the tool slot 243 and the holder slot 259, the position of the tool inlay connection is aligned to the position of the driving head inlay connection to form the position of the replaceable inlay connection (see FIG. 123); at this time, the constraining groove 256 of the straight driving head 252 moves backward to return to the spring groove 245 of the straight replaceable anvil 239, the positioning part 247 of the locating elastic part 241 springs from the spring groove 245 of the straight replaceable anvil 239 into the constraining groove 256 of the straight driving head 252, the positioning part 247 of the locating elastic part 241 prevents the straight driving head 252 from moving back and forth in the straight replaceable anvil 239 (see FIG. 127) and constrains the mounting groove 244 of the straight replaceable anvil 239 and the inlay groove 253 of the straight driving head 252 at positions aligned with each other to form the replaceable inlay groove 258 and the replaceable inlay key 262 (see FIG. 111 and FIG. 115); step 2, the replaceable inlay groove 258 is removed from the replaceable inlay key 262 in the replaceable inlay connection, then the interchangeable tool 237 may be moved out of the tool holder 238 and the straight driving head 252 may be moved out of the driving bar 251 at the same time; at this time, the straight replaceable anvil 239, the straight staple cartridge 240, the straight driving head 252 or the knife 257 may be selected. During the process of mounting the interchangeable tool 237 on the tool holder 238 and mounting the straight driving head 252 on the driving bar 251 simultaneously, step 1, the inlay key 261 of the driving bar 251 and the mounting key 260 of the tool holder 238 are located at the position where the replaceable inlay connection is formed, then the replaceable inlay key 262 is formed (see FIG. 111); step 2, the replaceable inlay groove 258 is inserted on the replaceable inlay key 262 to form the replaceable inlay connection (see FIG. 123); step 3, the driving bar 251 drives the straight driving head 252 to overcome the force of the locating elastic part 241 to move forward along the holder slot 259 and insert into the tool slot 243, such that the driving member 236 prevents the mounting key 260 of the tool holder 238 from moving out of the mounting groove 244 of the interchangeable tool 237, then the interchangeable tool 237 is mounted on the tool holder 238; at the same time, the tool slot 243 prevents the inlay key 261 of the driving bar 251 from moving out of the inlay groove 253 of the straight driving head 252, then the straight driving head 252 is mounted on the driving bar 251 (see FIG.

Figure 124:
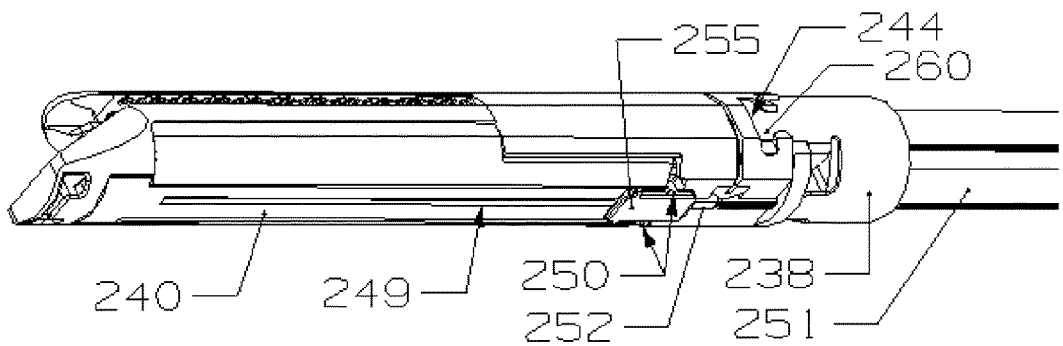
Figure 128:
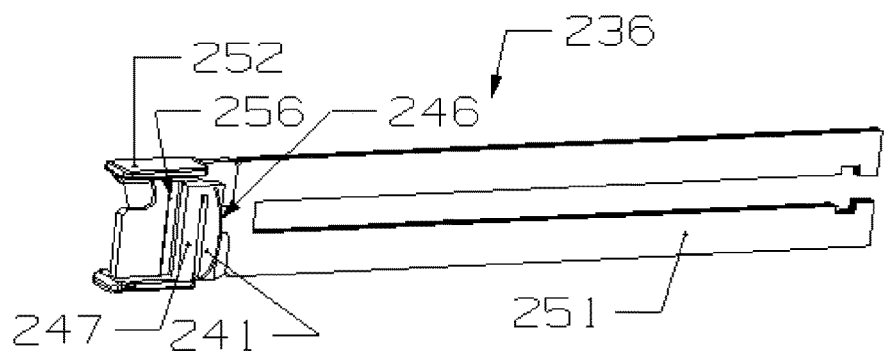
Figure 129:
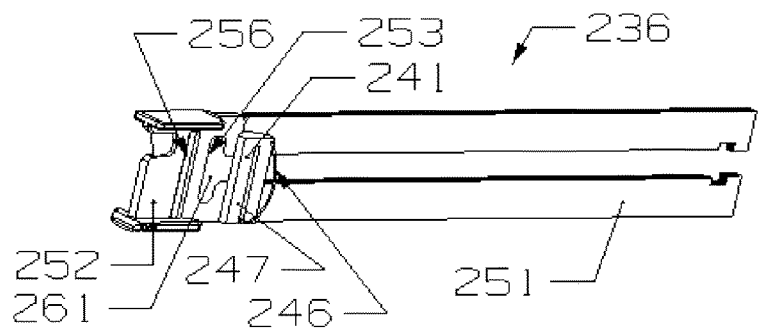

110 and FIG. 128); and when the driving bar 251 drives the straight driving head 252 to continue to move forward along the staple cartridge slot 249 and the tool slot 243, the straight driving head 252 closes the straight staple cartridge 240 and the straight replaceable anvil 239 (see FIG. 124 and FIG. 129).

FIGS. 130-141 describe the tool assembly 265 and the driving member 266 according to the tenth embodiment of the present disclosure. In the tenth embodiment, the tool assembly 235 of the ninth embodiment is replaced with the tool assembly 265, and the driving member 236 is replaced with the driving member 266 (see FIG. 130). The tool assembly 265 includes an interchangeable tool 267 and a tool holder 238. The interchangeable tool 267 includes a curved replaceable anvil 269, a curved staple cartridge 270, and a locating elastic part 241. The curved replaceable anvil 269 includes an opening groove 272, a tool slot 273 in a forward-backward direction and an open-end mounting groove 274 located at the back part (see FIG. 132 and FIG. 133). A spring groove 275 is provided in a side surface of the tool slot 273 of the curved replaceable anvil 269. The positioning part 247 of the locating elastic part 241 is mounted in the spring groove 275 (see FIG. 133). The spring 246 acts on the positioning part 247. The spring groove 275 prevents the locating elastic part 241 from moving back and forth within the curved replaceable anvil 269. The curved staple cartridge 270 includes a key 278, a staple cartridge slot 279 in a forward-backward direction and a constraining key 280 located at the back part (see FIG. 137 and FIG. 138). The key 278 is inserted into the groove 272 between the curved replaceable anvil 269 and the curved staple cartridge 270 to form a rotating support of the curved staple cartridge. The driving member 266 includes a driving bar 251 and a curved driving head 282 (see FIG. 131). The curved driving head 282 includes an open-end inlay groove 283 at the back part, an upper beam 284 at the upper, a lower beam 285 at the lower end, a constraining groove 286 at a side surface and a knife 287 at the front part (see FIG. 140 and FIG. 141). The knife 287 may be fixed at the front part of the curved driving head 282, or may be assembled and disassembled at the front part of the curved driving head 282. The upper beam 284 of the curved driving head 282 may move back and forth along the tool slot 273 of the curved replaceable anvil 269, and the lower beam 285 may move back and forth along the staple cartridge slot 279 of the curved staple cartridge 270 (see FIG. 130 and FIG. 139).

When the upper beam 284 of the curved driving head 282 is inserted into the tool slot 273 of the curved replaceable anvil 269 by using a hand or a tool to overcome the force of the locating elastic part 241, the curved driving head 282 is mounted in the curved replaceable anvil 269, and the upper beam 284 of the curved driving head 282 may move back and forth along the tool slot 273 of the curved replaceable anvil 269 (see FIG. 134); at this time, moving the upper beam 284 of the curved driving head 282 back and forth along the tool slot 273 of the curved replaceable anvil 269, the position of the curved driving head 282 on the curved replaceable anvil 269 is adjusted so that the positioning part 247 of the locating elastic part 241 springs from the spring groove 275 of the curved replaceable anvil 269 into the constraining groove 286 of the curved driving head 282, and the positioning part 247 of the locating elastic part 241 constrains the mounting groove 274 of the curved replaceable anvil 269 and the inlay groove 283 of the curved driving head 282 at positions aligned with each other to form a replaceable inlay groove 288 (see FIG. 134). When the upper beam 284 of the curved driving head 282 is extracted out of the tool slot 273 of the curved replaceable anvil 269 by using a hand or a tool to overcome the force of the locating elastic part 241, the curved driving head 282 is departed from the curved replaceable anvil 269; at this time, the curved driving head 282 or the knife 287 may be selected.

During the process of mounting the curved staple cartridge 270 to the curved replaceable anvil 269, step 1, the lower beam 285 of the curved driving head 282 moves backward to exit the mounting position of the curved staple cartridge 270 (see FIG. 135); step 2, the key 278 is inserted into the groove 272, and the curved staple cartridge 270 is inserted on the curved replaceable anvil 269; step 3, the curved staple cartridge 270 rotates around the rotating support of the curved staple cartridge, such that the constraining key 280 of the curved staple cartridge 270 rotates to the position above the lower beam 285 of the curved driving head 282; step 4, the curved driving head 282 moves forward along the staple cartridge slot 279 and the tool slot 273, such that the lower beam 285 of the curved driving head 282 prevents the constraining key 280 of the curved staple cartridge 270 from rotating and moving down, then the curved staple cartridge 270 is mounted on the curved replaceable anvil 269 (see FIG. 130). During the process of removing the curved staple cartridge 270 from the curved replaceable anvil 269, step 1, the curved driving head 282 moves backward along the staple cartridge slot 279 and the tool slot 273, such that the lower beam 285 of the curved driving head 282 departs from the constraining key 280 of the curved staple cartridge 270 (see FIG. 136); step 2, the key 278 is removed from the opening of the groove 272, then the curved staple cartridge 270 could be removed from the curved replaceable anvil 269; at this time, the curved staple cartridge 270 may be selected.

The curved replaceable anvil 269, the curved staple cartridge 270 and the curved driving head 282 of the endoscopic surgical instrument of the tenth embodiment of the present disclosure are curved to the left; a curved replaceable anvil, a curved staple cartridge and a curved driving head that are curved to the right may also be used. For the technical features, technical solutions, and technical effects that are not described or illustrated in the endoscopic surgical instrument of the tenth embodiment, please refer to the description or illustration of the endoscopic surgical instrument of the ninth embodiment.

After the endoscopic surgical instrument of the ninth or tenth embodiment of the present disclosure is used, according to the requirements of endoscopic surgery, a straight staple cartridge with the same anastomotic length and the same anastomotic thickness as the straight staple cartridge 240 may be replaced and mounted on the straight replaceable anvil 239; a straight staple cartridge with the same anastomotic length but different anastomotic thickness as the straight staple cartridge 240 may be replaced and mounted on the straight replaceable anvil 239; a straight staple cartridge with the same anastomotic thickness as the straight staple cartridge 240 but with a shorter anastomotic length than that of the straight replaceable anvil 239 may be replaced and installed on the straight replaceable anvil 239; a straight staple cartridge with a different anastomotic thickness from that of the straight staple cartridge 240 but with a shorter anastomotic length than that of the straight replaceable anvil 239 may also be replaced and mounted on the straight replaceable anvil 239; a straight replaceable anvil with an anastomotic length different from that of straight replaceable anvil 239 may also be replaced and mounted on the tool holder 238, then a corresponding straight staple cartridge may be mounted. It may also use the curved replaceable anvil 269 and the curved driving head 282 to replace the straight replaceable anvil 239 and the straight driving head 252, and mount the curved replaceable anvil 269 and the curved driving head 282 on the tool holder 238 and the driving bar 251, and install the corresponding curved staple cartridge 270; a curved staple cartridge with the same anastomotic length and the same anastomotic thickness as the curved staple cartridge 270 may also be replaced and mounted on the curved replaceable anvil 269; a curved staple cartridge with the same anastomotic length but different anastomotic thickness as the curved staple cartridge 270 may be replaced and mounted on the curved replaceable anvil 269; a curved staple cartridge with the same anastomotic thickness as the curved staple cartridge 270 but with a shorter anastomotic length than that of the curved replaceable anvil 269 may be replaced and mounted on the curved replaceable anvil 269; a curved staple cartridge with a different anastomotic thickness from that of the curved staple cartridge 270 but with a shorter anastomotic length than that of the curved replaceable anvil 269 may be replaced and mounted on the curved replaceable anvil 269; a curved replaceable anvil with an anastomotic length different from that of the curved replaceable anvil 269 may also be replaced and mounted on the tool holder 238, then a corresponding curved staple cartridge is mounted. It may also use the straight replaceable anvil 239 and the straight driving head 252 to replace the curved replaceable anvil 269 and the curved driving head 282, mount the straight replaceable anvil 239 and the straight driving head 252 on the tool holder 238 and driving bar 251, and install the corresponding straight staple cartridge 240. In the use of the endoscopic surgical instrument, if the knife on the driving head is found to be damaged, the spare driving head may be selected to replace the in-use driving head; or the spare knife may be selected to replace the in-use knife on the driving head.

FIGS. 142-162 describe the tool assembly 305 and the driving member 306 according to the eleventh embodiment of the present disclosure. The driving member 306 may move forward and backward in the tool assembly 305. The driving member 306 participates in controlling the actions of the tool assembly 305. The tool assembly 305 includes an interchangeable tool 307 and a tool holder 308 (see FIGS. 157-162). The interchangeable tool 307 includes a replaceable anvil 309, a staple cartridge 310 and a locating elastic part 311 (see FIG. 142). The replaceable anvil 309 includes an opening groove 312, a tool slot 313 in a forward-backward direction and an open-end mounting groove 314 located at the back part (see FIG. 144). The mounting groove 314 is a through groove that runs through both sides of the mounting groove 314. A spring groove 315 is provided in a side surface of the tool slot 313 of the replaceable anvil 309 (see FIG. 144 and FIG. 158). The locating elastic part 311 has a spring 316 and a positioning part 317 (see FIG. 146). The locating elastic part 311 is mounted in the spring groove 315 (see FIG. 143). The spring 316 acts on the positioning part 317. The spring groove 315 prevents the locating elastic part 311 from moving back and forth within the replaceable anvil 309. The staple cartridge 310 includes a key 318, a staple cartridge slot 319 in a forward-backward direction and a constraining key 320 located at the back part (see FIG. 148). The key 318 is inserted into the groove 312 between the replaceable anvil 309 and the staple cartridge 310 to form a rotating support of the staple cartridge. The driving member 306 includes a driving bar 321 and a driving head 322 (see FIG. 156). The driving head 322 includes an open-end inlay groove 323 at the back part, an upper beam 324 at the upper end, a lower beam 325 at the lower end, a constraining groove 326 at a side surface and a knife 327 at the front part (see FIG. 145 and FIG. 147). The knife 327 may be fixed at the front part of the driving head 322, or may be assembled and disassembled at the front part of the driving head 322. The upper beam 324 of the driving head 322 may move back and forth along the tool slot 313 of the replaceable anvil 309, and the lower beam 325 may move back and forth along the staple cartridge slot 319 of the staple cartridge 310 (see FIG. 142).

When the upper beam 324 of the driving head 322 is inserted into the tool slot 313 of the replaceable anvil 309 by using a hand or a tool to overcome the force of the locating elastic part 311, the driving head 322 is mounted in the replaceable anvil 309, and the upper beam 324 of the driving head 322 may move back and forth along the tool slot 313 of the replaceable anvil 309; at this time, moving the upper beam 324 of the driving head 322 back and forth along the tool slot 313 of the replaceable anvil 309, the position of the driving head 322 on the replaceable anvil 309 is adjusted so that the positioning part 317 of the locating elastic part 311 springs from the spring groove 315 of the replaceable anvil 309 into the constraining groove 326 of the driving head 322, and the positioning part 317 of the locating elastic part 311 constrains the mounting groove 314 of the replaceable anvil 309 and the inlay groove 323 of the driving head 322 at positions aligned with each other to form a replaceable inlay groove 328 (see FIG. 142). When the upper beam 324 of the driving head 322 is extracted out of the tool slot 313 of the replaceable anvil 309 by using a hand or a tool to overcome the force of the locating elastic part 311, the driving head 322 is departed from the replaceable anvil 309 (see FIG. 142, FIG. 143 and FIG. 145); at this time, the driving head 322 or the knife 327 may be selected.

During the process of mounting the staple cartridge 310 on the replaceable anvil 309, step 1, the lower beam 325 of the driving head 322 moves backward to exit the mounting position of the staple cartridge 310 by using a hand or a tool to overcome the force of the locating elastic part 311; step 2, the key 318 is inserted into the groove 312, and the staple cartridge 310 is inserted on the replaceable anvil 309; step 3, the staple cartridge 310 rotates around the rotating support of the staple cartridge, such that the constraining key 320 of the staple cartridge 310 rotates to the position above the lower beam 325 of the driving head 322; step 4, the driving head 322 moves forward along the staple cartridge slot 319 and the tool slot 313 by overcoming the force of the locating elastic part 311, such that the lower beam 325 of the driving head 322 prevents the constraining key 320 of the staple cartridge 310 from rotating and moving down, then the staple cartridge 310 is mounted on the replaceable anvil 309; the locating elastic part 311 constrains the mounting groove 314 of the replaceable anvil 309 and the inlay groove 323 of the driving head 322 at positions aligned with each other to form the replaceable inlay groove 328 (see FIG. 142). During the process of removing the staple cartridge 310 from the replaceable anvil 309, step 1, the driving head 322 moves backward along the staple cartridge slot 319 and the tool slot 313 by using a hand or a tool to overcome the force of the locating elastic part 311, such that the lower beam 325 of the driving head 322 departs from the constraining key 320 of the staple cartridge 310; step 2, the key 318 is removed from the opening of the groove 312, then the staple cartridge 310 could be removed from the replaceable anvil 309; at this time, the staple cartridge 310 may be selected.

The driving bar 321 includes an inlay key 330 at the front part (see FIG. 155). An inlay key 330 is inserted into the inlay groove 323 between the driving bar 321 and the driving head 322 of the driving member 306 to form a driving head inlay connection, and the driving head 322 is mounted on the driving bar 321 (see FIG. 156). The tool holder 308 includes a locking block 331, a locking spring 332, a holder slot 333 in a forward-backward direction and a mounting key 334 located at the front part (see FIGS. 157-162). The mounting key 334 is inserted into the mounting groove 314 between the tool holder 308 and the interchangeable tool 307 to form a tool inlay connection (see FIG. 159). The replaceable anvil 309 includes a locking groove 329 (see FIG. 144). The locking block 331 and the locking groove 329 are respectively located at the front and back sides of the mounting joint 335 between the tool inlay connection (see FIGS. 157-162). The force of the locking spring 332 causes the locking block 331 to move toward the direction of the locking groove 329.

When the mounting key 334 of the tool holder 308 and the inlay key 330 of the driving bar 321 are located at positions aligned with each other, a replaceable inlay key 336 is formed (see FIG. 151 and FIG. 152). When the replaceable inlay key 336 is inserted into the replaceable inlay groove 328, a replaceable inlay connection is formed (see FIG. 159). The driving member 306 could move back and forth in the tool slot 313 of the replaceable anvil 309 and in the holder slot 333 of the tool holder 308 (see FIG. 158, FIG. 160 and FIG. 162). During the process of removing the interchangeable tool 307 from the tool holder 308 and removing the driving head 322 from the driving bar 321 simultaneously, step 1, the driving member 306 drives the driving head 322 to overcome the force of the locating elastic part 311 to move along the tool slot 313 and the holder slot 333, the position of the tool inlay connection is aligned to the position of the driving head inlay connection to form the position of the replaceable inlay connection (see FIG. 157); at this time, the constraining groove 326 of the driving head 322 moves backward to return to the spring groove 315 of the replaceable anvil 309, the positioning part 317 of the locating elastic part 311 springs from the spring groove 315 of the replaceable anvil 309 into the constraining groove 326 of the driving head 322, the positioning part 317 of the locating elastic part 311 prevents the driving head 322 from moving back and forth in the replaceable anvil 309 and constrains the mounting groove 314 of the replaceable anvil 309 and the inlay groove 323 of the driving head 322 at positions aligned with each other (see FIG. 142, FIG. 149, FIG. 150, FIG. 157 and FIG. 158); step 2, the locking block 331 overcomes the force of the locking spring 332 to exit the locking groove 329, such that the locking block 331 exits the mounting joint 335 between the tool inlay connection, a replaceable inlay groove 328 and a replaceable inlay key 336 are formed (see FIG. 151, FIG. 152, FIG. 159 and FIG. 160); step 3, the replaceable inlay groove 328 is removed from the replaceable inlay key 336 in the replaceable inlay connection, then the interchangeable tool 307 can be moved out of the tool holder 308 and the driving head 322 can be moved out of the driving bar 321 at the same time; at this time, the replaceable anvil 309, the staple cartridge 310, the driving head 322 or the knife 327 may be selected. During the process of mounting the interchangeable tool 307 on the tool holder 308 and mounting the driving head 322 on the driving bar 321 simultaneously, step 1, the inlay key 330 of the driving bar 321 and the mounting key 334 of the tool holder 308 are located at positions where the replaceable inlay connection can be formed (see FIG. 149 and FIG. 150); step 2, the locking block 331 overcomes the force of the locking spring 332 to move backward to the mounting joint 335 where the tool inlay connection can be formed, and the replaceable inlay key 336 is formed (see FIG. 151 and FIG. 152); step 3, the replaceable inlay groove 328 is inserted on the replaceable inlay key 336 to form the replaceable inlay connection; step 4, the locking block 331 is inserted into the locking groove 329 under the force of the locking spring 332, and the locking block 331 is inserted across the front and back sides of the mounting joint 335 between the tool inlay connection, such that the locking block 331 prevents the mounting key 334 from moving out of the mounting groove 314 of the tool inlay connection, that is, the interchangeable tool 307 can be mounted on the tool holder 308, and the driving head 322 can be mounted on the driving bar 321 at the same time (see FIG. 157 and FIG. 158). After that, the driving bar 321 can move forward along the holder slot 333 to insert into the tool slot 313, such that the driving member 306 prevents the mounting key 334 of the tool holder 308 from moving out of the mounting groove 314 of the interchangeable tool 307. The interchangeable tool 307 is further constrained on the tool holder 308. At the same time, the tool slot 313 prevents the inlay key 330 of the driving bar 321 from moving out of the inlay groove 323 of the driving head 322, and the driving head 322 is further constrained on the driving bar 321. At the same time, when the driving bar 321 drives the driving head 322 to continue to move forward along the staple cartridge slot 319 and the tool slot 313, the driving head 322 closes the staple cartridge 310 and the replaceable anvil 309 (see FIG. 161 and FIG. 162).

The replaceable anvil 309, the staple cartridge 310 and the driving head 322 of the endoscopic surgical instrument of the eleventh embodiment may adopt a straight replaceable anvil, a straight staple cartridge, and a straight driving head; they may also adopt a curved replaceable anvil, a curved staple cartridge and a curved driving head. After the endoscopic surgical instrument of the eleventh embodiment of the present disclosure is used, according to the requirements of endoscopic surgery, a staple cartridge with the same anastomotic length and the same anastomotic thickness as the staple cartridge 310 may be replaced and mounted on the replaceable anvil 309; a staple cartridge with the same anastomotic length but different anastomotic thickness as the staple cartridge 310 may also be replaced and mounted on the replaceable anvil 309; a staple cartridge with the same anastomotic thickness as the staple cartridge 310 but with a shorter anastomotic length than the replaceable anvil 309 may be replaced and mounted on the replaceable anvil 309; a staple cartridge with a different anastomotic thickness from that of the staple cartridge 310 but with a shorter anastomotic length than that of the replaceable anvil 309 may be replaced and mounted on the replaceable anvil 309; a replaceable anvil with an anastomotic length different from that of the replaceable anvil 309 may also be replaced and mounted on the tool holder 308, then a corresponding staple cartridge is mounted. In the use of the endoscopic surgical instrument, if the knife 327 on the driving head 322 is found to be damaged, a spare driving head may be selected to replace the in-use driving head; or a spare knife may be selected to replace the in-use knife on the driving head.

FIGS. 163-175 and FIG. 183 describe the tool assembly 350 and the driving member 351 according to the twelfth embodiment of the present disclosure. In the endoscopic surgical instrument of the twelfth embodiment, the tool assembly 305 of the eleventh embodiment is replaced with the tool assembly 350, and the driving member 306 is replaced with the driving member 351. The tool assembly 350 includes a first type of interchangeable tool 352 and a tool holder 353 (see FIGS. 170-175). The first type of interchangeable tool 352 includes a first tool 356, a first type of pivot 357, a tool slot 358 in a forward-backward direction and an open-end mounting groove 359 located at the back part (see FIGS. 170-175). The first tool 356 can rotate around the first type of pivot 357. The driving member 351 includes a driving bar 360 and a driving head 361 (see FIG. 166). The driving head 361 includes an open-end inlay groove 362 at the back part and a constraining groove 367 at the side surface (see FIG. 168). The driving bar 360 includes an inlay key 372 at the front part (see FIG. 167). The inlay key 372 is inserted into the inlay groove 362 between the driving bar 360 and the driving head 361 to form a driving head inlay connection. The tool holder 353 includes a mounting key 369 and a locking groove 355 located at the front part and a holder slot 373 in a forward-backward direction (see FIG. 169).

As shown in FIGS. 170-175, a spring groove 366 is provided in a side surface of the tool slot 358 of the first type of interchangeable tool 352. The spring 364 and the positioning part 365 of the locating elastic part 363 (see FIG. 183) are mounted in the spring groove 366. The spring groove 366 prevents the locating elastic part 363 from moving back and forth within the first type of interchangeable tool 352. The spring 364 of the locating elastic part 363 acts on the positioning part 365. When the driving head 361 is mounted in the tool slot 358 of the first type of interchangeable tool 352, the positioning part 365 of the locating elastic part 363 springs from the spring groove 366 of the first type of interchangeable tool 352 into the constraining groove 367 of the driving head 361, the positioning part 365 of the locating elastic part 363 constrains the mounting groove 359 of the first type of interchangeable tool 352 and the inlay groove 362 of the driving head 361 at positions aligned with each other to form a replaceable inlay groove 368 (see FIG. 164 and FIG. 171). When the driving bar 360 drives the driving head 361 to move, after the positioning part 365 of the locating elastic part 363 departs from the constraining groove 367 of the driving head 361, the driving member 351 prevents the locating elastic part 363 from departing from the spring groove 366 of the first type of interchangeable tool 352 (see FIG. 175); and when the constraining groove 367 of the driving head 361 returns to the spring groove 366 of the first type of interchangeable tool 352, the positioning part 365 of the locating elastic part 363 springs from the spring groove 366 of the first type of interchangeable tool 352 into the constraining groove 367 of the driving head 361, the positioning part 365 of the locating elastic part 363 constrains the mounting groove 359 of the first type of interchangeable tool 352 and the inlay groove 362 of the driving head 361 at positions aligned with each other again, so as to form a replaceable inlay groove 368 (see FIG. 164 and FIG. 173). The mounting key 369 is inserted into the mounting groove 359 between the tool holder 353 and the first type of interchangeable tool 352 to form a tool inlay connection. The first type of interchangeable tool 352 includes a locking block 354 and a locking spring 370 (see FIG. 163). The locking block 354 and the locking groove 355 are respectively located at the front and back sides of the mounting joint 371 between the tool inlay connection (see FIG. 170 and FIG. 171). The force of the locking spring 370 causes the locking block 354 to move toward the direction of the locking groove 355.

As shown in FIGS. 170-175, during the process of removing the first type of interchangeable tool 352 from the tool holder 353 and removing the driving head 361 from the driving bar 360 at the same time, step 1, the driving member 351 moves along the tool slot 358 and the holder slot 373, the position of the tool inlay connection is aligned to the position of the driving head inlay connection to form the position of the replaceable inlay connection (see FIG. 172 and FIG. 173); step 2, the locking block 354 overcomes the force of the locking spring 370 to exit the locking groove 355, such that the locking block 354 exits the mounting joint 371 between the tool inlay connection (see FIG. 170 and FIG. 171); step 3, the replaceable inlay groove 368 is removed from the replaceable inlay key 374 in the replaceable inlay connection, then the first type of interchangeable tool 352 can be moved out of the tool holder 353, and the driving head 361 can be moved out of the driving bar 360 at the same time; at this time, the first type of interchangeable tool 352 and the driving head 361 may be selected. During the process of mounting the first type of interchangeable tool 352 on the tool holder 353 and mounting the driving head 361 on the driving bar 360 at the same time, step 1, the mounting key 369 of the tool holder 353 and the inlay key 372 of the driving bar 360 are located at positions aligned with each other to form a replaceable inlay key 374 (see FIG. 165); step 2, the locking block 354 overcomes the force of the locking spring 370 to move backward, so as to form the replaceable inlay groove 368 (see FIG. 164); step 3, the replaceable inlay groove 368 is inserted on the replaceable inlay key 374 to form the replaceable inlay connection (see FIG. 170 and FIG. 171); step 4, the locking block 354 is inserted into the locking groove 355 under the force of the locking spring 370, and the locking block 354 is inserted across the front and back sides of the mounting joint 371 between the tool inlay connection, such that the locking block 354 prevents the mounting key 369 from moving out of the mounting groove 359 of the tool inlay connection, then the first type of interchangeable tool 352 can be mounted on the tool holder 353, and the driving head 361 can be mounted on the driving bar 360 at the same time (see FIG. 163, FIG. 172 and FIG. 173); and the driving member 351 can move along the holder slot 373 and the tool slot 358, such that the driving member 351 prevents the mounting key 369 of the tool holder 353 from moving out of the mounting groove 359 of the first type of interchangeable tool 352, and the first type of interchangeable tool 352 is further constrained on the tool holder 353; at the same time, the tool slot 358 prevents the inlay key 372 of the driving bar 360 from moving out of the inlay groove 362 of the driving head 361, which further constrains the driving head 361 on the driving bar 360 (see FIG. 175).

FIGS. 176-183 describe the tool assembly and the driving member according to the thirteenth embodiment of the present disclosure. In the endoscopic surgical instrument of the thirteenth embodiment, the first type of interchangeable tool 352 of the twelfth embodiment is replaced with a second type of interchangeable tool 382, and the driving member 351 is replaced with a driving member 381. The first type of interchangeable tool 352 of the twelfth embodiment and the second type of interchangeable tool 382 of the thirteenth embodiment are not simultaneously mounted on the tool holder 353. The second type of interchangeable tool 382 includes a second tool 386, a second type of pivot 387, an tool slot 388 in a forward-backward direction and an open-end mounting groove 389 located at the back part (see FIGS. 176-178 and FIG. 180). The second tool 386 can rotate around the second type of pivot 387. The driving member 381 includes a driving bar 360 and a driving head 391 (see FIG. 181). The driving head 391 includes an open-end inlay groove 392 at the back part and a constraining groove 397 at the side surface (see FIG. 182). The driving head 391 is mounted in the tool slot 388 of the second type of interchangeable tool 382 (see FIG. 180). The inlay key 372 is inserted into the inlay groove 392 between the driving bar 360 and the driving head 391 to form a driving head inlay connection (see FIG. 181).

A spring groove 396 is provided in a side surface of the tool slot 388 of the second type of interchangeable tool 382 (see FIG. 180). The spring 364 and the positioning part 365 of the locating elastic part 363 are mounted in the spring groove 396 (see FIG. 180 and FIG. 183). The spring groove 396 prevents the locating elastic part 363 from moving back and forth within the second type of interchangeable tool 382. When the driving head 391 is mounted in the second type of interchangeable tool 382, the positioning part 365 of the locating elastic part 363 springs from the spring groove 396 of the second type of interchangeable tool 382 into the constraining groove 397 of the driving head 391, the positioning part 365 of the locating elastic part 363 constrains the mounting groove 389 of the second type of interchangeable tool 382 and the inlay groove 392 of the driving head 391 at positions aligned with each other, to form the replaceable inlay groove 398 (see FIGS. 177-180). When the replaceable inlay key 374 is inserted into the replaceable inlay groove 398, the replaceable inlay connection is formed.

As shown in FIG. 179 and FIG. 180, the mounting key 369 is inserted into the mounting groove 389 between the tool holder 353 and the second type of interchangeable tool 382 to form the tool inlay connection, and the second type of interchangeable tool 382 is mounted on the tool holder 353. The second type of interchangeable tool 382 includes a locking block 354 and a locking spring 370 (see FIGS. 176-180). The locking block 354 and the locking groove 355 are respectively located at the front and back sides of the mounting joint 399 between the tool inlay connection (see FIG. 179 and FIG. 180). During the process of mounting the second type of interchangeable tool 382 on the tool holder 353 and mounting the driving head 391 on the driving bar 360 at the same time, step 1, the locking block 354 overcomes the force of the locking spring 370 to exit the mounting joint 399 of the tool inlay connection, the replaceable inlay groove 398 is formed (see FIG. 177 and FIG. 178); step 2, the replaceable inlay groove 398 is inserted on the replaceable inlay key 374 to form the replaceable inlay connection, the second type of interchangeable tool 382 is inserted on the tool holder 353, and the driving head 391 is inserted on the driving bar 360; step 3, the locking block 354 is inserted into the locking groove 355 under the force of the locking spring 370, and the locking block 354 is inserted across the front and back sides of the mounting joint 399 between the tool inlay connection, such that the locking block 354 prevents the mounting key 369 from moving out of the mounting groove 389 of the tool inlay connection, then the second type of interchangeable tool 382 can be mounted on the tool holder 353 and the driving head 391 can be mounted on the driving bar 360 at the same time (see FIG. 179 and FIG. 180) During the process of removing the second type of interchangeable tool 382 from the tool holder 353 and removing the driving head 391 from the driving bar 360 at the same time, step 1, the driving member 381 moves along the tool slot 388 and the holder slot 373, the position of the tool inlay connection is aligned to the position of the driving head inlay connection to form the position of the replaceable inlay connection (see FIG. 179 and FIG. 180); step 2, the locking block 354 overcomes the force of the locking spring 370 to exit the locking groove 355, such that the locking block 354 exits the mounting joint 399 between the tool inlay connection (see FIG. 177 and FIG. 178); step 3, the replaceable inlay groove 398 is removed from the replaceable inlay key 374 in the replaceable inlay connection, then the second type of interchangeable tool 382 can be moved out of the tool holder 353 and the driving head 391 can be moved out of the driving bar 360 at the same time; at this time, the second type of interchangeable tool 382 and the driving head 391 may be selected.

For the technical features, technical solutions and technical effects that are not described or illustrated in the endoscopic surgical instrument of the thirteenth embodiment, please refer to the description or illustration of the endoscopic surgical instrument of the twelfth embodiment.

Due to that the axis direction of the first type of pivot 357 of the first tool 356 after the first type of interchangeable tool 352 of the twelfth embodiment is mounted on the tool holder 353 (see FIG. 163, FIG. 164, FIGS. 170-175) forms an angle with the axis direction of the second type of pivot 387 of the second tool 386 after the second type of interchangeable tool 382 of the thirteenth embodiment is mounted on the tool holder 353 (see FIGS. 178-180), when the articulation component of the endoscopic surgical instrument rotates in the same plane, the open/close direction of the first tool 356 of the first type of interchangeable tool 352 of the twelfth embodiment forms an angle with the open/close direction of the second tool 386 of the second type of interchangeable tool 382 of the thirteenth embodiment. Therefore, the first type of interchangeable tool 352 of the twelfth embodiment or the second type of interchangeable tool 382 of the thirteenth embodiment is selected to be mounted on the tool holder 353 according to the requirements of endoscopic surgeries on the open/close direction of the tool. After the endoscopic surgical instrument of the twelfth embodiment or the thirteenth embodiment is used, according to the requirements of endoscopic surgery, an interchangeable tool with the same function as the first type of interchangeable tool 352 or the second type of interchangeable tool 382 may be mounted on the tool holder 353, or a interchangeable tool with a different function from the first type of interchangeable tool 352 or the second type of interchangeable tool 382 may be mounted on the tool holder 353, thereby increasing the scope of the endoscopic surgeries.

The technical features and technical solutions of the multipurpose endoscopic surgical instrument of the above thirteen embodiments of the present disclosure may be implemented independently, cross-implemented, or combined to achieve the best technical effect. The multipurpose endoscopic surgical instrument of the above thirteen embodiments may adopt a manual operation assembly to form a manual multipurpose endoscopic surgical instrument, or adopt an electric operation assembly to form an electric multipurpose endoscopic surgical instrument, or adopt a robotic operation assembly to form a robotic multipurpose endoscopic surgical instrument.

According to the above detailed description, compared with the conventional various endoscopic surgical instruments, the multipurpose endoscopic surgical instruments of the present disclosure have the following technical effects: the process of replacing the driving head and/or interchangeable tool of the same or different purposes is simple, convenient, fast and safe; the cost of endoscopic surgery is significantly reduced; the scope of the endoscopic surgeries is increased; and the requirements for multiple purposes of endoscopic surgery are achieved.

The multipurpose endoscopic surgical instrument of the present disclosure is particularly suitable for quickly replacing replaceable parts, interchangeable tools, and/or driving heads of the same or different purposes on manual, electric and robotic endoscopic surgical instruments. The part or the whole of the replaceable parts, interchangeable tools and/or driving heads of the multipurpose endoscopic surgical instrument of the present disclosure may adopt metal parts or metal components that are easily sterilized, and may be made into reusable replaceable parts, interchangeable tools and/or driving heads. Various replaceable parts, interchangeable tools and/or driving heads of the multipurpose endoscopic surgical instrument of the present disclosure may be combined into an endoscopic surgical instrument set that fits the requirements of a specific endoscopic surgical scope, according to the scope of endoscopic surgery.

The tool assembly of the multipurpose endoscopic surgical instrument of the present disclosure may be a tool assembly without energy or a tool assembly with energy. The multipurpose endoscopic surgical instruments of the present disclosure may be combined into various endoscopic cutting staplers, endoscopic suturing devices, endoscopic surgical forceps, endoscopic surgical cutting forceps, endoscopic surgical clip applier, endoscopic surgical scissors, endoscopic knifes, endoscopic surgical syringes, endoscopic surgical electric knives, endoscopic surgical ultrasonic knives and other endoscopic surgical instruments, so as to meet the requirements for multiple purposes of endoscopic surgery.

What is claimed is:

1. A multipurpose endoscopic surgical instrument having a tool assembly, an elongated body and an operation assembly, wherein said elongated body connects said operation assembly and said tool assembly, wherein the operation assembly comprises a driving member which comprises an inserting block at a front and controls actions of the tool assembly, and wherein the tool assembly comprising:
   a mounting key, an open-end mounting groove, a tool holder and
   an interchangeable tool which is mounted on said tool holder and includes a tool slot in a forward-backward direction, wherein the interchangeable tool and the tool holder are connected with each other by inserting said mounting key into said open-end mounting groove;
   wherein the interchangeable tool is configured such that upon mounting of the interchangeable tool on the tool holder, the mounting key is inserted into the open-end mounting groove through an opening of the open-end mounting groove, and the interchangeable tool is inserted on the tool holder; the operation assembly controls said inserting block on said driving member to move along said tool slot, until the inserting block on the driving member prevents the mounting key from moving out of the opening of the open-end mounting groove, and the interchangeable tool is mounted on the tool holder;
   upon removal of the interchangeable tool from the tool holder, the operation assembly controls the inserting block on the driving member to move in the tool slot, until the inserting block on the driving member exits the position where the open-end mounting key is prevented from moving out of the opening of the open-end mounting groove; the mounting key is removed from the opening of the open-end mounting groove, then the interchangeable tool is removed from the tool holder, and the interchangeable tool may be selected.

2. The multipurpose endoscopic surgical instrument according to claim 1, wherein said interchangeable tool is classified into a first type of interchangeable tool and a second type of interchangeable tool; wherein said first type of interchangeable tool comprises a first tool and a first type of pivot, and said first tool rotates around said first type of pivot; wherein said second type of interchangeable tool comprises a second tool and a second type of pivot, and said second tool rotates around said second type of pivot; wherein the mounting key is inserted into the open-end mounting groove between the first type of interchangeable tool and the tool holder to form a first tool inlay connection, and wherein the mounting key is inserted into the open-end mounting groove between the second type of interchangeable tool and the tool holder to form a second tool inlay connection; wherein the first type of interchangeable tool and the second type of interchangeable tool are not simultaneously mounted on the tool holder; wherein an axis direction of the first type of pivot of the first type of interchangeable tool after the first type of interchangeable tool is mounted on the tool holder forms an angle with an axis direction of the second type of pivot of the second type of interchangeable tool after the second type of interchangeable tool is mounted on the tool holder.

3. The multipurpose endoscopic surgical instrument according to claim 1, wherein the mounting key is inserted into the open-end mounting groove between the interchangeable tool and the tool holder to form a tool inlay connection;
   wherein the interchangeable tool is configured such that upon removal of the interchangeable tool from the tool holder, the operation assembly controls the inserting block on the driving member to move along the tool slot, until the inserting block on the driving member exits the position where the tool inlay connection is constrained, and the open-end mounting groove is removed out of the mounting key from the tool inlay connection; the interchangeable tool is removed from the tool holder, and the interchangeable tool may be selected;
   upon mounting of the interchangeable tool on the tool holder, the operation assembly controls the inserting block on the driving member to move, until the inserting block on the driving member exits the position where the tool inlay connection is constrained; the open-end mounting groove is inserted on the mounting key to form an tool inlay connection; the operation assembly controls the inserting block on the driving member to move along the tool slot, until the inserting block on the driving member prevents the mounting key from moving out of the opening of the open-end mounting groove, and the interchangeable tool is mounted on the tool holder.

4. The multipurpose endoscopic surgical instrument according to claim 3, wherein the tool holder comprises the mounting key at a front part and a holder slot in a forward-backward direction, wherein the interchangeable tool comprises the open-end mounting groove at a back part, wherein the driving member comprises a driving bar and a driving head, wherein said driving head comprises an opening inlay groove at a back part, wherein said driving bar comprises an inlay key at a front part, wherein said inlay key is inserted into said inlay groove between the driving bar and the driving head to form a driving head inlay connection, wherein the position of the tool inlay connection is aligned to the position of said driving head inlay connection to form a replaceable inlay connection, wherein the driving head is mounted in the tool slot of the interchangeable tool, wherein the driving bar is mounted in said holder slot of the tool holder, wherein a replaceable inlay groove is formed when the open-end mounting groove of the interchangeable tool and the inlay groove of the driving head are located at a position aligned with each other, wherein a replaceable inlay key is formed when the mounting key of the tool holder and the inlay key of the driving bar are located at a position aligned with each other, wherein said replaceable inlay connection is formed when said replaceable inlay key is inserted into said replaceable inlay groove;

wherein the interchangeable tool and the driving head are configured such that upon removal of the interchangeable tool and removal of the driving head from the driving bar at the same time, the driving member moves along the tool slot and the holder slot, and the position of the tool inlay connection is aligned to the position of the driving head inlay connection to form the position of the replaceable inlay connection, then the replaceable inlay groove is removed from the replaceable inlay key in the replaceable inlay connection; the interchangeable tool is moved out of the tool holder and the driving head is moved out of the driving bar at the same time, and the interchangeable tool or the driving head may be selected;

upon mounting of the interchangeable tool on the tool holder and mounting of the driving head on the driving bar at the same time, the mounting key of the tool holder and the inlay key of the driving bar are located at a position aligned with each other to form the replaceable inlay key; the replaceable inlay groove is inserted on the replaceable inlay key to form the replaceable inlay connection, at this time, the mounting key of the tool holder is inserted into the open-end mounting groove of the interchangeable tool between the tool holder and the interchangeable tool to form the tool inlay connection, and the inlay key of the driving bar is inserted into the inlay groove of the driving head between the driving bar and the driving head to form the driving head inlay connection; the driving member moves along the holder slot and the tool slot, such that the driving member prevents the mounting key of the tool holder from moving out of the open-end mounting groove of the interchangeable tool, and the interchangeable tool is mounted on the tool holder, at the same time, the tool slot prevents the inlay key of the driving bar from moving out of the inlay groove of the driving head, and the driving head is mounted on the driving bar.

5. The multipurpose endoscopic surgical instrument according to claim 3, wherein the tool holder comprises the open-end mounting groove at a front part, and a holder slot in a forward-backward direction, wherein the interchangeable tool comprises the mounting key at a back part, wherein the driving member comprises a driving bar and a driving head, wherein said driving head comprises an inlay key at a back part, wherein said driving bar comprises an opening inlay groove at a front part, wherein said inlay key is inserted into said inlay groove between the driving bar and the driving head to form a driving head inlay connection, wherein the position of the tool inlay connection is aligned to the position of the driving head inlay connection to form a replaceable inlay connection, wherein the driving head is mounted in the tool slot of the interchangeable tool, wherein the driving bar is mounted in the holder slot of the tool holder, wherein a replaceable inlay block is formed when the mounting key of the interchangeable tool and the inlay block of the driving head are located at a position aligned with each other, wherein a replaceable inlay groove is formed when the replaceable inlay block is inserted into the replaceable inlay groove, wherein a replaceable inlay connection is formed when the open-end mounting groove of the tool holder and the inlay groove of the driving bar are located at a position aligned with each other;

wherein the interchangeable tool and the driving head are configured such that upon removal of the interchangeable tool and removal of the driving head from the driving bar at the same time, the driving member moves along the tool slot and the holder slot, and the position of the tool inlay connection is aligned to the position of the driving head inlay connection to form the position of the replaceable inlay connection, then the replaceable inlay groove is removed from the replaceable inlay key in the replaceable inlay connection; the interchangeable tool is moved out of the tool holder and the driving head is moved out of the driving bar at the same time, and the interchangeable tool and the driving head may be selected;

wherein upon mounting of the interchangeable tool on the tool holder and mounting of the driving head on the driving bar at the same time, the open-end mounting groove of the tool holder and the inlay groove of the driving bar are located at the position aligned with each other to form the replaceable inlay groove; the replaceable inlay groove is inserted on the replaceable inlay key to form the replaceable inlay connection, at this time, the open-end mounting groove of the tool holder is inserted into the mounting key of the interchangeable tool between the tool holder and the interchangeable tool to form the tool inlay connection, and the inlay groove of the driving bar is inserted on the inlay key of the driving head between the driving bar and the driving head to form the driving head inlay connection; the driving member moves along the holder slot and the tool slot, such that the driving member prevents the open-end mounting groove of the tool holder from moving out of the mounting key of the interchangeable tool, and the interchangeable tool is mounted on the tool holder, at the same time, the tool slot prevents the inlay groove of the driving bar from moving out of the inlay key of the driving head, and the driving head is mounted on the driving bar.

6. The multipurpose endoscopic surgical instrument according to claim 3, wherein a locating elastic part is mounted in the interchangeable tool, wherein said locating elastic part acts on the driving head to constrain the interchangeable tool and the driving head at the position of a replaceable inlay connection when the driving head is mounted in the interchangeable tool.

7. The multipurpose endoscopic surgical instrument according to claim 1, wherein said driving member comprises a driving bar and a driving head, wherein said driving head is classified into an in-use driving head and a spare driving head, wherein an inlay key is inserted into an opening inlay groove between said driving bar and said in-use driving head to form a driving head inlay connection, wherein the in-use driving head is mounted on the driving bar while said spare driving head has not been mounted on the driving bar;

wherein the in-use driving head is configured such that upon replacement of the in use driving head, the interchangeable tool is removed from the tool holder; the operation assembly controls the in-use driving head on the driving bar to move forward until the in-use driving head extends out of the tool holder; the inlay key is removed from the inlay groove, then the in-use driving head is removed from the driving bar; the inlay key is inserted into the inlay groove between the driving bar and the spare driving head to form the driving head inlay connection, and the spare driving head is mounted on the driving bar; the operation assembly controls the spare driving head on the driving bar to move backward until the spare driving head returns to the tool holder; the interchangeable tool is mounted on the tool holder.

8. The multipurpose endoscopic surgical instrument according to claim 1, wherein the tool holder comprises an opening constraining groove, wherein the inserting block is located at the opening of the constraining groove, wherein said interchangeable tool comprises a constraining key at the back part;

wherein the interchangeable tool is configured such that upon mounting of the interchangeable tool on the tool holder, the operation assembly controls the inserting block on the driving member to move backward at the opening of said constraining groove of the tool holder, so as to open the opening of the constraining groove; the mounting key and said constraining key are inserted into the open-end mounting groove and the constraining groove through the opening of the open-end mounting groove and the opening of the constraining groove; the operation assembly controls the inserting block on the driving member to move forward at the opening of the constraining groove, so as to close the opening of the constraining groove of the tool holder, such that the inserting block prevents the mounting key and the constraining key from moving out of the opening of the open-end mounting groove and the opening of the constraining groove, and the interchangeable tool is mounted on the tool holder;

upon removal of the interchangeable tool from the tool holder, the operation assembly controls the inserting block on the driving member to move backward at the opening of the constraining groove of the tool holder, so as to open the opening of the constraining groove; the mounting key and the constraining key are removed from the opening of the open-end mounting groove and the opening of the constraining groove, then the interchangeable tool is removed from the tool holder, and the interchangeable tool may be selected.

\* \* \* \* \*